(12) United States Patent
Poulton et al.

(10) Patent No.: US 11,220,549 B2
(45) Date of Patent: Jan. 11, 2022

(54) ANTIBODIES THAT SPECIFICALLY BIND TO TL1A AND METHODS OF TREATING RESPIRATORY TRACT DISEASES

(71) Applicant: Cephalon, Inc., Frazer, PA (US)

(72) Inventors: Lynn Dorothy Poulton, Macquarie Park (AU); Matthew Pollard, Pullenvale (AU); Anthony G. Doyle, Macquarie Park (AU); Bridget A. Cooksey, Macquarie Park (AU); Vanya Pande, Macquarie Park (AU); Adam W. Clarke, Macquarie Park (AU)

(73) Assignee: Cephalon, Inc., Frazer, PA (US)

( * ) Notice: Subject to any disclaimer, the term of this patent is extended or adjusted under 35 U.S.C. 154(b) by 330 days.

(21) Appl. No.: 16/164,509

(22) Filed: Oct. 18, 2018

(65) Prior Publication Data

US 2019/0106486 A1 Apr. 11, 2019

Related U.S. Application Data

(62) Division of application No. 15/267,213, filed on Sep. 16, 2016, now Pat. No. 10,138,296.
(Continued)

(51) Int. Cl.
*C07K 16/28* (2006.01)
*A61P 11/06* (2006.01)
(Continued)

(52) U.S. Cl.
CPC .......... *C07K 16/2875* (2013.01); *A61P 11/06* (2018.01); *C07K 16/241* (2013.01);
(Continued)

(58) Field of Classification Search
None
See application file for complete search history.

(56) References Cited

U.S. PATENT DOCUMENTS 7,597,886 B2 10/2009 Yu et al.
7,820,798 B2 10/2010 Yu et al.
(Continued)

FOREIGN PATENT DOCUMENTS

JP 2018512167 A 5/2018
WO WO 2005018571 A2 3/2005
(Continued)

OTHER PUBLICATIONS

Facco et al., TL1A_DR3 axis involvement in the inflammatory cytokine network during pulmonary sarcoidosis, Clin. Mol. ALlergy, 13:16, 2015.*
(Continued)

*Primary Examiner* — Claire Kaufman
(74) *Attorney, Agent, or Firm* — Sterne, Kessler, Goldstein & Fox P.L.L.C.

(57) ABSTRACT

Recombinantly expressed variant antibodies that have enhanced affinity for TL1A and enhanced potency relative to the parent antibody from which they were derived are provided. The antibodies inhibit the interaction between TL1A and the death receptor 3 (DR3). The antibodies, or a composition thereof, may be used to treat one or more of asthma, COPD, pulmonary fibrosis, cystic fibrosis, inflammatory bowel disease, a gastrointestinal disease associated with cystic fibrosis, Crohn's disease, colitis, ulcerative colitis, irritable bowel syndrome, eosinophilic esophagitis, atopic dermatitis, eczema, scleroderma, arthritis, or rheumatoid arthritis.

31 Claims, 22 Drawing Sheets

Specification includes a Sequence Listing.

Related U.S. Application Data

(60) Provisional application No. 62/220,442, filed on Sep. 18, 2015.

(51) Int. Cl.
  *C07K 16/24* (2006.01)
  *A61P 37/06* (2006.01)
  *A61K 39/00* (2006.01)

(52) U.S. Cl.
  CPC ......... *A61K 2039/505* (2013.01); *A61P 37/06* (2018.01); *C07K 2317/21* (2013.01); *C07K 2317/33* (2013.01); *C07K 2317/565* (2013.01); *C07K 2317/76* (2013.01); *C07K 2317/92* (2013.01)

(56) References Cited

U.S. PATENT DOCUMENTS

| | | |
|---|---|---|
| 8,263,743 B2 | 9/2012 | Smith et al. |
| 8,642,741 B2 | 2/2014 | Classon et al. |
| 8,728,482 B2 | 5/2014 | Smith et al. |
| 9,017,679 B2 | 4/2015 | Podack et al. |
| 9,068,003 B2 | 6/2015 | Siegel et al. |
| 9,290,576 B2 | 3/2016 | Attinger et al. |
| 9,416,185 B2 | 8/2016 | Smith et al. |
| 9,556,277 B2 | 1/2017 | Classon et al. |
| 9,683,998 B2 | 6/2017 | Arch et al. |
| 10,138,296 B2 | 11/2018 | Poulton et al. |
| 2010/0190162 A1* | 7/2010 | Rotter ............... C07K 16/2875 435/6.16 |
| 2011/0217310 A1 | 9/2011 | Siegel et al. |
| 2012/0328559 A1 | 12/2012 | Podack et al. |
| 2014/0255302 A1 | 9/2014 | Poulton |
| 2014/0315250 A1 | 10/2014 | Smith et al. |
| 2016/0060335 A1 | 3/2016 | Shih et al. |
| 2016/0333104 A1 | 11/2016 | Poulton |

FOREIGN PATENT DOCUMENTS

| | | |
|---|---|---|
| WO | WO 2005/092927 A1 | 10/2005 |
| WO | WO 2006127900 A2 | 11/2006 |
| WO | WO 2007076465 A2 | 7/2007 |
| WO | WO2008/106451 A2 | 9/2008 |
| WO | WO 2008106451 A2 | 9/2008 |
| WO | WO 2009064854 A2 | 5/2009 |
| WO | WO2010/118210 A1 | 10/2010 |
| WO | WO 2011080314 A2 | 7/2011 |
| WO | WO 2012064682 A2 | 5/2012 |
| WO | WO 2012161856 A2 | 11/2012 |
| WO | WO 2013044298 A2 | 4/2013 |
| WO | WO 2014106602 A2 | 7/2014 |
| WO | WO 2014160883 A2 | 10/2014 |
| WO | WO2014/186665 A2 | 11/2014 |
| WO | WO2015/010108 A1 | 1/2015 |
| WO | WO2015/035261 A1 | 3/2015 |
| WO | WO 2015073580 A2 | 5/2015 |
| WO | WO-2016168750 A1 | 10/2016 |
| WO | WO 2017106383 A1 | 6/2017 |

OTHER PUBLICATIONS

Sela-Culang et al., The structural basis of antibody-antigen recognition, Frontiers Immuno. 4, article 302, pp. 1-13, 2013.*

Lamminmaki et al., "Chrystal Structure of A Recombinant Anti-Estradiol Fab Fragment In Complex With The 17beta-Estradiol," J Biol Chem 276:36687-94, American Society for Biochemistry and Molecular Biology (2001).

MacCallum et al., "Antibody-Antigen Interactions: Contact Analysis And Binding Site Topography," J Mol Biol 262:732-745, Elsevier, Netherlands (1996).

Van Rijt, L., et al., "Type 2 innate lymphoid cells: at the cross-roads in allergic asthma," Semin Immunopathol 38:483-496, Springer, Germany (Jul. 2016).

Aiba, Y., et al. "Systemic and local expression levels of TNF-like ligand 1A and its decoy receptor 3 are increased in primary biliary cirrhosis," Liver Int. 34(5):679-88 (2014).

Bamias, G., et al., High intestinal and systemic levels of decoy receptor 3 (DcR3) and its ligand TL1A in active ulcerative colitis, Clin Immunol 137(2):242-9 (2010).

Bamias, G., et al., "Expression, Localization, and Functional Activity of TL1A, a novel Th1-Polarizing Cytokine in Inflammatory Bowel Disease," J Immunol 171 (9):4868-74 (2003).

Bamias, G., et al., "Role of TL1A and its receptor DR3 in two models of chronic murine ileitis," Proc Natl Acad Sci USA 103(22):8441-6 (2006).

Bamias, G., et al., "Circulating levels of TNF-like cytokine 1A (TL1A) and its decoy receptor 3 (DcR3) in rheumatoid arthritis," Clin Immunol. 129(2):249-55 (2008).

Connelly, TM., et al., "The TNFSF15 Gene Single Nucleotide Polymorphism rs7848647 is Associated with Surgical Diverticulitis," Ann Surg 259(6):1132-7 (2014).

Czogalla, B., et al., "A meta-analysis of immunogenetic Case-Control Association Studies in irritable bowel syndrome," Neurogastroenterol Motil 27 (5):717-27 (May 2015).

Fang, L., et al., "Essential role of TNF receptor superfamily 25 (TNFRSF25) in the development of allergic lung inflammation," J Exp Med 205(5):1037-48 (2008).

Haritunians, T., et al., "Genetic predictors of medically refractory ulcerative colitis," Inflamm Bowel Dis 16(11):1830-40 (2010).

Hirano, A., et al., "Association study of 71 European Crohn's disease susceptibility loci in a Japanese population," Inflamm Bowel Dis 19 (3):526-33 (2013).

Jia, Y., et al., "IL-13+Type 2 innate lymphoid cells correlate with asthma control status and treatment response," Am J Respir Cell Mol Biol 55(5):675-683 (Jun. 2016).

Jones, GW., et al., "Naive and activated T cells display differential responsiveness to TL1A that affects Th17 generation, maintenance, and proliferation," FASEB J. 25(1):409-19 (2011).

Kakuta, Y., et al., "TNFSF15 transcripts from risk haplotype for Crohn's disease are overexpressed in stimulated T cells," Hum Mol Genet 18 (6):1089-98 (2009).

Kamada, N., et al., TL1A produced by lamina propria macrophages induces Th1 and Th17 immune responses in cooperation with IL-23 in patients with Crohn's disease, Inflamm Bowel Dis 16(4):568-75 (2010).

Kayamuro, H., et al., "TNF superfamily member, TL1A, is a potential mucosal vaccine adjuvant," Biochem Biophys Res Commun 384 (3):296-300 (2009).

Wolterink, R.G., et al., "Pulmonary innate lymphoid cells are major producers of IL-5 and IL-13 in murine models of allergic asthma," Eur J Immunol 42(5):1106-16 (2012).

Konsta, M., et al., "Increased levels of soluble TNF-like cytokine 1A in ankylosing spondylitis," Rheumatology (Oxford) 52(3):448-51 (2013).

Liu, JZ., et al., "Association analyses identify 38 susceptibility loci for inflammatory bowel disease and highlight shared genetic risk across populations," Nat Genet 47(9):979-86 (May 2015).

Meylan, F., et al., "The TNF-family receptor DR3 is essential for diverse T cell-mediated inflammatory diseases," Immunity 29(1):79-89 (2008).

Meylan, F., et al., "The TNF-family cytokine TL1A promotes allergic immunopathology through group 2 innate lymphoid cells," Mucosal Immunol 7(4):958-68 (2014).

Meylan, F., et al.,"TNF superfamily cytokines in the promotion of Th9 differentiation and immunopathology," Semin Immunopathol 39(1):21-2 (2017).

Meylan, F., et al., "The TNF-family cytokine TL1A drives IL-13-dependent small intestinal inflammation," Mucosal Immunol 4(2):172-85 (2011).

Michelsen, K.S., et al., "IBD-associated TL1A gene (TNFSF15) haplotypes determine increased expression of TL1A protein," PLoS One 4 (3):e4719 (2009).

(56) References Cited

OTHER PUBLICATIONS

Migone, T.S., et al., "TL1A is a TNF-like ligand for DR3 and IR6/DcR3 and functions as a T cell costimulatory," Immunity 16 (3):479-92 (2002).
Mjosberg, J.M., et al., "Human IL-25- and IL-33-responsive type 2 innate lymphoid cells are defined by expression of CRTH2 and CD 161," Nat Immunol 12 (11):1055-62 (2011).
Moffatt, M.F., et al.,"A large-scale, consortium-based genomewide association study of asthma," N Engl J Med 363 (13):1211-21 (2010).
Neill, D.R., et al., "Nuocytes represent a new innate effector leukocyte that mediates type-2 immunity," Nature 464 (7293): 1367-70 (2010).
Papadakis, K.A., et al., "TL1A synergizes with IL-12 and IL-18 to enhance IFN-gamma production in human T cells and NK cells," J Immunol 172 (11):7002-7 (2004).
Pappu, B.P., et al., "TL1A-DR3 interaction regulates Th17 cell function and Th17-mediated autoimmune disease," J Exp Med 205(5):1049-62 (2008).
Pedersen, A.E., et al., "Secretion, blood levels and cutaneous expression of TL1A in psoriasis patients," APMIS 123(7):547-55 (Feb. 2015).
Prehn, J.L., et al., "Potential role for TL1A, the new TNF-family member and potent costimulator of IFN-gamma, in mucosal inflammation," Clin Immunol 112 (1):66-77 (2004).
Richard, A.C., et al., "The TNF-famify ligand TL1A and its receptor DR3 promote T cell-mediated allergic immunopathology by enhancing differentiation and pathogenicity of IL-9-producing T cells," J Immunol 194(8):3567-82 (Feb. 2015).
Sampson, H.A., et al., "Second symposium on the definition and management of anaphylaxis: summary report—Second National Institute of Allergy and Infectious Disease/Food Allergy and Anaphylaxis Network symposium," J Allergy Clin Immunol. 117(2):391-7 (2006).
Screaton, G.R., et al., "LARD: a new lymphoid-specific death domain containing receptor regulated by alternative pre-mRNA splicing," Proc Natl Acad Sci USA 94(9):4615-9 (1997).
Shih, D.Q., et al., "Inhibition of a novel fibrogenic factor Tl1a reverses established colonic fibrosis," Mucosal Immunol 7(6):1492-503 (2014).
Soroosh, P., et al., "Th9 and allergic disease," Immunology 127(4):450-8 (2009).
Swan, C., et al., "Identifying and testing candidate genetic polymorphisms in the irritable bowel syndrome (IBS): association with TNFSF15 and TNFα," Gut 62 (7):985-94 (2013).
Takedatsu, H., et al., "TL1A (TNFSF15) regulates the development of chronic colitis by modulating both T-helper ($T_H$) 1 and $T_H$ 17 activation," Gastroenterology 135(2):552-67 (2008).
Thiebaut, R., et al., "TNFSF15 polymorphisms are associated with susceptibility to inflammatory bowel disease in a new European cohort," Am J Gastroenterol 104 (2):384-91 (2009).
Wen, L., et al.,"TL1 A-induced NF-kB activation and C-IAP2 production Prevent DR3-mediated apoptosis in TF-1 Cells," Journal of Biological Chemistry 278 (40):39251-39258 (2003).
Xu, W.D., et al., "Elevated plasma levels of TL1A in newly diagnosed systemic lupus erythematosus patients," Rheumatol Int. 35(8):1435-7 (May 2015).
Yamazaki, K., et al., "Single nucleotide polymorphisms in TNFSF15 confer susceptibility to Crohn's disease," Hum Mol Genet 14 (22):3499-506 (2005).
Yu, X., et al., "TNF superfamily member TL1A elicits type 2 innate lymphoid cells at mucosal barriers," Mucosal Immunol 7(3):730-40 (2014).
Zhang, J., et al., "Associations between TNFSF15 polymorphisms and susceptibility to ulcerative colitis and Crohn's disease: A meta-analysis," Autoimmunity 47(8):512-8 (2014).
Zucchelli, M., et al., "Association of TNFSF15 polymorphism with irritable bowel syndrome," Gut 60(12):1671-7 (2011).

Clarke AW, Poulton L, Shim D, Mabon D, Butt D, Pollard M, et al. An anti-TL1A antibody for the treatment of asthma and inflammatory bowel disease. mAbs 2018; 10(4):664-677. doi:10.1080/19420862.2018.1440164.
Singh RK, Perks WV, Twohig JP, Kidd EJ, Broadley K, Farrow SN, et al. Death receptor 3 regulates distinct pathological attributes of acute versus chronic murine allergic lung inflammation. Cell Immunol. 2017;320:62-70. doi:10.1016/j.cellimm.2017.09.005.
Huang, S-M., et al., "Therapeutic protein-drug interactions and implications for drug development," Clinical Pharmacology and Therapeutics 87:497-503 (2010).
Jin, T., et al., "X-ray crystal structure of TNF ligand family member TL1A at 2.1 A," Biochem Biophys Res Comm 364:1-6 (2007).
Vugmeyster, Y., et al.,"Pharmacokinetics and toxicology of therapeutic proteins: Advances and challenges," World J Biol Chem. 26;3(4):73-92 (2012).
Zhan, C., et al., "Decoy strategies: The structure of TL1A:DcR3 complex," Structure 19(2):162-171 (2011).
Agoram, BM., "Use of pharmacokinetic/ pharmacodynamic modelling for starting dose selection in first-in-human trials of high-risk biologies," Br J Clin Pharmacol. 67(2):153-60 (2008).
Sharma, V., et al., "To scale or not to scale: the principles of dose extrapolation," Br J Pharmacol. 157(6):907-21 (2009).
Zhao, L., et al., "Clinical pharmacology considerations in biologies development," Acta Pharmacol Sin. 33(11):1339-47 (2012).
Baker, DL., et al., "Evaluation of IgE Antibodies to Omalizumab (Xolair®) and Their Potential Correlation to Anaphylaxis," AAPS J. 18(1):115-23 (Jan. 2016).
Galant, SP., "The Evaluable Subject," Ann Allergy Asthma Immunol 79:173-5 (1997).
Leckie, M.J., et al., "Effects of an interleukin-5 blocking monoclonal antibody on eosinophils, airway hyper-responsiveness, and the late asthmatic response," Lancet 356:2144-8(2000).
Ma, L., et al., "Case fatality and population mortality associated with anaphylaxis in the United States," J Allergy Clin Immunol. 133(4):1075-83 (2014).
Woodcock, A., et al., "Efficacy and safety of fluticasone furoate/vilanterol compared with fluticasone propionate/salmeterol combination in adult and adolescent patients with persistent asthma: a randomized trial," Chest 144 (4);1222-9 (2013).
Bamias, G., et al., "Upregulation and nuclear localization of TNF-like Cytokine 1A (TL1A) and its receptors DR3 and DcR3 in psoriatic skin lesions," Experimental Dermatology 20:725-731 (2011).
Wang, W., et al., "Monoclonal antibody pharmacokinetics and pharmacodynamics," Clin Pharmacol Ther. 84(5):548-58 (2008).
Abdel-Razzak Z., et al. Cytokines down-regulate expression of major cytochrome P-450 enzymes in adult human hepatocytes in primary culture. Mol Pharmacol. 44(4):707-15 (1993).
Bamias, G., et al., "Differential expression of the TL1A/DcR3 system of TNF/TNFR-like proteins in large vs. small intestinal Crohn's disease," Dig Liver Dis. 44(1):30-6 (2012).
Diamant, Z., et al., "Setipiprant, a selective CRTH2 antagonist, reduces allergen-induced airway responses in allergic asthmatics," Clin Exp Allergy 44(8): 1044-52 (2014).
Xue, L., et al.,"Evaluation of pre-existing antibody presence as a risk factor for posttreatment antidrug antibody induction: analysis of human clinical study data for multiple biotherapeutics," AAPS J 15(3):893-6 (2013).
Franciosi, LG., et al., "Efficacy and safety of RPL554, a dual PDE3 and PDE4 inhibitor, in healthy volunteers and in patients with asthma or chronic obstructive pulmonary disease: findings from four clinical trials," Lancet Respir Med.1(9):714-27 (2013).
Girish, S., et al., "AAPS workshop report: strategies to address therapeutic protein-drug interactions during clinical development," AAPS J. 13(3):405-16 (2011).
Jover, R., et al., "Down-regulation of human CYP3A4 by the inflammatory signal interleukin-6: molecular mechanism and transcription factors involved," FASEB J. 16(13):1799-801 (2002).
Kim, H., et al., "Omalizumab: Practical considerations regarding the risk of anaphylaxis," Allergy Asthma Clin Immunol. 6(1):32 (2010).

(56) References Cited

OTHER PUBLICATIONS

Muntané-Relat, J., et al., "Differential effects of cytokines on the inducible expression of CYP1A1, CYP1A2, and CYP3A4 in human hepatocytes in primary culture," Hepatology 22(4 Pt 1):1143-53 (1995).
Shah, D.K., et al.,"Towards a platform PBPK model to characterize the plasma and tissue disposition of monoclonal antibodies in preclinical species and human," J Pharmacokinet Pharmacodyn. 39(1):67-86 (2012).
Shah RR, Morganroth J, Kleiman RB. ICH E14 Q&A(R2) document: commentary on the further updated recommendations on thorough QT studies. Br J Clin Pharmacol. 79(3):456-64 (Mar. 2015).
Tranter, E., et al.,"Giving monoclonal antibodies to healthy volunteers in phase 1 trials: is it safe?" Br J Clin Pharmacol. 76(2):164-72 (2013).
Vargas, HM, et al., Scientific review and recommendations on preclinical cardiovascular safety evaluation of biologics, J Pharmacol Toxicol Methods. 58(2):72-6 (2008).
Wenzel, S., et al., "Dupilumab in persistent asthma with elevated eosinophil levels," N Engl J Med. 27;368(26):2455-66 (2013).
Zhao, J., et al., "Across-Species Scaling of Monoclonal Antibody Pharmacokinetics Using a Minimal PBPK Model," PharmRes. 32(10):3269-81 (Oct. 2015).
Zidek, Z., et al., "Current status and challenges of cytokine pharmacology," Br J Pharmacol.157(3):342-61 (2009).
Clarke, A.W., et al., "An Anti-TL1A Antibody for the Treatment of Asthma and Inflammatory Bowel Disease," MAbs 1-14, Taylor & Francis, United States (Feb. 2018).
International Search Report and Written Opinion for International Application No. PCT/AU2012/001161, Australian Patent Office, Australia dated Dec. 10, 2012, 9 pages.
Yang, W.P., et al., "CDR Walking Mutagenesis for the Affinity Maturation of a Potent Human Anti-HIV-1 Antibody into the Picomolar Range," Journal of Molecular Biology 254(3):392-403, Elsevier, England (Dec. 1995).
International Search Report and Written Opinion issued in PCT/AU2011/001662.
Thie, "Affinity maturation by random mutagenesis and phage display", Antibody Engineering, vol. 1, Jan. 1, 2010, pp. 397-409.
Bayry, "TL 1A in the inflammatory network in autoimmune diseases", Nature Reviews, vol. 6, Feb. 2010, pp. 67-68.
Bull, et al., "The Death Receptor 3-TNF-Iike protein 1A pathway drives adverse bone pathology in inflammatory arthritis", J. Exp. Med., vol. 205, No. 11, 2008, pp. 2457-2464.
Chang, et al., "Affinity Maturation of an Epidermal Growth Factor Receptor Targeting Human Monoclonal Antibody ER414 by CDR Mutation", Immune Network, vol. 12, No. 4, Jan. 1, 2012, p. 155.
Chen, et al., "Enhancement and destruction of antibody function by somatic mutation: unequal occurrence is controlled by V gene combinatorial associations", The EMBO Journal, vol. 14, No. 12, 1995, pp. 2784-2794.
Daugherty, et al., "Quantitative analysis of the effect of the mutation frequency on the affinity maturation of single chain Fv antibodies", Proceedings of the National Academy of Sciences, vol. 97, No. 5, Feb. 29, 2000, pp. 2029-2034.
Migone, et al., "TL 1A is a TNF-Iike Ligand for DR3 and TR6/DcR3 and Functions as aT Cell Costimulator", Immunity, vol. 16, Mar. 2002, pp. 479-492.
Rajpal, et al., "A general method for greatly improving the affinity of antibodies by using combinatorial libraries", Proceedings of the National Academy of Sciences, vol. 102, No. 24, Jun. 1, 2005, pp. 8466-8471.
Steidl, et al., "In vitro affinity maturation of human GM-CSF antibodies by targeted CDR-diversification", Molecular Immunology, vol. 46, No. 1, Nov. 1, 2008, pp. 135-144.
Takedatsu, et al., TL 1A (TNFSF15) Regulates the Development of Chronic Colitis by Modulating Both T-Helper 1 and T-Helper17 Activation, Gastroenterology 2008, vol. 135, pp. 552-567.
Yang, et al., "Soluble decoy receptor 3 induces angiogenesis by neutralization of TL 1A, a cytokine belonging to tumor necrosis factor superfamily and exhibiting angiostatic action", Cancer Research, vol. 64, Feb. 1, 2004, pp. 1122-1129.
Zhan, et al., "Biochemical and Structural Characterization of the Human TL 1A Ectodomain", Biochemistry, vol. 48, 2009, pp. 7636-7645.
Zhan, et al., "Decoy Strategies: The Structure of TL 1A:DcR3 Complex", Structure, vol. 19, Feb. 9, 2011, pp. 162-171.
International Search Report and Written Opinion from PCT/US2016/052040.

* cited by examiner

QVQLVQSGAEVKKPGASVKVSCKAS GYTFTSYDIN WVRQAPGQGLEWMG WLNPSGNTGYAQKFQGRVTMTA
DRS

CDR1
AAAAAAAAA (SEQ ID NO:72)
SSSSSQSSSS (SEQ ID NO:73)
QQQQDQQQQ (SEQ ID NO:74)
DDDDDHDHDD (SEQ ID NO:75)
HHHHHKHKHH (SEQ ID NO:76)
KKKKKLKLKK (SEQ ID NO:77)
LLLLLWLLLL (SEQ ID NO:78)
WWWWWYWYWW (SEQ ID NO:79)
YYY                     Y

CDR2
AAAAAAAAAAS (SEQ ID NO:80)
SSSSSQSSSSQ (SEQ ID NO:81)
QQQQDQQQQQD (SEQ ID NO:82)
DDDDHDHDDDH (SEQ ID NO:83)
HHHHKHKHHHK (SEQ ID NO:84)
KKKKLKLKKKL (SEQ ID NO:85)
LWLLLWLLLLW (SEQ ID NO:86)
YYWWWWWWWWY (SEQ ID NO:87)
YYY       YYYY (SEQ ID NO:88)

(SEQ ID NO:1)

TSTAYMELSSLRSEDTAVYYCAR EVPETAAFEY WGQGTLVTVSS

CDR3

FIG. 1

QSVLTQPPSVSGAPGQRVTISC TSSSSDIGAGLGVH WYQQLPGTAPKLLIE GYYNRPS GVPDRFSGSKSGTS
ASL

CDR1: TSSSSDIGAGLGVH

CDR2: GYYNRPS

```
AAAAAAASAAAAA  (SEQ ID NO:89)
SQQQSSSQSSSSS  (SEQ ID NO:90)
QDDDDQQQDQQQQ  (SEQ ID NO:91)
DHHHHDDHDDDDD  (SEQ ID NO:92)
HKKKKHHKHHHHH  (SEQ ID NO:93)
KLLLLKKLKKKKK  (SEQ ID NO:94)
LWWWWLLWLWLLL  (SEQ ID NO:95)
WYYYYWYWYWWWW  (SEQ ID NO:96)
              Y  YYY
```

TITGLLPEDEGDYC QSYDGTLSALF GGGTKLTVLG    (SEQ ID NO:2)

CDR3: QSYDGTLSALF

```
AAAAAAASA  (SEQ ID NO:97)
SQSSSSSQQS  (SEQ ID NO:98)
DDQQQQQDDQ  (SEQ ID NO:99)
HHDHDDDHHD  (SEQ ID NO:100)
KKHKHHHKKH  (SEQ ID NO:101)
LLKLKKKLLK  (SEQ ID NO:102)
WWLWLLWWWW  (SEQ ID NO:103)
YYWYWYWYYY  (SEQ ID NO:104)
     F   YY
```

```
                 10        20        30        40        50        60
            ....|....|....|....|....|....|....|....|....|....|....|....|....
179VH       QVQLVQSGAEVKKPGASVKVSCKASGYTFTSYDINWVRQAPGQGLEWMGWLNPNSGNTGYAQKFQGRVT
267VH       ................................................................
277VH       ................................................................
278VH       ................................................................
307VH       ................................................................
331VH       ................................................................
547VH       ...........................................................Y....
583VH       ................................................................
584VH       ................................................................
585VH       ................................................................
586VH       ................................................................
587VH       ...........................................................Y....
591VH       ...........................................................Y....
592VH       ...........................................................Y....
593VH       ...........................................................Y....
594VH       ...........................................................Y....
595VH       ...........................................................Y....
601VH       ...........................................................Y....

70        80        90       100       110
            |....|....|....|....|....|....|....|....|....|....
179VH       MTADRSTSTAYMELSSLRSEDTAVYYCAREVPETAAFEYWGQGTLVTVSS     SEQ ID NO:1
267VH       .................................................     SEQ ID NO:1
277VH       .................................................     SEQ ID NO:1
278VH       .................................................     SEQ ID NO:1
307VH       .................................................     SEQ ID NO:1
331VH       .................................................     SEQ ID NO:1
547VH       .................................................     SEQ ID NO:3
583VH       .................................................     SEQ ID NO:1
584VH       .................................................     SEQ ID NO:1
585VH       .................................................     SEQ ID NO:1
586VH       .................................................     SEQ ID NO:1
587VH       .................................................     SEQ ID NO:3
591VH       .................................................     SEQ ID NO:3
592VH       .................................................     SEQ ID NO:3
593VH       .................................................     SEQ ID NO:3
594VH       .................................................     SEQ ID NO:3
595VH       .................................................     SEQ ID NO:3
601VH       .................................................     SEQ ID NO:3
```

FIGURE 3

```
                10        20        30        40        50        60
            ....|....|....|....|....|....|....|....|....|....|....|....|
179VL       QSVLTQPPSVSGAPGQRVTISCTSSSSDIGAGLGVHWYQQLPGTAPKLLIEGYYNRPSGVPDRFS
267VL       ...........................A.....................................
277VL       ...........................S.....................................
278VL       ...........................Q.....................................
307VL       .....................................L...........................
331VL       ..................................................................
547VL       ..................................................................
583VL       ...........................A.....................................
584VL       ...........................S.....................................
585VL       ...........................Q.....................................
586VL       .....................................L...........................
587VL       ..................................................................
591VL       .....................................L...........................
592VL       ...........................A.....................................
593VL       ...........................S.....................................
594VL       ...........................Q.....................................
595VL       .....................................L...........................
601VL       ..................................................................

70        80        90       100       110
            ....|....|....|....|....|....|....|....|....|.
179VL       GTSASLTITGLLPEDEGDYYCQSYDGTLSALFGGGTKLTVLG      SEQ ID NO:2
267VL       .............................................  SEQ ID NO:11
277VL       .............................................  SEQ ID NO:12
278VL       .............................................  SEQ ID NO:13
307VL       .............................................  SEQ ID NO:9
331VL       .....................W.......................  SEQ ID NO:4
547VL       .............................................  SEQ ID NO:2
583VL       .....................W.......................  SEQ ID NO:5
584VL       .....................W.......................  SEQ ID NO:6
585VL       .....................W.......................  SEQ ID NO:7
586VL       .....................W.......................  SEQ ID NO:8
587VL       .....................W.......................  SEQ ID NO:4
591VL       .....................W.......................  SEQ ID NO:9
592VL       .....................W.......................  SEQ ID NO:5
593VL       .....................W.......................  SEQ ID NO:6
594VL       .....................W.......................  SEQ ID NO:7
595VL       .....................W.......................  SEQ ID NO:8
601VL       .....................F.......................  SEQ ID NO:10
```

FIGURE 4

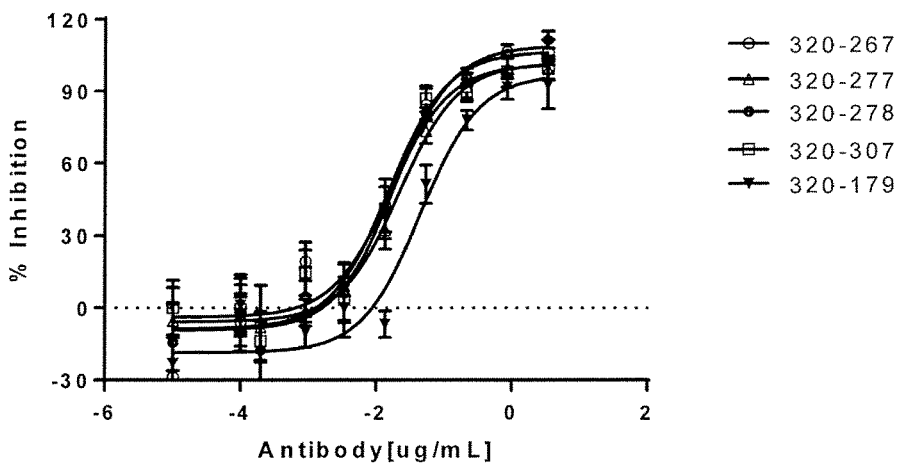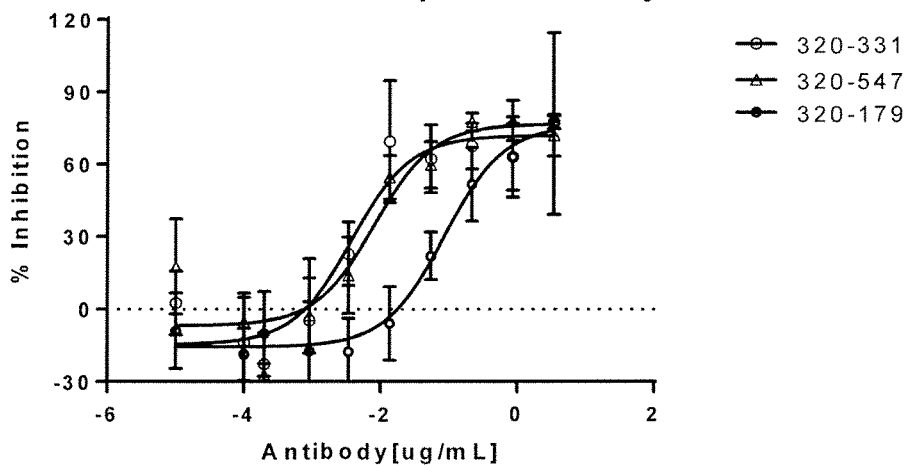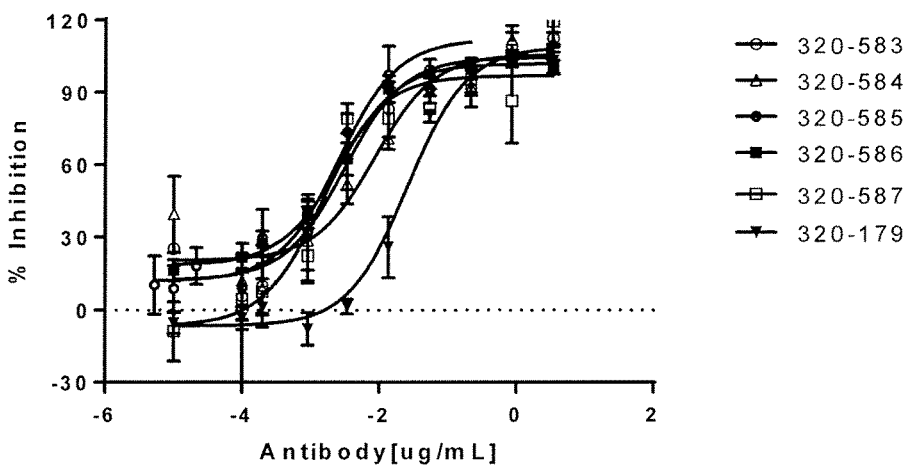
FIGURE 6

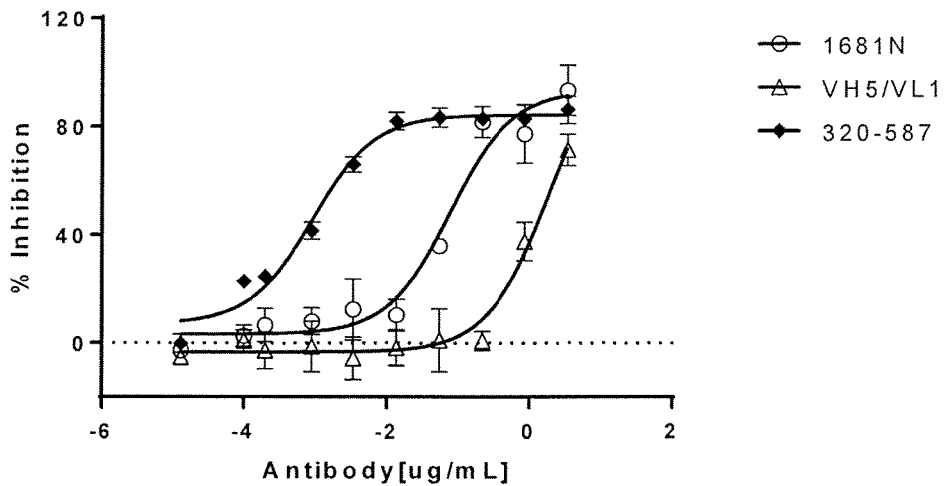
| Antibody | IC-50 (ug/mL) | Fold Improvement of 320-587 |
|---|---|---|
| 320-587 | 0.00091 | |
| 1681N | 0.077 | 85 |
| VH5/VL1 | 1.876 | 2062 |
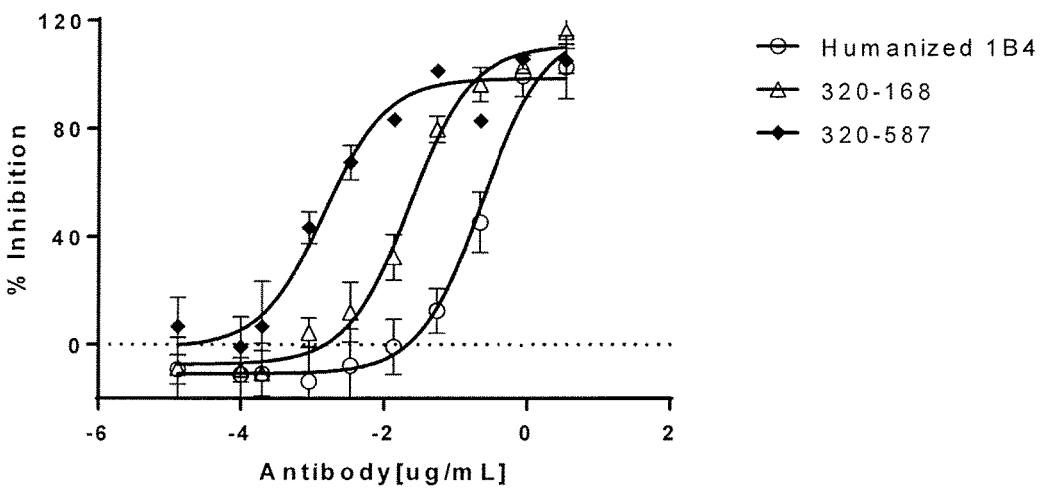
| Antibody | IC-50 (ug/mL) | Fold Improvement of 320-587 |
|---|---|---|
| 320-587 | 0.0015 | |
| 320-168 | 0.023 | 15.3 |
| VH5/VL1 | 0.23 | 153 |
FIGURE 8

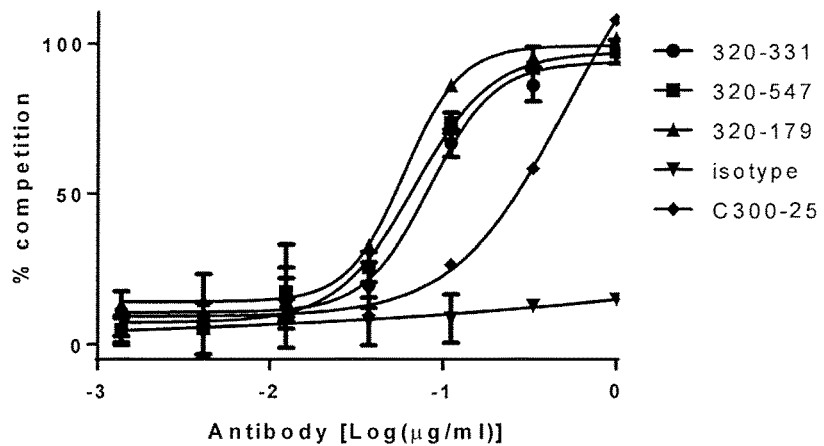
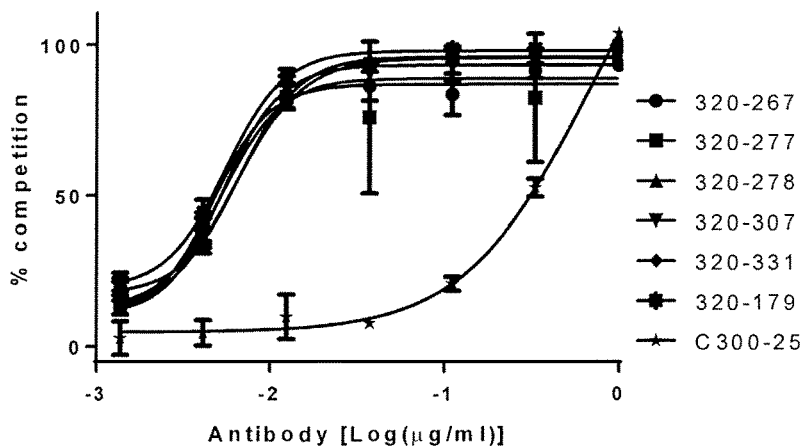
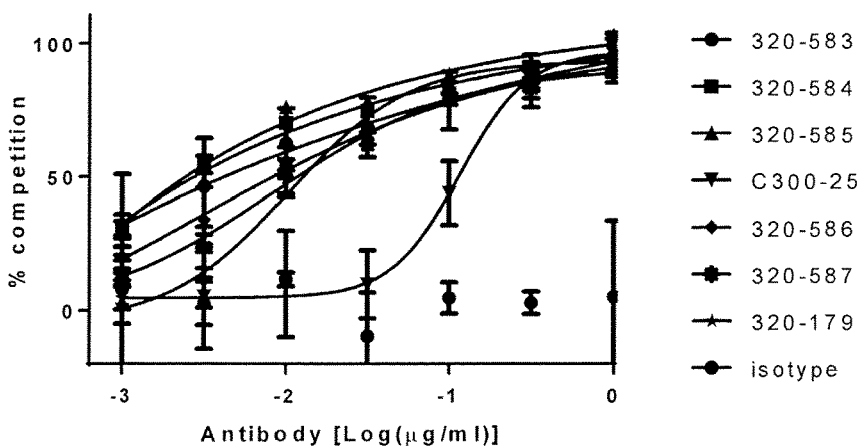
FIGURE 9

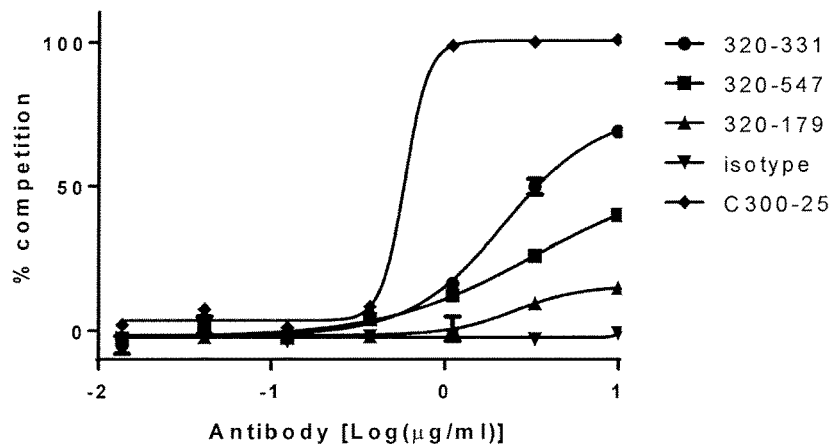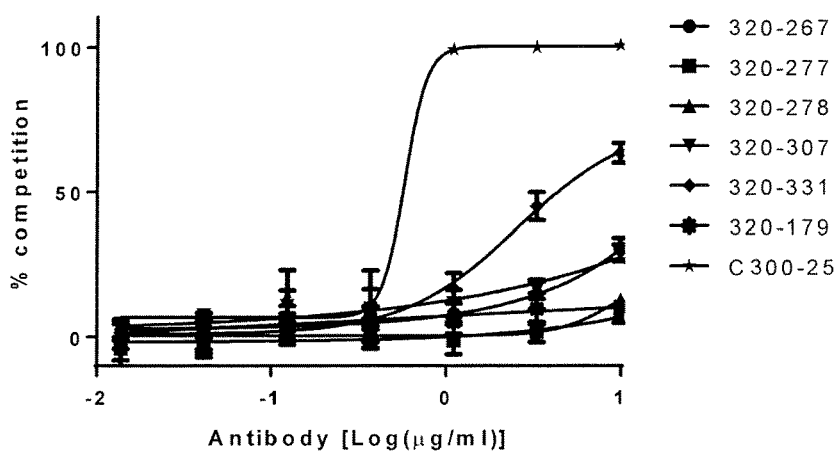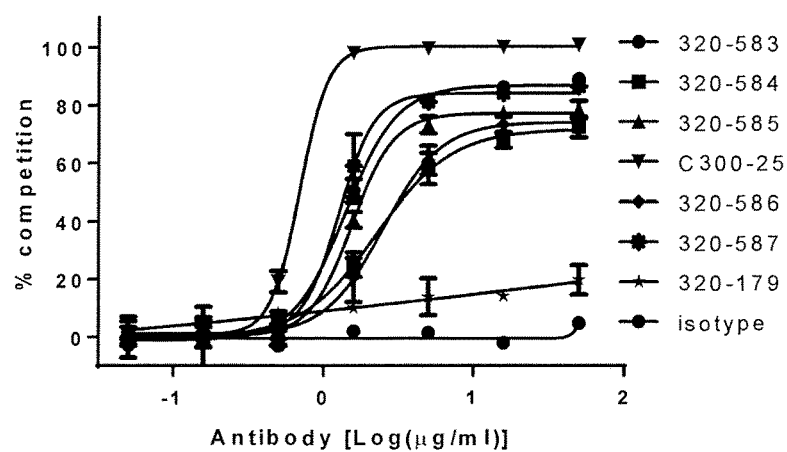
FIGURE 10

SEQUENCE LISTING

<160> NUMBER OF SEQ ID NOS: 104

<210> SEQ ID NO 1

```
<211> LENGTH: 119
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Asn Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser
        115

<210> SEQ ID NO 2
<211> LENGTH: 111
<212> TYPE: PRT
<213> ORGANISM: Homo sapiens

<400> SEQUENCE: 2

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110

<210> SEQ ID NO 3
<211> LENGTH: 119
<212> TYPE: PRT
<213> ORGANISM: Homo sapiens

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
    50                  55                  60
```

```
Gln Gly Arg Val Thr Met Thr Ala Asp Arg Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Val Pro Glu Thr Ala Ala Phe Glu Tyr Trp Gly Gln Gly
            100                 105                 110

Thr Leu Val Thr Val Ser Ser
            115

<210> SEQ ID NO 4
<211> LENGTH: 111
<212> TYPE: PRT
<213> ORGANISM: Homo sapiens

<400> SEQUENCE: 4

Gln Ser Val Leu Thr Gln Pro Pro Ser Val Ser Gly Ala Pro Gly Gln
  1               5                  10                  15

Arg Val Thr Ile Ser Cys Thr Ser Ser Ser Asp Ile Gly Ala Gly
             20                  25                  30

Leu Gly Val His Trp Tyr Gln Gln Leu Pro Gly Thr Ala Pro Lys Leu
             35                  40                  45

Leu Ile Glu Gly Tyr Tyr Asn Arg Pro Ser Gly Val Pro Asp Arg Phe
 50                  55                  60

Ser Gly Ser Lys Ser Gly Thr Ser Ala Ser Leu Thr Ile Thr Gly Leu
 65                  70                  75                  80

Leu Pro Glu Asp Glu Gly Asp Tyr Tyr Cys Gln Ser Trp Asp Gly Thr
             85                  90                  95

Leu Ser Ala Leu Phe Gly Gly Gly Thr Lys Leu Thr Val Leu Gly
            100                 105                 110

<210> SEQ ID NO 5
<211> LENGTH: 111
<212> TYPE: PRT
<213> ORGANISM: Homo sapiens

<400> SEQUENCE: 5

Gln Ser Val Leu Thr Gln Pro Pro Ser Val Ser Gly Ala Pro Gly Gln
  1               5                  10                  15

Arg Val Thr Ile Ser Cys Thr Ser Ser Ser Asp Ile Gly Ala Ala
             20                  25                  30

Leu Gly Val His Trp Tyr Gln Gln Leu Pro Gly Thr Ala Pro Lys Leu
             35                  40                  45

Leu Ile Glu Gly Tyr Tyr Asn Arg Pro Ser Gly Val Pro Asp Arg Phe
 50                  55                  60

Ser Gly Ser Lys Ser Gly Thr Ser Ala Ser Leu Thr Ile Thr Gly Leu
 65                  70                  75                  80

Leu Pro Glu Asp Glu Gly Asp Tyr Tyr Cys Gln Ser Trp Asp Gly Thr
             85                  90                  95

Leu Ser Ala Leu Phe Gly Gly Gly Thr Lys Leu Thr Val Leu Gly
            100                 105                 110

<210> SEQ ID NO 6
<211> LENGTH: 111
<212> TYPE: PRT
<213> ORGANISM: Homo sapiens

<400> SEQUENCE: 6

Gln Ser Val Leu Thr Gln Pro Pro Ser Val Ser Gly Ala Pro Gly Gln
  1               5                  10                  15
```

-continued

```
                 1               5                  10                  15
            Arg Val Thr Ile Ser Cys Thr Ser Ser Ser Asp Ile Gly Ala Gly
                         20                  25                  30

Ser Gly Val His Trp Tyr Gln Gln Leu Pro Gly Thr Ala Pro Lys Leu
                         35                  40                  45

Leu Ile Glu Gly Tyr Tyr Asn Arg Pro Ser Gly Val Pro Asp Arg Phe
             50                  55                  60

Ser Gly Ser Lys Ser Gly Thr Ser Ala Ser Leu Thr Ile Thr Gly Leu
             65                  70                  75                  80

Leu Pro Glu Asp Glu Gly Asp Tyr Tyr Cys Gln Ser Trp Asp Gly Thr
                             85                  90                  95

Leu Ser Ala Leu Phe Gly Gly Gly Thr Lys Leu Thr Val Leu Gly
                        100                 105                 110
```

<210> SEQ ID NO 7
<211> LENGTH: 111
<212> TYPE: PRT
<213> ORGANISM: Homo sapiens

<400> SEQUENCE: 7

```
            Gln Ser Val Leu Thr Gln Pro Pro Ser Val Ser Gly Ala Pro Gly Gln
             1               5                  10                  15

Arg Val Thr Ile Ser Cys Thr Ser Ser Ser Asp Ile Gly Ala Gly
                         20                  25                  30

Gly Gly Val His Trp Tyr Gln Gln Leu Pro Gly Thr Ala Pro Lys Leu
                         35                  40                  45

Leu Ile Glu Gly Tyr Tyr Asn Arg Pro Ser Gly Val Pro Asp Arg Phe
             50                  55                  60

Ser Gly Ser Lys Ser Gly Thr Ser Ala Ser Leu Thr Ile Thr Gly Leu
             65                  70                  75                  80

Leu Pro Glu Asp Glu Gly Asp Tyr Tyr Cys Gln Ser Trp Asp Gly Thr
                             85                  90                  95

Leu Ser Ala Leu Phe Gly Gly Gly Thr Lys Leu Thr Val Leu Gly
                        100                 105                 110
```

<210> SEQ ID NO 8
<211> LENGTH: 111
<212> TYPE: PRT
<213> ORGANISM: Homo sapiens

<400> SEQUENCE: 8

```
            Gln Ser Val Leu Thr Gln Pro Pro Ser Val Ser Gly Ala Pro Gly Gln
             1               5                  10                  15

Arg Val Thr Ile Ser Cys Thr Ser Ser Ser Asp Ile Gly Ala Gly
                         20                  25                  30

Leu Gly Val Leu Trp Tyr Gln Gln Leu Pro Gly Thr Ala Pro Lys Leu
                         35                  40                  45

Leu Ile Glu Gly Tyr Tyr Asn Arg Pro Ser Gly Val Pro Asp Arg Phe
             50                  55                  60

Ser Gly Ser Lys Ser Gly Thr Ser Ala Ser Leu Thr Ile Thr Gly Leu
             65                  70                  75                  80

Leu Pro Glu Asp Glu Gly Asp Tyr Tyr Cys Gln Ser Trp Asp Gly Thr
                             85                  90                  95

Leu Ser Ala Leu Phe Gly Gly Gly Thr Lys Leu Thr Val Leu Gly
                        100                 105                 110
```

<210> SEQ ID NO 9
<211> LENGTH: 111
<212> TYPE: PRT
<213> ORGANISM: Homo sapiens

<400> SEQUENCE: 9

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Leu Gly Val Leu Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110

<210> SEQ ID NO 10
<211> LENGTH: 111
<212> TYPE: PRT
<213> ORGANISM: Homo sapiens

<400> SEQUENCE: 10

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Phe Asp Gly Thr
                85                  90                  95

Leu Ser Ala Leu Phe Gly Gly Gly Thr Lys Leu Thr Val Leu Gly
            100                 105                 110

<210> SEQ ID NO 11
<211> LENGTH: 111
<212> TYPE: PRT
<213> ORGANISM: Homo sapiens

<400> SEQUENCE: 11

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Ala
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110

<210> SEQ ID NO 12
<211> LENGTH: 111
<212> TYPE: PRT
<213> ORGANISM: Homo sapiens

<400> SEQUENCE: 12

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Ser Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110

<210> SEQ ID NO 13
<211> LENGTH: 111
<212> TYPE: PRT
<213> ORGANISM: Homo sapiens

<400> SEQUENCE: 13

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Gln Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Tyr Asp Gly Thr
                85                  90                  95

Leu Ser Ala Leu Phe Gly Gly Gly Thr Lys Leu Thr Val Leu Gly
            100                 105                 110

<210> SEQ ID NO 14
<211> LENGTH: 111
<212> TYPE: PRT
<213> ORGANISM: Homo sapiens
<220> FEATURE:
<221> NAME/KEY: Xaa
<222> LOCATION: (32)..(32)
<223> OTHER INFORMATION: G or A
<220> FEATURE:
<221> NAME/KEY: Xaa
<222> LOCATION: (33)..(33)
<223> OTHER INFORMATION: L or S or Q
<220> FEATURE:

```
<221> NAME/KEY: Xaa
<222> LOCATION: (36)..(36)
<223> OTHER INFORMATION: H or L
<220> FEATURE:
<221> NAME/KEY: Xaa
<222> LOCATION: (93)..(93)
<223> OTHER INFORMATION: Y or F or W

<400> SEQUENCE: 14

Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Xaa
            20                  25                  30

Xaa Gly Val Xaa Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Xaa Asp Gly Thr
                85                  90                  95

Leu Ser Ala Leu Phe Gly Gly Gly Thr Lys Leu Thr Val Leu Gly
            100                 105                 110

<210> SEQ ID NO 15
<211> LENGTH: 10
<212> TYPE: PRT
<213> ORGANISM: Homo sapiens

<400> SEQUENCE: 15

Gly Tyr Thr Phe Thr Ser Tyr Asp Ile Asn
1               5                   10

<210> SEQ ID NO 16
<211> LENGTH: 10
<212> TYPE: PRT
<213> ORGANISM: Homo sapiens

<400> SEQUENCE: 16

Trp Leu Asn Pro Asn Ser Gly Asn Thr Gly
1               5                   10

<210> SEQ ID NO 17
<211> LENGTH: 10
<212> TYPE: PRT
<213> ORGANISM: Homo sapiens

<400> SEQUENCE: 17

Glu Val Pro Glu Thr Ala Ala Phe Glu Tyr
1               5                   10

<210> SEQ ID NO 18
<211> LENGTH: 14
<212> TYPE: PRT
<213> ORGANISM: Homo sapiens

<400> SEQUENCE: 18

Thr Ser Ser Ser Ser Asp Ile Gly Ala Gly Leu Gly Val His
1               5                   10

<210> SEQ ID NO 19
<211> LENGTH: 7
<212> TYPE: PRT
```

<213> ORGANISM: Homo sapiens

<400> SEQUENCE: 19

Gly Tyr Tyr Asn Arg Pro Ser
1               5

<210> SEQ ID NO 20
<211> LENGTH: 10
<212> TYPE: PRT
<213> ORGANISM: Homo sapiens

<400> SEQUENCE: 20

Gln Ser Tyr Asp Gly Thr Leu Ser Ala Leu
1               5                   10

<210> SEQ ID NO 21
<211> LENGTH: 10
<212> TYPE: PRT
<213> ORGANISM: Homo sapiens

<400> SEQUENCE: 21

Trp Leu Asn Pro Asn Ser Gly Tyr Thr Gly
1               5                   10

<210> SEQ ID NO 22
<211> LENGTH: 10
<212> TYPE: PRT
<213> ORGANISM: Homo sapiens

<400> SEQUENCE: 22

Gln Ser Trp Asp Gly Thr Leu Ser Ala Leu
1               5                   10

<210> SEQ ID NO 23
<211> LENGTH: 14
<212> TYPE: PRT
<213> ORGANISM: Homo sapiens

<400> SEQUENCE: 23

Thr Ser Ser Ser Ser Asp Ile Gly Ala Ala Leu Gly Val His
1               5                   10

<210> SEQ ID NO 24
<211> LENGTH: 14
<212> TYPE: PRT
<213> ORGANISM: Homo sapiens

<400> SEQUENCE: 24

Thr Ser Ser Ser Ser Asp Ile Gly Ala Gly Ser Gly Val His
1               5                   10

<210> SEQ ID NO 25
<211> LENGTH: 14
<212> TYPE: PRT
<213> ORGANISM: Homo sapiens

<400> SEQUENCE: 25

Thr Ser Ser Ser Ser Asp Ile Gly Ala Gly Gln Gly Val His
1               5                   10

<210> SEQ ID NO 26
<211> LENGTH: 14
<212> TYPE: PRT
<213> ORGANISM: Homo sapiens

```
<400> SEQUENCE: 26

Thr Ser Ser Ser Ser Asp Ile Gly Ala Gly Leu Gly Val Leu
1               5                   10

<210> SEQ ID NO 27
<211> LENGTH: 10
<212> TYPE: PRT
<213> ORGANISM: Homo sapiens

<400> SEQUENCE: 27

Gln Ser Phe Asp Gly Thr Leu Ser Ala Leu
1               5                   10

<210> SEQ ID NO 28
<211> LENGTH: 10
<212> TYPE: PRT
<213> ORGANISM: Homo sapiens
<220> FEATURE:
<221> NAME/KEY: Xaa
<222> LOCATION: (8)..(8)
<223> OTHER INFORMATION: N or Y

<400> SEQUENCE: 28

Trp Leu Asn Pro Asn Ser Gly Xaa Thr Gly
1               5                   10

<210> SEQ ID NO 29
<211> LENGTH: 14
<212> TYPE: PRT
<213> ORGANISM: Homo sapiens
<220> FEATURE:
<221> NAME/KEY: Xaa
<222> LOCATION: (10)..(10)
<223> OTHER INFORMATION: G or A
<220> FEATURE:
<221> NAME/KEY: Xaa
<222> LOCATION: (11)..(11)
<223> OTHER INFORMATION: L or S or Q
<220> FEATURE:
<221> NAME/KEY: Xaa
<222> LOCATION: (14)..(14)
<223> OTHER INFORMATION: H or L

<400> SEQUENCE: 29

Thr Ser Ser Ser Ser Asp Ile Gly Ala Xaa Xaa Gly Val Xaa
1               5                   10

<210> SEQ ID NO 30
<211> LENGTH: 10
<212> TYPE: PRT
<213> ORGANISM: Homo sapiens
<220> FEATURE:
<221> NAME/KEY: Xaa
<222> LOCATION: (3)..(3)
<223> OTHER INFORMATION: Y or W or F

<400> SEQUENCE: 30

Gln Ser Xaa Asp Gly Thr Leu Ser Ala Leu
1               5                   10

<210> SEQ ID NO 31
<211> LENGTH: 180
<212> TYPE: PRT
<213> ORGANISM: Homo sapiens

<400> SEQUENCE: 31

Leu Lys Gly Gln Glu Phe Ala Pro Ser His Gln Gln Val Tyr Ala Pro
1               5                   10                  15
```

Leu Arg Ala Asp Gly Asp Lys Pro Arg Ala His Leu Thr Val Val Arg
            20                  25                  30

Gln Thr Pro Thr Gln His Phe Lys Asn Gln Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Leu Ile Pro Glu Ser Gly Asp Tyr Phe Ile Tyr Ser
65                  70                  75                  80

Gln Val Thr Phe Arg Gly Met Thr Ser Glu Cys Ser Glu Ile Arg Gln
                85                  90                  95

Ala Gly Arg Pro Asn Lys Pro Asp Ser Ile Thr Val Val Ile Thr Lys
            100                 105                 110

Val Thr Asp Ser Tyr Pro Glu Pro Thr Gln Leu Leu Met Gly Thr Lys
        115                 120                 125

Ser Val Cys Glu Val Gly Ser Asn Trp Phe Gln Pro Ile Tyr Leu Gly
    130                 135                 140

Ala Met Phe Ser Leu Gln Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180

<210> SEQ ID NO 32
<211> LENGTH: 180
<212> TYPE: PRT
<213> ORGANISM: Homo sapiens

<400> SEQUENCE: 32

Leu Lys Gly Gln Glu Phe Ala Pro Ser His Gln Gln Val Tyr Ala Pro
1               5                   10                  15

Leu Arg Ala Asp Gly Asp Lys Pro Arg Ala His Leu Thr Val Val Arg
            20                  25                  30

Gln Thr Pro Thr Gln His Phe Lys Asn Gln Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Leu Ile Pro Glu Ser Gly Asp Tyr Phe Ile Tyr Ser
65                  70                  75                  80

Gln Val Thr Phe Ala Gly Met Thr Ser Glu Cys Ser Glu Ile Arg Gln
                85                  90                  95

Ala Gly Arg Pro Asn Lys Pro Asp Ser Ile Thr Val Val Ile Thr Lys
            100                 105                 110

Val Thr Asp Ser Tyr Pro Glu Pro Thr Gln Leu Leu Met Gly Thr Lys
        115                 120                 125

Ser Val Cys Glu Val Gly Ser Asn Trp Phe Gln Pro Ile Tyr Leu Gly
    130                 135                 140

Ala Met Phe Ser Leu Gln Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180

```
<210> SEQ ID NO 33
<211> LENGTH: 210
<212> TYPE: PRT
<213> ORGANISM: Homo sapiens

<400> SEQUENCE: 33
```

Asp Tyr Lys Asp Asp Asp Lys Gly Ser His His His His His
1               5                   10                  15

His His Gly Ser Gly Ser Leu Val Pro Arg Gly Ser Gly Ser Leu Lys
            20                  25                  30

Gly Gln Glu Phe Ala Pro Ser His Gln Gln Val Tyr Ala Pro Leu Arg
        35                  40                  45

Ala Asp Gly Asp Lys Pro Arg Ala His Leu Thr Val Val Arg Gln Thr
    50                  55                  60

Pro Thr Gln His Phe Lys Asn Gln Phe Pro Ala Leu His Trp Glu His
65                  70                  75                  80

Glu Leu Gly Leu Ala Phe Thr Lys Asn Arg Met Asn Tyr Thr Asn Lys
                85                  90                  95

Phe Leu Leu Ile Pro Glu Ser Gly Asp Tyr Phe Ile Tyr Ser Gln Val
            100                 105                 110

Thr Phe Arg Gly Met Thr Ser Glu Cys Ser Glu Ile Arg Gln Ala Gly
        115                 120                 125

Arg Pro Asn Lys Pro Asp Ser Ile Thr Val Val Ile Thr Lys Val Thr
130                 135                 140

Asp Ser Tyr Pro Glu Pro Thr Gln Leu Leu Met Gly Thr Lys Ser Val
145                 150                 155                 160

Cys Glu Val Gly Ser Asn Trp Phe Gln Pro Ile Tyr Leu Gly Ala Met
                165                 170                 175

Phe Ser Leu Gln Glu Gly Asp Lys Leu Met Val Asn Val Ser Asp Ile
            180                 185                 190

Ser Leu Val Asp Tyr Thr Lys Glu Asp Lys Thr Phe Phe Gly Ala Phe
        195                 200                 205

Leu Leu
    210

```
<210> SEQ ID NO 34
<211> LENGTH: 180
<212> TYPE: PRT
<213> ORGANISM: Macaca fascicularis

<400> SEQUENCE: 34
```

Leu Lys Gly Gln Glu Phe Ala Pro Ser His Gln Gln Val Tyr Ala Pro
1               5                   10                  15

Leu Arg Ala Asp Gly Asp Lys Pro Arg Ala His Leu Thr Val Val Arg
            20                  25                  30

Gln Thr Pro Thr Gln His Leu Lys Asn Gln Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Leu Ile Pro Glu Ser Gly Asp Tyr Phe Val Tyr Ser
65                  70                  75                  80

Gln Val Thr Phe Arg Gly Met Thr Ser Glu Cys Ser Glu Ile Arg Gln
                85                  90                  95

Ala Gly Arg Pro Asn Lys Pro Asp Ser Ile Thr Val Val Ile Thr Lys
            100                 105                 110

Val Thr Asp Ser Tyr Pro Glu Pro Thr Gln Leu Leu Met Gly Thr Lys

```
                    115                 120                 125
Ser Val Cys Glu Val Gly Ser Asn Trp Phe Gln Pro Ile Tyr Leu Gly
    130                 135                 140

Ala Met Phe Ser Leu Gln Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180

<210> SEQ ID NO 35
<211> LENGTH: 180
<212> TYPE: PRT
<213> ORGANISM: Mus musculus

<400> SEQUENCE: 35

Leu Arg Ala Ile Thr Glu Glu Arg Ser Glu Pro Ser Pro Gln Gln Val
1               5                   10                  15

Tyr Ser Pro Pro Arg Gly Lys Pro Arg Ala His Leu Thr Ile Lys Lys
                20                  25                  30

Gln Thr Pro Ala Pro His Leu Lys Asn Gln Leu Ser Ala Leu His Trp
            35                  40                  45

Glu His Asp Leu Gly Met Ala Phe Thr Lys Asn Gly Met Lys Tyr Ile
        50                  55                  60

Asn Lys Ser Leu Val Ile Pro Glu Ser Gly Asp Tyr Phe Ile Tyr Ser
65                  70                  75                  80

Gln Ile Thr Phe Arg Gly Thr Thr Ser Val Cys Gly Asp Ile Ser Arg
                85                  90                  95

Gly Arg Arg Pro Asn Lys Pro Asp Ser Ile Thr Met Val Ile Thr Lys
            100                 105                 110

Val Ala Asp Ser Tyr Pro Glu Pro Ala Arg Leu Leu Thr Gly Ser Lys
        115                 120                 125

Ser Val Cys Glu Ile Ser Asn Asn Trp Phe Gln Ser Leu Tyr Leu Gly
    130                 135                 140

Ala Thr Phe Ser Leu Glu Glu Gly Asp Arg Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180

<210> SEQ ID NO 36
<211> LENGTH: 180
<212> TYPE: PRT
<213> ORGANISM: Rattus norvegicus

<400> SEQUENCE: 36

Phe Pro Thr Val Thr Glu Glu Arg Ser Ala Pro Ser Ala Gln Pro Val
1               5                   10                  15

Tyr Thr Pro Ser Arg Asp Lys Pro Lys Ala His Leu Thr Ile Met Arg
                20                  25                  30

Gln Thr Pro Val Pro His Leu Lys Asn Glu Leu Ala Ala Leu His Trp
            35                  40                  45

Glu Asn Asn Leu Gly Met Ala Phe Thr Lys Asn Arg Met Asn Tyr Thr
        50                  55                  60

Asn Lys Phe Leu Val Ile Pro Glu Ser Gly Asp Tyr Phe Ile Tyr Ser
```

-continued

```
                65                  70                  75                  80
Gln Ile Thr Phe Arg Gly Thr Thr Ser Glu Cys Gly Asp Ile Ser Arg
                    85                  90                  95

Val Arg Arg Pro Lys Lys Pro Asp Ser Ile Thr Val Ile Thr Lys
                100                 105                 110

Val Ala Asp Ser Tyr Pro Glu Pro Ala His Leu Leu Thr Gly Thr Lys
                115                 120                 125

Ser Val Cys Glu Ile Ser Ser Asn Trp Phe Gln Pro Ile Tyr Leu Gly
                130                 135                 140

Ala Met Phe Ser Leu Glu Glu Gly Asp Arg Leu Met Val Asn Val Ser
145                 150                 155                 160

Asp Ile Ser Leu Val Asp Tyr Thr Lys Glu Asp Lys Thr Phe Phe Gly
                    165                 170                 175

Ala Phe Leu Ile
                180

<210> SEQ ID NO 37
<211> LENGTH: 179
<212> TYPE: PRT
<213> ORGANISM: Cavia porcellus

<400> SEQUENCE: 37

Ile Asn Glu Gln Arg Phe Gly Pro Ser Tyr Gln Arg Val Tyr Thr Pro
1               5                   10                  15

Leu Arg Asp Asp Arg Asp Lys Pro Arg Ala His Leu Thr Val Val Arg
                20                  25                  30

Gln Thr Pro Thr Gln His Leu Lys Asn Gln Phe Pro Ala Leu His Trp
            35                  40                  45

Glu His Glu Leu Gly Leu Ala Phe Thr Lys Asn Arg Met Asn Tyr Thr
        50                  55                  60

Asn Lys Phe Leu Val Ile Pro Glu Thr Gly Asp Tyr Phe Val Tyr Ser
65                  70                  75                  80

Gln Ile Thr Phe Arg Gly Thr Thr Ser Glu Cys Gly Ile Ser Pro Gly
                    85                  90                  95

Arg Gln Gln Asn Lys Pro Asp Ser Ile Phe Val Val Ile Thr Lys Val
                100                 105                 110

Thr Asp Ser Tyr Pro Glu Pro Ser Gln Leu Leu Thr Gly Thr Lys Ser
                115                 120                 125

Val Cys Glu Ile Ser Ser Asn Trp Phe Gln Pro Leu Tyr Leu Gly Ala
                130                 135                 140

Met Phe Ser Leu Gln Glu Gly Asp Lys Leu Met Val Asn Val Ser Asp
145                 150                 155                 160

Ile Ser Leu Val Asp Tyr Thr Lys Glu Asp Lys Thr Phe Phe Gly Ala
                    165                 170                 175

Phe Leu Leu

<210> SEQ ID NO 38
<211> LENGTH: 180
<212> TYPE: PRT
<213> ORGANISM: Felis catus

<400> SEQUENCE: 38

Pro Lys Gly Arg Glu Phe Gly Pro Ser His Gln Arg Ala Tyr Thr Ser
1               5                   10                  15

Pro Gly Ala Gly Gly Asp Lys Pro Arg Ala His Leu Thr Val Val Arg
                20                  25                  30
```

-continued

Gln Thr Pro Thr Gln Pro Leu Lys Asn Gln Phe Pro Ala Leu His Trp
            35                  40                  45

Glu His Glu Leu Gly Leu Ala Phe Ile Lys Asn Arg Met Asn Tyr Thr
 50                  55                  60

Asn Lys Phe Leu Val Ile Pro Glu Ser Gly Asp Tyr Phe Val Tyr Ser
65                   70                  75                   80

Gln Val Thr Phe Arg Gly Thr Thr Ser Glu Cys Gly Glu Ile Arg Gln
                85                  90                  95

Gly Ser Arg Leu Asn Lys Pro Asp Ser Ile Ile Val Val Ile Thr Lys
            100                 105                 110

Val Thr Asp Ser Tyr Pro Glu Pro Thr Gln Leu Leu Met Gly Thr Lys
            115                 120                 125

Ser Val Cys Glu Val Gly Ser Asn Trp Phe Gln Pro Ile Tyr Leu Gly
130                 135                 140

Ala Met Phe Ser Leu Gln Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180

<210> SEQ ID NO 39
<211> LENGTH: 180
<212> TYPE: PRT
<213> ORGANISM: Sus scrofa

<400> SEQUENCE: 39

Pro Lys Gly Gln Glu Leu Gly Pro Ser His Gln Arg Val Tyr Ala Pro
1                5                  10                  15

Pro Gly Ala Gly Arg Asp Lys Pro Arg Ala His Leu Thr Val Val Arg
            20                  25                  30

Gln Thr Ser Thr Glu Pro Leu Lys Asn Gln Phe Pro Ala Leu His Trp
            35                  40                  45

Glu His Glu Leu Gly Leu Ala Phe Thr Lys Asn Arg Met Asn Tyr Thr
 50                  55                  60

Asn Lys Phe Leu Val Ile Pro Glu Ser Gly Asp Tyr Phe Ile Tyr Ser
65                   70                  75                   80

Gln Val Thr Phe Arg Gly Thr Thr Ser Glu Cys Gly Glu Ile Ser Gln
                85                  90                  95

Glu Arg Arg Leu Asn Lys Pro Asp Ser Ile Ile Val Val Ile Thr Lys
            100                 105                 110

Val Thr Asp Ser Tyr Pro Glu Pro Thr Gln Leu Leu Met Gly Thr Lys
            115                 120                 125

Ser Val Cys Glu Ile Gly Ser Asn Trp Phe Gln Pro Ile Tyr Leu Gly
130                 135                 140

Ala Met Phe Ser Leu His Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

Ala Phe Leu Leu
            180

<210> SEQ ID NO 40
<211> LENGTH: 179
<212> TYPE: PRT

<213> ORGANISM: Oryctolagus cuniculus

<400> SEQUENCE: 40

Leu Lys Gly Arg Glu Phe Gly Pro Ser Gln Gln Arg Ala Tyr Met Pro
1               5                   10                  15

Leu Arg Ala Asp Gly Asn Lys Pro Arg Ala His Leu Thr Ala Val Lys
            20                  25                  30

Gln Thr Pro Thr Gln Pro Leu Arg Asn His Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Val Ile Pro Glu Ser Gly Asp Tyr Phe Val Tyr Ser
65                  70                  75                  80

Gln Val Thr Phe Arg Gly Thr Thr Ser Glu Cys Gly Val Ile Asn Gln
                85                  90                  95

Arg Arg Arg Gln Thr Lys Pro Asp Ser Ile Val Val Ile Thr Lys
            100                 105                 110

Val Thr Asp Asn Tyr Pro Glu Pro Ala Gln Leu Leu Thr Gly Thr Lys
        115                 120                 125

Ser Val Cys Glu Met Gly Asn Trp Phe Gln Pro Ile Tyr Leu Gly Ala
    130                 135                 140

Met Phe Ser Leu Glu Glu Gly Asp Lys Leu Met Val Asn Val Ser Asp
145                 150                 155                 160

Val Ser Leu Val Asp Tyr Thr Lys Glu Asp Lys Thr Phe Phe Gly Ala
                165                 170                 175

Phe Leu Leu

<210> SEQ ID NO 41
<211> LENGTH: 180
<212> TYPE: PRT
<213> ORGANISM: Canis familiaris

<400> SEQUENCE: 41

Pro Lys Gly Gln Glu Phe Gly His Ser His Gln Arg Ala Tyr Ala Ser
1               5                   10                  15

Pro Arg Ala Gly Gly Asp Lys Pro Arg Ala His Leu Thr Val Val Arg
            20                  25                  30

Gln Ser Pro Thr Gln Pro Leu Glu Ser Leu Phe Pro Ala Leu His Trp
        35                  40                  45

Glu His Glu Leu Gly Leu Ala Phe Thr Lys Asn Arg Met Asn Tyr Thr
    50                  55                  60

Asn Lys Phe Leu Val Ile Pro Glu Ser Gly Asp Tyr Phe Val Tyr Ser
65                  70                  75                  80

Gln Val Thr Phe Arg Gly Thr Thr Ser Glu Cys Gly Glu Ala Arg Gln
                85                  90                  95

Gly Ser Arg Leu Asn Lys Pro Asp Ser Ile Ile Val Val Ile Thr Lys
            100                 105                 110

Val Thr Asp Ser Tyr Pro Glu Pro Thr Gln Leu Leu Met Gly Thr Lys
        115                 120                 125

Ser Val Cys Glu Val Gly Ser Asn Trp Phe Gln Pro Ile Tyr Leu Gly
    130                 135                 140

Ala Met Phe Ser Leu Gln Glu Gly Asp Lys Leu Met Val Asn Val Ser
145                 150                 155                 160

Asp Ile Ser Leu Val Asp Tyr Thr Lys Glu Asp Lys Thr Phe Phe Gly
                165                 170                 175

```
Ala Phe Leu Leu
            180

<210> SEQ ID NO 42
<211> LENGTH: 330
<212> TYPE: PRT
<213> ORGANISM: Homo sapiens

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 43
<211> LENGTH: 329
<212> TYPE: PRT
```

<213> ORGANISM: Homo sapiens

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 44
<211> LENGTH: 330
<212> TYPE: PRT
<213> ORGANISM: Homo sapiens

<400> SEQUENCE: 44

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Tyr Ile Thr Arg Glu Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 45
<211> LENGTH: 327
<212> TYPE: PRT
<213> ORGANISM: Homo sapiens

<400> SEQUENCE: 45

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
145                 150                 155                 160

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
            165                 170                 175

Asn Ser Thr Tyr Arg Val Val Ser Val Leu Thr Val Leu His Gln Asp
        180                 185                 190

Trp Leu Asn Gly Lys Glu Tyr Lys Cys Lys Val Ser Asn Lys Gly Leu
    195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 46
<211> LENGTH: 326
<212> TYPE: PRT
<213> ORGANISM: Homo sapiens

<400> SEQUENCE: 46

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110
```

```
Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 47
<211> LENGTH: 327
<212> TYPE: PRT
<213> ORGANISM: Homo sapiens

<400> SEQUENCE: 47

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Tyr Ile Thr Arg Glu Pro Glu Val Thr Cys Val Val Val
130                 135                 140

Asp Val Ser Gln Glu Asp Pro Glu Val Gln Phe Asn Trp Tyr Val Asp
```

```
            145                 150                 155                 160
Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 48
<211> LENGTH: 105
<212> TYPE: PRT
<213> ORGANISM: Homo sapiens

<400> SEQUENCE: 48

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 49
<211> LENGTH: 357
<212> TYPE: DNA
<213> ORGANISM: Homo sapiens

<400> SEQUENCE: 49
caggtgcagc tggtgcagtc tggggcggag gtgaagaagc ctggggcctc agtgaaggtc    60
tcctgcaagg cttctggata caccttcacc agttatgata tcaactgggt gcgacaggcc   120
cccggacaag gcttgagtg gatgggatgg ctgaacccta acagtggtaa cacaggctat   180
gcacagaagt tccagggcag agtcaccatg accgcagatc gttccaccag cacagcctac   240
```

```
atggagctga gcagcctgag atctgaggac acggccgtgt attactgtgc gagagaagtg      300
cctgagacgg ccgcctttga gtactggggc cagggaaccc tggtcaccgt ctcctca         357
```

<210> SEQ ID NO 50
<211> LENGTH: 333
<212> TYPE: DNA
<213> ORGANISM: Homo sapiens

<400> SEQUENCE: 50

```
cagagcgtgc tgacacagcc tccatccgtg tctggcgccc ctggccagag agtgaccatc      60
agctgcacca gcagcagcag cgacatcgga gccggcctgg gcgtgcactg gtatcagcag     120
ctgcctggca ccgcccccaa gctgctgatc gagggctact acaaccggcc cagcggcgtg     180
cccgaccggt ttagcggcag caagagcggc accagcgcca gcctgacaat caccggcctg     240
ctgcccgagg acgagggcga ctactactgc cagagctacg acggcaccct gagcgccctg     300
ttcggcggag gcaccaagct gaccgtccta ggt                                   333
```

<210> SEQ ID NO 51
<211> LENGTH: 357
<212> TYPE: DNA
<213> ORGANISM: Homo sapiens

<400> SEQUENCE: 51

```
caggtgcagc tggtgcagtc cggcgccgag gtgaagaaac ccggcgcctc cgtgaaggtg      60
tcctgcaagg ccagcggcta caccttcacc tcctacgaca tcaactgggt gaggcaggcc     120
cccggccagg gctggagtg gatgggctgg ctgaacccca actccggcta caccggctac     180
gcccagaagt tccagggcag ggtgaccatg accgccgaca gtccaccctc caccgcctac     240
atggagctgt ccagcctgag gtccgaggac accgccgtgt actattgcgc cagggaggtg     300
cccgagaccg ctgccttcga gtactggggc cagggcaccc tggtgaccgt gtccagc        357
```

<210> SEQ ID NO 52
<211> LENGTH: 333
<212> TYPE: DNA
<213> ORGANISM: Homo sapiens

<400> SEQUENCE: 52

```
cagagcgtgc tgacacagcc tccatccgtg tctggcgccc ctggccagag agtgaccatc      60
agctgcacca gcagcagcag cgacatcgga gccggcctgg gcgtgcactg gtatcagcag     120
ctgcctggca ccgcccccaa gctgctgatc gagggctact acaaccggcc cagcggcgtg     180
cccgaccggt ttagcggcag caagagcggc accagcgcca gcctgacaat caccggcctg     240
ctgcccgagg acgagggcga ctactactgc cagagctggg acggcaccct gagcgccctg     300
ttcggcggag gcaccaagct gaccgtccta ggt                                   333
```

<210> SEQ ID NO 53
<211> LENGTH: 333
<212> TYPE: DNA
<213> ORGANISM: Homo sapiens

<400> SEQUENCE: 53

```
cagagcgtgc tgacacagcc tccatccgtg tctggcgccc ctggccagag agtgaccatc      60
agctgcacca gcagcagcag cgacatcgga gccgctctgg gcgtgcactg gtatcagcag     120
ctgcctggca ccgcccccaa gctgctgatc gagggctact acaaccggcc cagcggcgtg     180
```

```
cccgaccggt ttagcggcag caagagcggc accagcgcca gcctgacaat caccggcctg     240
ctgcccgagg acgagggcga ctactactgc cagagctggg acggcaccct gagcgccctg     300
ttcggcggag gcaccaagct gaccgtccta ggt                                  333

<210> SEQ ID NO 54
<211> LENGTH: 333
<212> TYPE: DNA
<213> ORGANISM: Homo sapiens

<400> SEQUENCE: 54
cagagcgtgc tgacacagcc tccatccgtg tctggcgccc ctggccagag agtgaccatc      60
agctgcacca gcagcagcag cgacatcgga gccggcagcg gcgtgcactg gtatcagcag     120
ctgcctggca ccgcccccaa gctgctgatc gagggctact acaaccggcc cagcggcgtg     180
cccgaccggt ttagcggcag caagagcggc accagcgcca gcctgacaat caccggcctg     240
ctgcccgagg acgagggcga ctactactgc cagagctggg acggcaccct gagcgccctg     300
ttcggcggag gcaccaagct gaccgtccta ggt                                  333

<210> SEQ ID NO 55
<211> LENGTH: 333
<212> TYPE: DNA
<213> ORGANISM: Homo sapiens

<400> SEQUENCE: 55
cagagcgtgc tgacacagcc tccatccgtg tctggcgccc ctggccagag agtgaccatc      60
agctgcacca gcagcagcag cgacatcgga gccggcagg gcgtgcactg gtatcagcag     120
ctgcctggca ccgcccccaa gctgctgatc gagggctact acaaccggcc cagcggcgtg     180
cccgaccggt ttagcggcag caagagcggc accagcgcca gcctgacaat caccggcctg     240
ctgcccgagg acgagggcga ctactactgc cagagctggg acggcaccct gagcgccctg     300
ttcggcggag gcaccaagct gaccgtccta ggt                                  333

<210> SEQ ID NO 56
<211> LENGTH: 333
<212> TYPE: DNA
<213> ORGANISM: Homo sapiens

<400> SEQUENCE: 56
cagagcgtgc tgacacagcc tccatccgtg tctggcgccc ctggccagag agtgaccatc      60
agctgcacca gcagcagcag cgacatcgga gccggcctgg gcgtgctgtg gtatcagcag     120
ctgcctggca ccgcccccaa gctgctgatc gagggctact acaaccggcc cagcggcgtg     180
cccgaccggt ttagcggcag caagagcggc accagcgcca gcctgacaat caccggcctg     240
ctgcccgagg acgagggcga ctactactgc cagagctggg acggcaccct gagcgccctg     300
ttcggcggag gcaccaagct gaccgtccta ggt                                  333

<210> SEQ ID NO 57
<211> LENGTH: 333
<212> TYPE: DNA
<213> ORGANISM: Homo sapiens

<400> SEQUENCE: 57
cagagcgtgc tgacacagcc tccatccgtg tctggcgccc ctggccagag agtgaccatc      60
agctgcacca gcagcagcag cgacatcgga gccggcctgg gcgtgcactg gtatcagcag     120
ctgcctggca ccgcccccaa gctgctgatc gagggctact acaaccggcc cagcggcgtg     180
```

```
cccgaccggt ttagcggcag caagagcggc accagcgcca gcctgacaat caccggcctg      240
ctgcccgagg acgagggcga ctactactgc cagagctttg acggcaccct gagcgccctg      300
ttcggcggag gcaccaagct gaccgtccta ggt                                   333
```

<210> SEQ ID NO 58
<211> LENGTH: 1344
<212> TYPE: DNA
<213> ORGANISM: Homo sapiens

<400> SEQUENCE: 58

```
caggtgcagc tggtgcagtc cggcgccgag gtgaagaaac ccggcgcctc cgtgaaggtg       60
tcctgcaagg ccagcggcta caccttcacc tcctacgaca tcaactgggt gaggcaggcc      120
cccggccagg gctggagtg gatgggctgg ctgaaccca actccggcta caccggctac      180
gcccagaagt tccagggcag ggtgaccatg accgccgaca ggtccacctc caccgcctac      240
atggagctgt ccagcctgag gtccgaggac accgccgtgt actattgcgc cagggaggtg      300
cccgagaccg ctgccttcga gtactggggc cagggcaccc tggtgaccgt gtccagcgcc      360
tccaccaagg gccccagcgt gttccccctg gcccccagct ccaagtccac cagcggcgga      420
accgccgctc tgggctgcct ggtgaaggac tacttccccg agcccgtgac cgtgagctgg      480
aactccggcg ccctgacctc cggcgtgcac accttccccg ccgtgctgca gtccagcggc      540
ctgtactccc tgagctccgt ggtcaccgtg ccctcctcta gcctgggcac ccagacctac      600
atctgcaacg tgaaccacaa gccctccaac accaaggtgg acaaaaaggt ggagcccaag      660
tcctgcgaca agactcacac ctgtcctccc tgccccgccc cgagctgct cggcggaccc      720 tccgtgttcc tgttcccacc caagcccaag gacaccctga tgatctccag gacccccgag      780
gtgacctgcg tggtcgtgga cgtgtcccac gaggaccctg aggtgaagtt caactggtac      840
gtggacggcg tggaggtgca caacgccaag accaagccca gggaggaaca gtacaactcc      900
acctaccggg tcgtgtccgt gctgaccgtc ctgcaccagg actggctgaa cggcaaggag      960
tacaagtgca aggtgtccaa caaggccctg cccgccccca tcgagaagac catctccaag      1020
gccaagggcc agcctcggga gccccaggtg tacacactgc cccttccag ggacgagctg      1080 accaagaacc aggtgtccct gacctgtctg gtgaagggct ctaccccctc gacatcgcc      1140 gtggagtggg agtccaacgg ccagcccgag aacaattaca agaccacacc tcccgtcctg      1200
gactccgacg gctccttctt tctgtactcc aagctgaccg tggacaagtc caggtggcag      1260
caaggcaacg tgttctcctg ctccgtgatg cacgaggccc tgcacaacca ctacacccag      1320
aagtccctga cctgtccccc cggc                                             1344
```

<210> SEQ ID NO 59
<211> LENGTH: 648
<212> TYPE: DNA
<213> ORGANISM: Homo sapiens

<400> SEQUENCE: 59

```
cagagcgtgc tgacacagcc tccatccgtg tctggcgccc ctggccagag agtgaccatc       60
agctgcacca gcagcagcag cgacatcgga gccggcctgg cgtgcactg gtatcagcag      120 ctgcctggca ccgcccccaa gctgctgatc gagggctact acaaccggcc cagcggcgtg      180
cccgaccggt ttagcggcag caagagcggc accagcgcca gcctgacaat caccggcctg      240
ctgcccgagg acgagggcga ctactactgc cagagctggg acggcaccct gagcgccctg      300
```

```
ttcggcggag gcaccaagct gaccgtccta ggtcagccca aggccgctcc cagcgtgacc    360
ctgttccccc caagcagcga ggaactgcag gccaacaagg ccaccctggt gtgcctgatc    420
agcgacttct accctggggc cgtgaccgtg gcctggaagg ccgatagcag ccctgtgaag    480
gccggcgtgg aaaccaccac cccctccaag cagagcaaca caaatacgc cgccagcagc     540 tacctgtccc tgacccccga gcagtggaag tcccaccggt cctacagctg ccaggtgaca    600
cacgagggca gcaccgtgga aaagaccgtg gccccaccg agtgcagc                  648
```

<210> SEQ ID NO 60
<211> LENGTH: 448
<212> TYPE: PRT
<213> ORGANISM: Homo sapiens
<400> SEQUENCE: 60

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Trp Leu Asn Pro Asn Ser Gly Tyr Thr Gly Tyr Ala Gln Lys Phe
    50                  55                  60

Gln Gly Arg Val Thr Met Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Val Pro Glu Thr Ala Ala Phe Glu Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
```

<210> SEQ ID NO 61
<211> LENGTH: 216
<212> TYPE: PRT
<213> ORGANISM: Homo sapiens

<400> SEQUENCE: 61

```
Gln Ser Val Leu Thr Gln Pro Pro Ser Val Ser Gly Ala Pro Gly Gln
1               5                   10                  15

Arg Val Thr Ile Ser Cys Thr Ser Ser Ser Asp Ile Gly Ala Gly
            20                  25                  30

Leu Gly Val His Trp Tyr Gln Gln Leu Pro Gly Thr Ala Pro Lys Leu
        35                  40                  45

Leu Ile Glu Gly Tyr Tyr Asn Arg Pro Ser Gly Val Pro Asp Arg Phe
    50                  55                  60

Ser Gly Ser Lys Ser Gly Thr Ser Ala Ser Leu Thr Ile Thr Gly Leu
65                  70                  75                  80

Leu Pro Glu Asp Glu Gly Asp Tyr Tyr Cys Gln Ser Trp Asp Gly Thr
                85                  90                  95

Leu Ser Ala Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 62
<211> LENGTH: 329
<212> TYPE: PRT

<213> ORGANISM: Homo sapiens

<400> SEQUENCE: 62

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 63
<211> LENGTH: 330
<212> TYPE: PRT
<213> ORGANISM: Homo sapiens

<400> SEQUENCE: 63

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 64
<211> LENGTH: 329
<212> TYPE: PRT
<213> ORGANISM: Homo sapiens

<400> SEQUENCE: 64

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60
```

```
Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Tyr Ile Thr Arg Glu Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 65
<211> LENGTH: 330
<212> TYPE: PRT
<213> ORGANISM: Homo sapiens

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110
```

Pro Ala Pro Glu Leu Ala Gly Ala Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 329
<212> TYPE: PRT
<213> ORGANISM: Homo sapiens

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp

```
                145                 150                 155                 160
        Tyr Val Asp Gly Val Glu Val His Asn Ala Lys Thr Lys Pro Arg Glu
                        165                 170                 175

Glu Gln Tyr Asn Ser Thr Tyr Arg Val Val Ser Val Leu Thr Val Leu
                        180                 185                 190

His Gln Asp Trp Leu Asn Gly Lys Glu Tyr Lys Cys Lys Val Ser Asn
                        195                 200                 205

Lys Ala Leu Pro Ala Pro Ile Glu Lys Thr Ile Ser Lys Ala Lys Gly
                        210                 215                 220

Gln Pro Arg Glu Pro Gln Val Tyr Thr Leu Pro Pro Ser Arg Asp Glu
        225                 230                 235                 240

Leu Thr Lys Asn Gln Val Ser Leu Thr Cys Leu Val Lys Gly Phe Tyr
                        245                 250                 255

Pro Ser Asp Ile Ala Val Glu Trp Glu Ser Asn Gly Gln Pro Glu Asn
                        260                 265                 270

Asn Tyr Lys Thr Thr Pro Pro Val Leu Asp Ser Asp Gly Ser Phe Phe
                        275                 280                 285

Leu Tyr Ser Lys Leu Thr Val Asp Lys Ser Arg Trp Gln Gln Gly Asn
                        290                 295                 300

Val Phe Ser Cys Ser Val Met His Glu Ala Leu His Asn His Tyr Thr
        305                 310                 315                 320

Gln Lys Ser Leu Ser Leu Ser Pro Gly
                        325

<210> SEQ ID NO 67
<211> LENGTH: 326
<212> TYPE: PRT
<213> ORGANISM: Homo sapiens

<400> SEQUENCE: 67

Ala Ser Thr Lys Gly Pro Ser Val Phe Pro Leu Ala Pro Cys Ser Arg
        1               5                   10                  15

Ser Thr Ser Glu Ser Thr Ala Ala Leu Gly Cys Leu Val Lys Asp Tyr
                        20                  25                  30

Phe Pro Glu Pro Val Thr Val Ser Trp Asn Ser Gly Ala Leu Thr Ser
                        35                  40                  45

Gly Val His Thr Phe Pro Ala Val Leu Gln Ser Ser Gly Leu Tyr Ser
                        50                  55                  60

Leu Ser Ser Val Val Thr Val Pro Ser Ser Asn Phe Gly Thr Gln Thr
        65                  70                  75                  80

Tyr Thr Cys Asn Val Asp His Lys Pro Ser Asn Thr Lys Val Asp Lys
                        85                  90                  95

Thr Val Glu Arg Lys Cys Cys Val Glu Cys Pro Pro Cys Pro Ala Pro
                        100                 105                 110

Pro Val Ala Gly Pro Ser Val Phe Leu Phe Pro Pro Lys Pro Lys Asp
                        115                 120                 125

Thr Leu Met Ile Ser Arg Thr Pro Glu Val Thr Cys Val Val Val Asp
                        130                 135                 140

Val Ser His Glu Asp Pro Glu Val Gln Phe Asn Trp Tyr Val Asp Gly
        145                 150                 155                 160

Val Glu Val His Asn Ala Lys Thr Lys Pro Arg Glu Glu Gln Phe Asn
                        165                 170                 175

Ser Thr Phe Arg Val Val Ser Val Leu Thr Val Val His Gln Asp Trp
                        180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 68
<211> LENGTH: 325
<212> TYPE: PRT
<213> ORGANISM: Homo sapiens

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240
```

```
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
                275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 69
<211> LENGTH: 326
<212> TYPE: PRT
<213> ORGANISM: Homo sapiens

<400> SEQUENCE: 69

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Tyr Ile Thr Arg Glu Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
```

```
                275                 280                 285
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 70
<211> LENGTH: 325
<212> TYPE: PRT
<213> ORGANISM: Homo sapiens

<400> SEQUENCE: 70

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320
```

Ser Leu Ser Pro Gly
            325

<210> SEQ ID NO 71
<211> LENGTH: 326
<212> TYPE: PRT
<213> ORGANISM: Homo sapiens

<400> SEQUENCE: 71

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 72
<211> LENGTH: 10
<212> TYPE: PRT
<213> ORGANISM: Homo sapiens

<400> SEQUENCE: 72

Ala Ala Ala Ala Ala Ala Ala Ala Ala Ala
1               5                   10

<210> SEQ ID NO 73
<211> LENGTH: 10
<212> TYPE: PRT
<213> ORGANISM: Homo sapiens

<400> SEQUENCE: 73

Ser Ser Ser Ser Gln Ser Ser Ser Ser Ser
1               5                   10

<210> SEQ ID NO 74
<211> LENGTH: 10
<212> TYPE: PRT
<213> ORGANISM: Homo sapiens

<400> SEQUENCE: 74

Gln Gln Gln Gln Gln Asp Gln Gln Gln Gln
1               5                   10

<210> SEQ ID NO 75
<211> LENGTH: 10
<212> TYPE: PRT
<213> ORGANISM: Homo sapiens

<400> SEQUENCE: 75

Asp Asp Asp Asp Asp His Asp His Asp Asp
1               5                   10

<210> SEQ ID NO 76
<211> LENGTH: 10
<212> TYPE: PRT
<213> ORGANISM: Homo sapiens

<400> SEQUENCE: 76

His His His His His Lys His Lys His His
1               5                   10

<210> SEQ ID NO 77
<211> LENGTH: 10
<212> TYPE: PRT
<213> ORGANISM: Homo sapiens

<400> SEQUENCE: 77

Lys Lys Lys Lys Lys Leu Lys Leu Lys Lys
1               5                   10

<210> SEQ ID NO 78
<211> LENGTH: 10
<212> TYPE: PRT
<213> ORGANISM: Homo sapiens

<400> SEQUENCE: 78

Leu Leu Leu Leu Leu Trp Leu Trp Leu Leu
1               5                   10

<210> SEQ ID NO 79
<211> LENGTH: 10
<212> TYPE: PRT
<213> ORGANISM: Homo sapiens

<400> SEQUENCE: 79

```
Trp Trp Trp Trp Trp Tyr Trp Tyr Trp Trp
1               5                   10
```

<210> SEQ ID NO 80
<211> LENGTH: 12
<212> TYPE: PRT
<213> ORGANISM: Homo sapiens

<400> SEQUENCE: 80

```
Ala Ala Ala Ala Ala Ala Ala Ala Ala Ser
1               5                   10
```

<210> SEQ ID NO 81
<211> LENGTH: 12
<212> TYPE: PRT
<213> ORGANISM: Homo sapiens

<400> SEQUENCE: 81

```
Ser Ser Ser Ser Ser Gln Ser Ser Ser Ser Gln
1               5                   10
```

<210> SEQ ID NO 82
<211> LENGTH: 12
<212> TYPE: PRT
<213> ORGANISM: Homo sapiens

<400> SEQUENCE: 82

```
Gln Gln Gln Gln Gln Asp Gln Gln Gln Gln Asp
1               5                   10
```

<210> SEQ ID NO 83
<211> LENGTH: 12
<212> TYPE: PRT
<213> ORGANISM: Homo sapiens

<400> SEQUENCE: 83

```
Asp Asp Asp Asp Asp His Asp Asp Asp Asp His
1               5                   10
```

<210> SEQ ID NO 84
<211> LENGTH: 12
<212> TYPE: PRT
<213> ORGANISM: Homo sapiens

<400> SEQUENCE: 84

```
His His His His His Lys His His His Lys His
1               5                   10
```

<210> SEQ ID NO 85
<211> LENGTH: 12
<212> TYPE: PRT
<213> ORGANISM: Homo sapiens

<400> SEQUENCE: 85

```
Lys Lys Lys Lys Lys Leu Lys Lys Lys Lys Leu
1               5                   10
```

<210> SEQ ID NO 86
<211> LENGTH: 12
<212> TYPE: PRT
<213> ORGANISM: Homo sapiens

<400> SEQUENCE: 86

```
Leu Trp Leu Leu Leu Trp Leu Leu Leu Leu Leu Trp
```

```
1               5                   10
```

<210> SEQ ID NO 87
<211> LENGTH: 12
<212> TYPE: PRT
<213> ORGANISM: Homo sapiens

<400> SEQUENCE: 87

```
Tyr Tyr Trp Trp Trp Tyr Trp Trp Trp Trp Trp Tyr
1               5                   10
```

<210> SEQ ID NO 88
<211> LENGTH: 7
<212> TYPE: PRT
<213> ORGANISM: Homo sapiens

<400> SEQUENCE: 88

```
Tyr Tyr Tyr Tyr Tyr Tyr Tyr
1               5
```

<210> SEQ ID NO 89
<211> LENGTH: 14
<212> TYPE: PRT
<213> ORGANISM: Homo sapiens

<400> SEQUENCE: 89

```
Ala Ala Ala Ala Ala Ala Ala Ser Ala Ala Ala Ala
1               5                   10
```

<210> SEQ ID NO 90
<211> LENGTH: 14
<212> TYPE: PRT
<213> ORGANISM: Homo sapiens

<400> SEQUENCE: 90

```
Ser Gln Gln Gln Gln Ser Ser Ser Gln Ser Ser Ser Ser Ser
1               5                   10
```

<210> SEQ ID NO 91
<211> LENGTH: 14
<212> TYPE: PRT
<213> ORGANISM: Homo sapiens

<400> SEQUENCE: 91

```
Gln Asp Asp Asp Asp Gln Gln Gln Asp Gln Gln Gln Gln Gln
1               5                   10
```

<210> SEQ ID NO 92
<211> LENGTH: 14
<212> TYPE: PRT
<213> ORGANISM: Homo sapiens

<400> SEQUENCE: 92

```
Asp His His His His His Asp Asp His Asp Asp Asp Asp
1               5                   10
```

<210> SEQ ID NO 93
<211> LENGTH: 14
<212> TYPE: PRT
<213> ORGANISM: Homo sapiens

<400> SEQUENCE: 93

```
His Lys Lys Lys Lys Lys His His Lys His His His His
1               5                   10
```

```
<210> SEQ ID NO 94
<211> LENGTH: 14
<212> TYPE: PRT
<213> ORGANISM: Homo sapiens

<400> SEQUENCE: 94

Lys Leu Leu Leu Leu Leu Lys Lys Leu Lys Lys Lys Lys Lys
1               5                   10

<210> SEQ ID NO 95
<211> LENGTH: 14
<212> TYPE: PRT
<213> ORGANISM: Homo sapiens

<400> SEQUENCE: 95

Leu Trp Trp Trp Trp Trp Leu Leu Trp Leu Trp Leu Leu Leu
1               5                   10

<210> SEQ ID NO 96
<211> LENGTH: 14
<212> TYPE: PRT
<213> ORGANISM: Homo sapiens

<400> SEQUENCE: 96

Trp Tyr Tyr Tyr Tyr Tyr Trp Trp Tyr Trp Tyr Trp Trp Trp
1               5                   10

<210> SEQ ID NO 97
<211> LENGTH: 10
<212> TYPE: PRT
<213> ORGANISM: Homo sapiens

<400> SEQUENCE: 97

Ala Ala Ala Ala Ala Ala Ala Ala Ser Ala
1               5                   10

<210> SEQ ID NO 98
<211> LENGTH: 10
<212> TYPE: PRT
<213> ORGANISM: Homo sapiens

<400> SEQUENCE: 98

Ser Gln Ser Ser Ser Ser Ser Gln Gln Ser
1               5                   10

<210> SEQ ID NO 99
<211> LENGTH: 10
<212> TYPE: PRT
<213> ORGANISM: Homo sapiens

<400> SEQUENCE: 99

Asp Asp Gln Gln Gln Gln Gln Asp Asp Gln
1               5                   10

<210> SEQ ID NO 100
<211> LENGTH: 10
<212> TYPE: PRT
<213> ORGANISM: Homo sapiens

<400> SEQUENCE: 100

His His Asp His Asp Asp Asp His His Asp
1               5                   10

<210> SEQ ID NO 101
```

```
<211> LENGTH: 10
<212> TYPE: PRT
<213> ORGANISM: Homo sapiens

<400> SEQUENCE: 101

Lys Lys His Lys His His His Lys Lys His
1               5                   10

<210> SEQ ID NO 102
<211> LENGTH: 10
<212> TYPE: PRT
<213> ORGANISM: Homo sapiens

<400> SEQUENCE: 102

Leu Leu Lys Leu Lys Lys Lys Leu Leu Lys
1               5                   10

<210> SEQ ID NO 103
<211> LENGTH: 10
<212> TYPE: PRT
<213> ORGANISM: Homo sapiens

<400> SEQUENCE: 103

Trp Trp Leu Trp Leu Leu Trp Trp Trp Trp
1               5                   10

<210> SEQ ID NO 104
<211> LENGTH: 10
<212> TYPE: PRT
<213> ORGANISM: Homo sapiens

<400> SEQUENCE: 104

Tyr Tyr Trp Tyr Trp Trp Tyr Tyr Tyr Tyr
1               5                   10
```

ANTIBODIES THAT SPECIFICALLY BIND TO TL1A AND METHODS OF TREATING RESPIRATORY TRACT DISEASES

CROSS REFERENCE TO RELATED APPLICATIONS

This application claims priority to U.S. Provisional Application No. 62/220,442, filed on Sep. 18, 2015, the contents of which are incorporated by reference herein, in their entirety and for all purposes.

REFERENCE TO A SEQUENCE LISTING

This application includes a Sequence Listing submitted electronically as a text file named 2873 2750002_Seqlisting, created on Jun. 14, 2021 with a size of 101,663 bytes. The Sequence Listing is incorporated by reference herein.

FIELD OF THE INVENTION

This disclosure relates generally to the field of antibody engineering. More specifically, this disclosure relates to variant antibodies that bind specifically to TL1A, and which inhibit the interaction between TL1A and the death receptor 3 (DR3). In some aspects, the antibodies also inhibit the interaction between TL1A and the decoy receptor 3 (DcR3). The antibodies have improved potency relative to the parent antibody from which the variants were derived.

BACKGROUND OF THE INVENTION

Various publications, including patents, published applications, accession numbers, technical articles and scholarly articles are cited throughout the specification. Each of these cited publications is incorporated by reference, in its entirety and for all purposes, in this document.

TNF-like ligand 1A (TL1A, syn. TNF superfamily member 15 (TNFSF15); TL1 and VEGI) is a member of the tumor necrosis factor superfamily, which is expressed by antigen presenting cells (including dendritic cells, B cells and macrophages), CD4+ and CD8+ T cells and endothelial cells. TL1A can be expressed on the cell surface or secreted as a soluble cytokine. The receptor for TL1A, Death Receptor 3 (DR3) is expressed by a variety of cells, including CD4+ and CD8+ T cells, NK cells, NKT cells and FOXP3+ regulatory T (Treg) cells and type-2 and type-3 innate lymphoid cells (ILC2 and ILC3).

TL1A can also bind a decoy receptor (DcR3), which is a competitive inhibitor of DR3. DcR3 also acts as a decoy receptor for Fas-ligand (Fas-L) and lymphotoxin-like inducible protein that competes with glycoprotein D for binding herpesvirus entry mediator on T-cells (LIGHT). Accordingly, DcR3 is an important regulator of several signal transduction pathways.

The TL1A/DR3 signalling pathway has been implicated in several biological systems, which are associated with human diseases. For example, TL1A has been shown to play a role in immunity, angiogenesis, and homeostasis of barrier tissues. Inhibiting TL1A interaction with DR3 also has been shown to promote a therapeutic benefit in several immune-mediated conditions, such as experimental autoimmune encephalomyelitis (EAE; a model of multiple sclerosis), colitis, ulcerative colitis, Crohn's disease, inflammatory bowel disease, skin disease, asthma and arthritis.

Accordingly, compounds that inhibit TL1A activity are desirable, e.g., for their therapeutic, prophylactic, diagnostic and prognostic uses.

SUMMARY OF THE INVENTION

Provided herein is a recombinant antibody comprising a heavy chain variable region CDR1 comprising the amino acid sequence of SEQ ID NO: 15, a heavy chain variable region CDR2 comprising the amino acid sequence of SEQ ID NO: 28, a heavy chain variable region CDR3 comprising the amino acid sequence of SEQ ID NO: 17, a light chain variable region CDR1 comprising the amino acid sequence of SEQ ID NO: 29, a light chain variable region CDR2 comprising the amino acid sequence of SEQ ID NO: 19, and a light chain variable region CDR3 comprising the amino acid sequence of SEQ ID NO: 30, provided that when the heavy chain variable region comprises the amino acid sequence of SEQ ID NO: 1, the light chain variable region does not comprise the amino acid sequence of SEQ ID NO: 2.

In some aspects, the antibody comprises a heavy chain variable region CDR2 comprising the amino acid sequence of SEQ ID NO: 16, and a light chain variable region CDR3 comprising the amino acid sequence of SEQ ID NO: 22. In some aspects, the antibody comprises a heavy chain variable region CDR2 comprising the amino acid sequence of SEQ ID NO: 21, and a light chain variable region CDR3 comprising the amino acid sequence of SEQ ID NO: 20. In some aspects, the antibody comprises a heavy chain variable region CDR2 comprising the amino acid sequence of SEQ ID NO: 16, a light chain variable region CDR1 comprising the amino acid sequence of SEQ ID NO: 23, and a light chain variable region CDR3 comprising the amino acid sequence of SEQ ID NO: 22. In some aspects, the antibody comprises a heavy chain variable region CDR2 comprising the amino acid sequence of SEQ ID NO: 16, a light chain variable region CDR1 comprising the amino acid sequence of SEQ ID NO: 24, and a light chain variable region CDR3 comprising the amino acid sequence of SEQ ID NO: 22. In some aspects, the antibody comprises a heavy chain variable region CDR2 comprising the amino acid sequence of SEQ ID NO: 16, a light chain variable region CDR1 comprising the amino acid sequence of SEQ ID NO: 25, and a light chain variable region CDR3 comprising the amino acid sequence of SEQ ID NO: 22. In some aspects, the antibody comprises a heavy chain variable region CDR2 comprising the amino acid sequence of SEQ ID NO: 16, a light chain variable region CDR1 comprising the amino acid sequence of SEQ ID NO: 26, and a light chain variable region CDR3 comprising the amino acid sequence of SEQ ID NO: 22. In some aspects, the antibody comprises a heavy chain variable region CDR2 comprising the amino acid sequence of SEQ ID NO: 21 and a light chain variable region CDR3 comprising the amino acid sequence of SEQ ID NO: 22. In some aspects, the antibody comprises a heavy chain variable region CDR2 comprising the amino acid sequence of SEQ ID NO: 21, a light chain variable region CDR1 comprising the amino acid sequence of SEQ ID NO: 24, and a light chain variable region CDR3 comprising the amino acid sequence of SEQ ID NO: 22. In some aspects, the antibody comprises a heavy chain variable region CDR2 comprising the amino acid sequence of SEQ ID NO: 21, a light chain variable region CDR1 comprising the amino acid sequence of SEQ ID NO: 25, and a light chain variable region CDR3 comprising the amino acid sequence of SEQ ID NO: 22. In some aspects, the antibody comprises a heavy chain variable region CDR2 comprising the amino acid sequence of SEQ ID NO: 21, a light chain variable region CDR1 comprising the amino acid sequence of SEQ ID NO: 26, and a light chain variable region CDR3 comprising the amino acid sequence of SEQ ID NO: 22. In some aspects, the antibody comprises a heavy chain variable region CDR2 comprising the amino acid sequence of SEQ ID NO: 21, and a light chain variable region CDR3 comprising the amino acid sequence of SEQ ID NO: 27.

Also provided herein is a recombinant antibody comprising a heavy chain variable region comprising the amino acid sequence of SEQ ID NO: 1 or SEQ ID NO: 3 and a light chain variable region comprising the amino acid sequence of SEQ ID NO: 14, provided that when the heavy chain variable region comprises the amino acid sequence of SEQ ID NO: 1, the light chain variable region does not comprise the amino acid sequence of SEQ ID NO: 2. In some aspects, the antibody comprises a heavy chain variable region comprising the amino acid sequence of SEQ ID NO: 1, and a light chain variable region comprising the amino acid sequence of SEQ ID NO: 4. In some aspects, the antibody comprises a heavy chain variable region comprising the amino acid sequence of SEQ ID NO: 3, and a light chain variable region comprising the amino acid sequence of SEQ ID NO: 2. In some aspects, the antibody comprises a heavy chain variable region comprising the amino acid sequence of SEQ ID NO: 1, and a light chain variable region comprising the amino acid sequence of SEQ ID NO: 5. In some aspects, the antibody comprises a heavy chain variable region comprising the amino acid sequence of SEQ ID NO: 1, and a light chain variable region comprising the amino acid sequence of SEQ ID NO: 6. In some aspects, the antibody comprises a heavy chain variable region comprising the amino acid sequence of SEQ ID NO: 1, and a light chain variable region comprising the amino acid sequence of SEQ ID NO: 7. In some aspects, the antibody comprises a heavy chain variable region comprising the amino acid sequence of SEQ ID NO: 1, and a light chain variable region comprising the amino acid sequence of SEQ ID NO: 8. In some aspects, the antibody comprises a heavy chain variable region comprising the amino acid sequence of SEQ ID NO: 3, and a light chain variable region comprising the amino acid sequence of SEQ ID NO: 4. In some aspects, the antibody comprises a heavy chain variable region comprising the amino acid sequence of SEQ ID NO: 3, and a light chain variable region comprising the amino acid sequence of SEQ ID NO: 6. In some aspects, the antibody comprises a heavy chain variable region comprising the amino acid sequence of SEQ ID NO: 3, and a light chain variable region comprising the amino acid sequence of SEQ ID NO: 7. In some aspects, the antibody comprises a heavy chain variable region comprising the amino acid sequence of SEQ ID NO: 3, and a light chain variable region comprising the amino acid sequence of SEQ ID NO: 8. In some aspects, the antibody comprises a heavy chain variable region comprising the amino acid sequence of SEQ ID NO: 3, and a light chain variable region comprising the amino acid sequence of SEQ ID NO: 10.

In some aspects, the antibody comprises a heavy chain comprising the amino acid sequence of SEQ ID NO: 60. In some aspects, the antibody comprises a light chain comprising the amino acid sequence of SEQ ID NO: 61. In some aspects, the antibody comprises a heavy chain comprising the amino acid sequence of SEQ ID NO: 60 and a light chain comprising the amino acid sequence of SEQ ID NO: 61.

Such recombinant antibodies preferably are full length, and preferably are monoclonal. Such recombinant antibodies bind to TL1A with enhanced affinity relative to an antibody having a heavy chain variable region comprising the amino acid sequence of SEQ ID NO: 1 and a light chain variable region comprising the amino acid sequence of SEQ ID NO: 2. Such recombinant antibodies have enhanced potency relative to an antibody having a heavy chain variable region comprising the amino acid sequence of SEQ ID NO: 1 and a light chain variable region comprising the amino acid sequence of SEQ ID NO: 2. The enhanced potency may be at least about 10-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 12-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 13-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 15-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 20-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 25-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 27-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 40-fold greater potency relative to an antibody having a heavy chain variable region comprising the amino acid sequence of SEQ ID NO: 1 and a light chain variable region comprising the amino acid sequence of SEQ ID NO: 2. Fold-enhancement of potency may be determined according to a TL1A-induced caspase potency assay in TF-1 cells.

Such recombinant antibodies may comprise a human IgG1 heavy chain constant region, a human IgG2 heavy chain constant region, or a human IgG4 heavy chain constant region, or any allotypes thereof. The human IgG1 heavy chain constant region may comprise SEQ ID NO: 42, or SEQ ID NO: 43 (human IgG1 ΔK), or SEQ ID NO: 44 (human IgG1 with YTE), or SEQ ID NO: 64 (human IgG1 with YTE and ΔK), or SEQ ID NO: 63 (human IgG1 with L234A, L235A, G237A) or SEQ ID NO: 62 (human IgG1 with L234A, L235A, G237A and ΔK), or SEQ ID NO: 65 (human IgG1 with L235A and G237A) or SEQ ID NO: 66 (human IgG1 with L235A, G237A and ΔK). The human IgG2 heavy chain constant region may comprise SEQ ID NO: 67, or SEQ ID NO: 70 (human IgG2 ΔK), or SEQ ID NO: 71 (human IgG2 with A330S, P331S), or SEQ ID NO: 68 (human IgG2 with A330S, P331S and ΔK). The human IgG4 heavy chain IgG4 constant region may comprise SEQ ID NO: 45, or SEQ ID NO: 46 (human IgG4 with S228P and ΔK), or SEQ ID NO: 47 (human IgG4 with S228P and YTE), or SEQ ID NO: 69 (human IgG4 with S228P, YTE and ΔK). It will be understood that an IgG4 heavy chain could be used without the stabilizing substitution S228P (e.g., IgG4 with YTE alone, or IgG4 with YTE and ΔK, or IgG4 with ΔK alone).

The recombinant antibodies may comprise a human lambda light chain constant region or an allotype thereof. The human light chain lambda constant region may comprise SEQ ID NO: 48.

Such recombinant antibodies bind to human TL1A, and may bind to the TL1A of a non-human primate, or the TL1A of a non-human mammal such as a mouse, rat, guinea pig, cat, dog, rabbit, or pig.

Such recombinant antibodies may be used in a method for treating a respiratory tract disease, a method for treating a gastrointestinal disease, a method of treating a skin disease, or a method of treating arthritis, or may be for use in the treatment of a respiratory tract disease, a gastrointestinal disease, a skin disease, or arthritis, or may be for use in the manufacture of a medicament for the treatment of a respiratory tract disease, a gastrointestinal disease, a skin disease, or arthritis. The respiratory tract disease may comprise one or more of asthma, chronic obstructive pulmonary disease (COPD), pulmonary fibrosis, pulmonary sarcoidosis, allergic rhinitis, or cystic fibrosis. The gastrointestinal disease may comprise one or more of inflammatory bowel disease, Crohn's disease, colitis, ulcerative colitis, eosinophilic esophagitis, or irritable bowel syndrome, or a gastrointestinal disease or condition associated with cystic fibrosis. The arthritis may comprise rheumatoid arthritis. The skin disease may comprise one or more of atopic dermatitis, eczema, and scleroderma.

Human subjects, non-human primate subjects, or non-human mammalian subjects in need of such treatments may be treated with the antibodies or a composition comprising the antibodies, for example, by administering the antibodies or composition thereof to the subject. Administration may be parenteral, for example, subcutaneous and/or intravenous.

Such recombinant antibodies may be used in a method for detecting TL1A on the surface of peripheral blood mononuclear cells (PBMCs). The methods comprise contacting an antibody that binds to TL1A as described or exemplified herein with PBMCs obtained from a subject, and detecting the antibody bound to TL1A on the surface of the PBMCs. The methods may further comprise quantifying the level of TL1A on the PBMCs. The methods may further comprise obtaining the PBMCs from the subject.

Such recombinant antibodies may be used in a method for detecting TL1A in blood serum. The methods comprise contacting an antibody that binds to TL1A as described or exemplified herein with blood serum obtained from a subject, and detecting the antibody bound to TL1A in the serum. The methods may further comprise quantifying the level of TL1A in the blood serum. The methods may further comprise obtaining the serum from blood obtained from the subject. The methods may further comprise obtaining blood from the subject.

Polynucleotides encoding one or more of the heavy chain variable region and the light chain variable region of such antibodies are provided. The polynucleotides may further encode a heavy chain constant region and/or a light chain constant region.

In some aspects, a polynucleotide comprises a nucleic acid sequence encoding an antibody heavy chain variable region comprising the amino acid sequence of SEQ ID NO: 3, for example, a nucleic acid sequence comprising SEQ ID NO: 51 or SEQ ID NO: 58. In some aspects, the polynucleotide comprises a nucleic acid sequence encoding an antibody light chain variable region comprising the amino acid sequence of SEQ ID NO: 2, for example, a nucleic acid sequence comprising SEQ ID NO: 50. In some aspects, the polynucleotide comprises a nucleic acid sequence encoding an antibody light chain variable region comprising the amino acid sequence of SEQ ID NO: 4, for example, a nucleic acid sequence comprising SEQ ID NO: 52 or SEQ ID NO: 59. In some aspects, the polynucleotide comprises a nucleic acid sequence encoding an antibody light chain variable region comprising the amino acid sequence of SEQ ID NO: 6, for example, a nucleic acid sequence comprising SEQ ID NO: 54. In some aspects, the polynucleotide comprises a nucleic acid sequence encoding an antibody light chain variable region comprising the amino acid sequence of SEQ ID NO: 7, for example, a nucleic acid sequence comprising SEQ ID NO: 55. In some aspects, the polynucleotide comprises a nucleic acid sequence encoding an antibody light chain variable region comprising the amino acid sequence of SEQ ID NO: 8, for example, a nucleic acid sequence comprising SEQ ID NO: 56. In some aspects, the polynucleotide comprises a nucleic acid sequence encoding an antibody light chain variable region comprising the amino acid sequence of SEQ ID NO: 10, for example, a nucleic acid sequence comprising SEQ ID NO: 57.

In some aspects, the polynucleotide comprises a nucleic acid sequence encoding an antibody heavy chain variable region comprising the amino acid sequence of SEQ ID NO: 1, for example, a nucleic acid sequence comprising SEQ ID NO: 49. In some aspects, the polynucleotide comprises a nucleic acid sequence encoding an antibody light chain variable region comprising the amino acid sequence of SEQ ID NO: 4, for example, a nucleic acid sequence comprising SEQ ID NO: 52. In some aspects, the polynucleotide comprises a nucleic acid sequence encoding an antibody light chain variable region comprising the amino acid sequence of SEQ ID NO: 5, for example, a nucleic acid sequence comprising SEQ ID NO: 53. In some aspects, the polynucleotide comprises a nucleic acid sequence encoding an antibody light chain variable region comprising the amino acid sequence of SEQ ID NO: 6, for example, a nucleic acid sequence comprising SEQ ID NO: 54. In some aspects, the polynucleotide comprises a nucleic acid sequence encoding an antibody light chain variable region comprising the amino acid sequence of SEQ ID NO: 7, for example, a nucleic acid sequence comprising SEQ ID NO: 55. In some aspects, the polynucleotide comprises a nucleic acid sequence encoding an antibody light chain variable region comprising the amino acid sequence of SEQ ID NO: 8, for example, a nucleic acid sequence comprising SEQ ID NO: 56.

Vectors comprising one or more of such polynucleotides are provided. Cells transformed with one or more such polynucleotides or such vectors are provided. Transformed cells may be mammalian, and preferably are mammalian expression host cells such as CHO cells, NSO cells, or HEK293 cells.

BRIEF DESCRIPTION OF THE DRAWINGS

FIG. 1 shows the positions and identities of each of the single amino acid substitutions made to the CDR1 or CDR2 regions or to selected amino acid residues adjacent to CDR2 of the parent antibody (320-179) variable heavy chain. Boxed regions represent the CDRs according to the AbM numbering system.

FIG. 2 shows the positions and the identities of each of the single amino acid substitutions made to the CDR1 or CDR3 regions of the parent antibody (320-179) variable light chain. Boxed regions represent the CDRs according to the AbM numbering system.

FIG. 3 shows an alignment of variant anti-TL1A-antibody heavy chains.

FIG. 4 shows an alignment of variant anti-TL1A-binding antibody light chains.

FIG. 6 shows the results of TF-1 cell caspase potency assays with variant TL1A antibodies.

FIG. 8 shows that antibody 320-587 has superior TL1A potency in a TF-1 cell caspase potency assay, compared to other published anti-TL1A antibodies across several different experiments.

FIG. 9 shows various anti-TL1A antibodies that inhibit TL1A binding to DR3, as compared to an isotype control as measured in ELISA format.

FIG. 10 shows that the parent antibody, 320-179, does not inhibit TL1A binding to DcR3 while the variant anti-TL1A antibodies do inhibit the TL1A-DcR3 interaction.

FIG. 20E shows representative sections of ulcer area at 7 and 14 days.

DETAILED DESCRIPTION OF THE INVENTION

Figure 5:
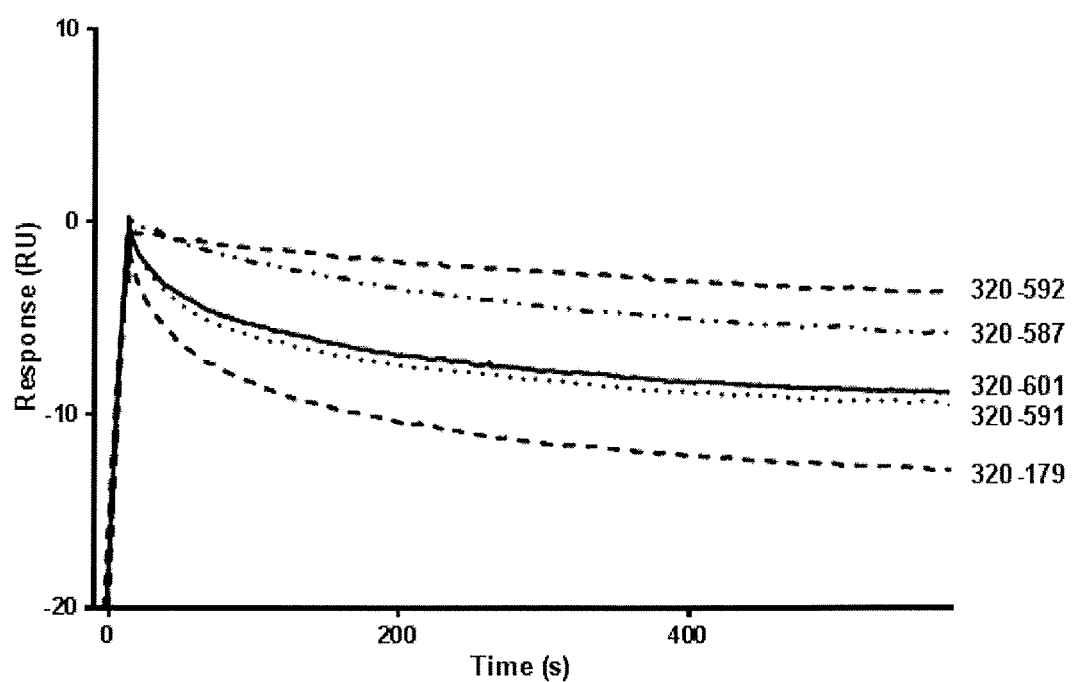
FIG. 5 shows a comparison of the TL1A dissociation phase of variant anti-TL1A antibodies, as measured by SPR.

Various terms relating to aspects of disclosure are used throughout the specification and claims. Such terms are to be given their ordinary meaning in the art, unless otherwise indicated. Other specifically defined terms are to be construed in a manner consistent with the definition provided herein.

The terms "subject" and "patient" are used interchangeably and include any animal. Mammals are preferred, including companion (e.g., cat, dog) and farm mammals (e.g., pig, horse, cow), as well as rodents, including mice, rabbits, and rats, guinea pigs, and other rodents. Non-human primates, such as cynomolgus monkeys, are more preferred, and human beings are highly preferred.

A molecule such as an antibody has been "isolated" if it has been altered and/or removed from its natural environment by the hand of a human being.

As used herein, the singular forms "a," "an," and "the" include plural referents unless expressly stated otherwise.

"Specificity" in the context of antibody-antigen interactions is not necessarily an absolute designation but may constitute a relative term signifying the degree of selectivity of an antibody for an antigen-positive cell compared to an antigen-negative cell. Specificity of an antibody for an antigen-positive cell is mediated by the variable regions of the antibody, and usually by the complementarity determining regions (CDRs) of the antibody. A construct may have from about 100 to about 1000-fold specificity for antigen-positive cells compared to antigen-negative cells.

As used herein, the term "recombinant" includes the expression from genes made by genetic engineering or otherwise by laboratory manipulation.

The disclosure provides variant anti-TL1A antibodies comprising a recombinantly altered heavy and/or light chain variable region of antibody 320-179, which variant antibodies specifically bind to TL1A. These 320-179 variant antibodies inhibit the capability of TL1A to interact with DR3 and, in some aspects, also with DcR3 and, further inhibit the signalling induced by the interaction of TL1A with DR3. These antibodies have enhanced potency relative to antibody 320-179. These antibodies have enhanced affinity for TL1A relative to antibody 320-179.

The enhanced potency may be at least about 10-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 12-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 13-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 15-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 20-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 25-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 27-fold greater potency relative to an antibody having a heavy chain variable region comprising the amino acid sequence of SEQ ID NO: 1 and a light chain variable region comprising the amino acid sequence of SEQ ID NO: 2. The enhanced potency may be at least about 40-fold greater potency relative to an antibody having a heavy chain variable region comprising the amino acid sequence of SEQ ID NO: 1 and a light chain variable region comprising the amino acid sequence of SEQ ID NO: 2. Fold-enhancement of potency may be determined, for example, by measuring caspase release in TL1A-induced apoptosis in a TF-1 cell assay.

The 320-179 variant antibodies are recombinantly expressed, and specifically bind to TL1A. The parent antibody, 320-179, comprises a heavy chain variable region comprising the amino acid sequence of SEQ ID NO: 1 and a light chain variable region comprising the amino acid sequence of SEQ ID NO: 2. In some aspects, a 320-179 variant antibody comprises a heavy chain variable region comprising the amino acid sequence of SEQ ID NO: 1 or SEQ ID NO: 3 and a light chain variable region comprising the amino acid sequence of SEQ ID NO: 14, provided that when the heavy chain variable region comprises the amino acid sequence of SEQ ID NO: 1, the light chain variable region does not comprise the amino acid sequence of SEQ ID NO: 2. The 320-179 variant antibody is capable of inhibiting the interaction of TL1A with DR3. The 320-179 variant antibody has enhanced potency relative to antibody 320-179 and/or has enhanced affinity for TL1A relative to antibody 320-179.

In some aspects, the heavy chain variable region comprises the amino acid sequence of SEQ ID NO: 1, and the light chain variable region comprises the amino acid sequence of SEQ ID NO: 4. In some aspects, the heavy chain variable region comprises the amino acid sequence of SEQ ID NO: 3, and the light chain variable region comprises the amino acid sequence of SEQ ID NO: 2. In some aspects, the heavy chain variable region comprises the amino acid sequence of SEQ ID NO: 1, and the light chain variable region comprises the amino acid sequence of SEQ ID NO: 5. In some aspects, the heavy chain variable region comprises the amino acid sequence of SEQ ID NO: 1, and the light chain variable region comprises the amino acid sequence of SEQ ID NO: 6. In some aspects, the heavy chain variable region comprises the amino acid sequence of SEQ ID NO: 1, and the light chain variable region comprises the amino acid sequence of SEQ ID NO: 7. In some aspects, the heavy chain variable region comprises the amino acid sequence of SEQ ID NO: 1, and the light chain variable region comprises the amino acid sequence of SEQ ID NO: 8. In some highly preferred aspects, the heavy chain variable region comprises the amino acid sequence of SEQ ID NO: 3, and the light chain variable region comprises the amino acid sequence of SEQ ID NO: 4. In some aspects, the heavy chain variable region comprises the amino acid sequence of SEQ ID NO: 3, and the light chain variable region comprises the amino acid sequence of SEQ ID NO: 6. In some aspects, the heavy chain variable region comprises the amino acid sequence of SEQ ID NO: 3, and the light chain variable region comprises the amino acid sequence of SEQ ID NO: 7. In some aspects, the heavy chain variable region comprises the amino acid sequence of SEQ ID NO: 3, and the light chain variable region comprises the amino acid sequence of SEQ ID NO: 8. In some aspects, the heavy chain variable region comprises the amino acid sequence of SEQ ID NO: 3, and the light chain variable region comprises the amino acid sequence of SEQ ID NO: 10.

In highly preferred aspects, the 320-179 variant antibody comprises a heavy chain variable region comprising the amino acid sequence of SEQ ID NO: 3, and a light chain variable region comprising the amino acid sequence of SEQ ID NO: 4, and specifically binds to TL1A. In some aspects, the heavy chain variable region of SEQ ID NO: 3 is joined to a human IgG1(ΔK) heavy chain constant region (e.g., SEQ ID NO: 43) such that the heavy chain comprises SEQ ID NO: 60. In some aspects, the light chain variable region of SEQ ID NO: 4 is joined to a lambda human light chain constant region (e.g., SEQ ID NO: 48) such that the light chain comprises SEQ ID NO: 61. The 320-179 variant antibody is capable of inhibiting the interaction of TL1A with DR3. The variant antibody has enhanced potency relative to antibody 320-179 and/or has enhanced affinity for TL1A relative to antibody 320-179.

In some aspects, the 320-179 variant antibodies are recombinantly expressed and specifically bind to TL1A, and comprise a heavy chain variable region CDR1 comprising the amino acid sequence of SEQ ID NO: 15, a heavy chain variable region CDR2 comprising the amino acid sequence of SEQ ID NO: 28, and a heavy chain variable region CDR3 comprising the amino acid sequence of SEQ ID NO: 17. The antibodies may comprise a light chain variable region CDR1 comprising the amino acid sequence of SEQ ID NO: 29, a light chain variable region CDR2 comprising the amino acid sequence of SEQ ID NO: 19, and a light chain variable region CDR3 comprising the amino acid sequence of SEQ ID NO: 30. In aspects where the heavy chain variable region comprises the amino acid sequence of SEQ ID NO: 1, the light chain variable region preferably does not comprise the amino acid sequence of SEQ ID NO: 2. These 320-179 variant antibodies are capable of inhibiting the interaction of TL1A with DR3. These 320-179 variant antibodies have enhanced potency relative to antibody 320-179 and/or have enhanced affinity for TL1A relative to antibody 320-179.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 16, a heavy chain variable region CDR3 comprising the amino acid sequence of SEQ ID NO: 17, a light chain variable region CDR1 comprising the amino acid sequence of SEQ ID NO: 18, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 16, a heavy chain variable region CDR3 comprising the amino acid sequence of SEQ ID NO: 17, a light chain variable region CDR1 comprising the amino acid sequence of SEQ ID NO: 23, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 16, a heavy chain variable region CDR3 comprising the amino acid sequence of SEQ ID NO: 17, a light chain variable region CDR1 comprising the amino acid sequence of SEQ ID NO: 24, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 16, a heavy chain variable region CDR3 comprising the amino acid sequence of SEQ ID NO: 17, a light chain variable region CDR1 comprising the amino acid sequence of SEQ ID NO: 25, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 21, a heavy chain variable region CDR3 comprising the amino acid sequence of SEQ ID NO: 17, a light chain variable region CDR1 comprising the amino acid sequence of SEQ ID NO: 18, a light chain variable region CDR2 comprising the amino acid sequence of SEQ ID NO: 19, and a light chain variable region CDR3 comprising the amino acid sequence of SEQ ID NO: 20.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 16, a heavy chain variable region CDR3 comprising the amino acid sequence of SEQ ID NO: 17, a light chain variable region CDR1 comprising the amino acid sequence of SEQ ID NO: 26, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 21, a heavy chain variable region CDR3 comprising the amino acid sequence of SEQ ID NO: 17, a light chain variable region CDR1 comprising the amino acid sequence of SEQ ID NO: 18, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 21, a heavy chain variable region CDR3 comprising the amino acid sequence of SEQ ID NO: 17, a light chain variable region CDR1 comprising the amino acid sequence of SEQ ID NO: 24, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 21, a heavy chain variable region CDR3 comprising the amino acid sequence of SEQ ID NO: 17, a light chain variable region CDR1 comprising the amino acid sequence of SEQ ID NO: 25, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 21, a heavy chain variable region CDR3 comprising the amino acid sequence of SEQ ID NO: 17, a light chain variable region CDR1 comprising the amino acid sequence of SEQ ID NO: 26, a light chain variable region CDR2 comprising the amino acid sequence of SEQ ID NO: 19, and a light chain variable region CDR3 comprising the amino acid sequence of SEQ ID NO: 22.

In some aspects, the antibodies specifically bind to TL1A and comprise a heavy chain variable region CDR1 comprising the amino acid sequence of SEQ ID NO: 15, a heavy chain variable region CDR2 comprising the amino acid sequence of SEQ ID NO: 21, a heavy chain variable region CDR3 comprising the amino acid sequence of SEQ ID NO: 17, a light chain variable region CDR1 comprising the amino acid sequence of SEQ ID NO: 18, a light chain variable region CDR2 comprising the amino acid sequence of SEQ ID NO: 19, and a light chain variable region CDR3 comprising the amino acid sequence of SEQ ID NO: 27.

In some aspects, the antibodies specifically bind to TL1A, and comprise a heavy chain variable region comprising the amino acid sequence of SEQ ID NO: 1 and a light chain variable region, provided that the light chain variable region does not comprise the amino acid sequence of SEQ ID NO: 2. In some aspects, the antibodies specifically bind to TL1A, and comprise a heavy chain variable region comprising the amino acid sequence of SEQ ID NO: 3 and a light chain variable region or a light chain. The light chain variable region may further comprise a lambda constant region.

In some aspects, the antibodies specifically bind to TL1A, and comprise a light chain variable region comprising the amino acid sequence of SEQ ID NO: 2 and a heavy chain variable region, provided that the heavy chain variable region does not comprise the amino acid sequence of SEQ ID NO: 1. In some aspects, the antibodies specifically bind to TL1A, and comprise a light chain variable region comprising the amino acid sequence of SEQ ID NO: 4 and a heavy chain variable region. In some aspects, the antibodies specifically bind to TL1A, and comprise a light chain variable region comprising the amino acid sequence of SEQ ID NO: 5 and a heavy chain variable region. In some aspects, the antibodies specifically bind to TL1A, and comprise a light chain variable region comprising the amino acid sequence of SEQ ID NO: 6 and a heavy chain variable region. In some aspects, the antibodies specifically bind to TL1A, and comprise a light chain variable region comprising the amino acid sequence of SEQ ID NO: 7 and a heavy chain variable region. In some aspects, the antibodies specifically bind to TL1A, and comprise a light chain variable region comprising the amino acid sequence of SEQ ID NO: 8 and a heavy chain variable region. In some aspects, the antibodies specifically bind to TL1A, and comprise a light chain variable region comprising the amino acid sequence of SEQ ID NO: 9 and a heavy chain variable region. In some aspects, the antibodies specifically bind to TL1A, and comprise a light chain variable region comprising the amino acid sequence of SEQ ID NO: 10 and a heavy chain variable region. In some aspects, the antibodies specifically bind to TL1A, and comprise a light chain variable region comprising the amino acid sequence of SEQ ID NO: 11 and a heavy chain variable region. In some aspects, the antibodies specifically bind to TL1A, and comprise a light chain variable region comprising the amino acid sequence of SEQ ID NO: 12 and a heavy chain variable region. In some aspects, the antibodies specifically bind to TL1A, and comprise a light chain variable region comprising the amino acid sequence of SEQ ID NO: 13 and a heavy chain variable region. In some aspects, the antibodies specifically bind to TL1A, and comprise a light chain variable region comprising the amino acid sequence of SEQ ID NO: 14 and a heavy chain variable region, provided that if the light chain variable region comprises the amino acid sequence of SEQ ID NO: 2, the heavy chain variable region does not comprise the amino acid sequence of SEQ ID NO: 1. The heavy chain variable region may further comprise a heavy chain constant region, including any IgG1, IgG2, or IgG4 heavy chain constant region amino acid sequence described or exemplified herein.

The 320-179-variant antibodies specifically bind to TL1A. The antibodies bind to human TL1A, and may bind to one or more of cynomolgus monkey TL1A, mouse TL1A, rat TL1A, guinea pig TL1A, cat TL1A, dog TL1A, pig TL1A, or rabbit TL1A. In some aspects, the antibodies may bind to TL1A of multiple different species, for example, if the epitope is shared. In some aspects, human TL1A comprises the amino acid sequence of SEQ ID NO: 31, SEQ ID NO: 32, or SEQ ID NO: 33. In some aspects, cynomolgus monkey TL1A comprises the amino acid sequence of SEQ ID NO: 34. In some aspects, mouse TL1A comprises the amino acid sequence of SEQ ID NO: 35. In some aspects, rat TL1A comprises the amino acid sequence of SEQ ID NO: 36. In some aspects, guinea pig TL1A comprises the amino acid sequence of SEQ ID NO: 37. In some aspects, cat TL1A comprises the amino acid sequence of SEQ ID NO: 38. In some aspects, pig TL1A comprises the amino acid sequence of SEQ ID NO: 39. In some aspects, rabbit TL1A comprises the amino acid sequence of SEQ ID NO: 40. In some aspects, dog TL1A comprises the amino acid sequence of SEQ ID NO: 41.

The 320-179-variant antibodies have a binding affinity for an epitope on TL1A that includes an equilibrium dissociation constant ($K_D$), which can be measured according to a kinetic exclusion assay, such as a KINEXA® assay (Sapidyne Instruments Inc., Boise, Id.). The $K_D$ for TL1A binding determined from a kinetic exclusion assay is preferably less than about 1000 pM. In some aspects, the $K_D$ for TL1A binding determined from a kinetic exclusion assay is less than about 500 pM, or less than about 400 pM, or less than about 300 pM, or less than about 200 pM. In some preferred aspects, the $K_D$ for TL1A binding determined from a kinetic exclusion assay is less than about 100 pM.

The $K_D$ for TL1A binding determined from a kinetic exclusion assay may be from about 10 pM to about 100 pM. The $K_D$ for TL1A binding determined from a kinetic exclusion assay may be from about 25 pM to about 75 pM. The $K_D$ for TL1A binding determined from a kinetic exclusion assay may be from about 30 pM to about 60 pM. The $K_D$ for TL1A binding determined from a kinetic exclusion assay may be from about 30 pM to about 50 pM. The $K_D$ for TL1A binding determined from a kinetic exclusion assay may be from about 35 pM to about 50 pM. The $K_D$ for TL1A binding determined from a kinetic exclusion assay may be from about 36 pM to about 46 pM. The $K_D$ for TL1A binding determined from a kinetic exclusion assay may be from about 38 pM to about 44 pM. The $K_D$ for TL1A binding determined from a kinetic exclusion assay may be from about 39 pM to about 43 pM. The $K_D$ for TL1A binding determined from a kinetic exclusion assay may be from about 40 pM to about 45 pM. The $K_D$ for TL1A binding determined from a kinetic exclusion assay may be from about 35 pM to about 42 pM. The $K_D$ for TL1A binding determined from a kinetic exclusion assay may about 40 pM. The $K_D$ for TL1A binding determined from a kinetic exclusion assay may about 41 pM. The $K_D$ for TL1A binding determined from a kinetic exclusion assay may about 42 pM. The kinetic exclusion assay may use the antibody molecule or TL1A molecule as the constant binding partner, and the other molecule as the titrant.

The 320-179-variant anti-TL1A antibodies are preferably capable of binding to TL1A-positive cells. The antibody may bind to a TL1A-positive cell with an $EC_{50}$ value of less than about 100 nM. The antibody may bind to a TL1A-positive cell with an $EC_{50}$ value of less than about 75 nM. The antibody may bind to a TL1A-positive cell with an $EC_{50}$ value of less than about 50 nM. The antibody may bind to a TL1A-positive cell with an $EC_{50}$ value of less than about 30 nM. The antibody may bind to a TL1A-positive cell with an $EC_{50}$ value of less than about 25 nM. The antibody may bind to a TL1A-positive cell with an $EC_{50}$ value of less than about 20 nM. The antibody may bind to a TL1A-positive cell with an $EC_{50}$ value of less than about 18 nM. The antibody may bind to a TL1A-positive cell with an $EC_{50}$ value of less than about 15 nM. The antibody may bind to a TL1A-positive cell with an $EC_{50}$ value of less than about 13 nM. The antibody may bind to a TL1A-positive cell with an $EC_{50}$ value of less than about 10 nM.

The 320-179-variant antibodies preferably are monoclonal, and more preferably are full length antibodies comprising two heavy chains and two light chains. In some aspects, the antibodies comprise derivatives or fragments or portions of antibodies that retain the antigen-binding specificity, and also preferably retain most or all of the affinity, of the 320-179 parent antibody molecule (e.g., for TL1A). For example, derivatives may comprise at least one variable region (either a heavy chain or light chain variable region). Other examples of suitable antibody derivatives and fragments include, without limitation, antibodies with polyepitopic specificity, bispecific antibodies, multi-specific antibodies, diabodies, single-chain molecules, as well as FAb, F(Ab')2, Fd, Fabc, and Fv molecules, single chain (Sc) antibodies, single chain Fv antibodies (scFv), individual antibody light chains, individual antibody heavy chains, fusions between antibody chains and other molecules, heavy chain monomers or dimers, light chain monomers or dimers, dimers consisting of one heavy and one light chain, and other multimers. Single chain Fv antibodies may be multivalent. All antibody isotypes may be used to produce antibody derivatives, fragments, and portions. Antibody derivatives, fragments, and/or portions may be recombinantly produced and expressed by any cell type, prokaryotic or eukaryotic.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Typically, the antigen binding properties of an antibody are less likely to be disturbed by changes to FR sequences than by changes to the CDR sequences. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The 320-179-variant antibodies are fully human. Fully human antibodies are those where the whole molecule is human or otherwise of human origin, or includes an amino acid sequence identical to a human form of the antibody. Fully human antibodies include those obtained from a human V gene library, for example, where human genes encoding variable regions of antibodies are recombinantly expressed. Fully human antibodies may be expressed in other organisms (e.g., mice and xenomouse technology) or cells from other organisms transformed with genes encoding human antibodies. Fully human antibodies may nevertheless include amino acid residues not encoded by human sequences, e.g., mutations introduced by random or site directed mutations.

In some aspects, the 320-179-variant antibodies may comprise non-immunoglobulin derived protein frameworks. For example, reference may be made to (Ku & Schutz, 1995, Proc. Natl. Acad. Sci. USA 92: 6552-6556) which describes a four-helix bundle protein cytochrome b562 having two loops randomized to create CDRs, which have been selected for antigen binding.

The 320-179-variant antibodies may comprise post-translational modifications or moieties, which may impact antibody activity or stability. These modifications or moieties include, but are not limited to, methylated, acetylated, glycosylated, sulfated, phosphorylated, carboxylated, and amidated moieties and other moieties that are well known in the art. Moieties include any chemical group or combinations of groups commonly found on immunoglobulin molecules in nature or otherwise added to antibodies by recombinant expression systems, including prokaryotic and eukaryotic expression systems.

Examples of side chain modifications contemplated by the disclosure include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivation, for example, to a corresponding amide. Sulfydryl groups may be modified by methods such as carboxymethylation with iodoacetic acid or iodoacetamide; performic acid oxidation to cysteic acid; formation of mixed disulfides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuri-4-nitrophenol and other mercurials; carbamoylation with cyanate at alkaline pH. Tryptophan residues may be modified by, for example, oxidation with N-bromosuccinimide or alkylation of the indole ring with 2-hydroxy-5-nitrobenzyl bromide or sulfenyl halides. Tyrosine residues on the other hand, may be altered by nitration with tetranitromethane to form a 3-nitrotyrosine derivative. Modification of the imidazole ring of a histidine residue may be accomplished by alkylation with iodoacetic acid derivatives or N-carbethoxylation with diethylpyrocarbonate.

The 320-179-variant antibodies may include modifications that modulate serum half-life and biodistribution, including without limitation, modifications that modulate the antibody's interaction with the neonatal Fc receptor (FcRn), a receptor with a key role in protecting IgG from catabolism, and maintaining high serum antibody concentration. Serum half-life modulating modifications may occur in the Fc region of IgG1, IgG2, or IgG4, including the triple substitution of M252Y/S254T/T256E (the "YTE" substitutions, with numbering according to the EU numbering system (Edelman, G. M. et al. (1969) Proc. Natl. Acad. USA 63, 78-85)), as described in U.S. Pat. No. 7,083,784. Other substitutions may occur at positions 250 and 428, see e.g., U.S. Pat. No. 7,217,797, as well as at positions 307, 380 and 434, see, e.g., PCT Publ. No. WO 00/042072. Examples of constant domain amino acid substitutions which modulate binding to Fc receptors and subsequent function mediated by these receptors, including FcRn binding and serum half-life, are described in U.S. Publ. Nos. 2009/0142340, 2009/0068175, and 2009/0092599. Antibodies of any class may have the heavy chain C-terminal lysine omitted or removed to reduce heterogeneity (ΔK). The substitution of S228P (EU numbering) in the human IgG4 can stabilize antibody Fab-arm exchange in vivo (Labrin et al. (2009) Nature Biotechnology 27:8; 767-773), and this substitution may be present at the same time as the YTE and/or AK modifications.

The 320-179-variant antibodies comprise human constant domains. The heavy chain constant domains preferably are human IgG1, IgG2, or IgG4 constant domains. The light chain constant domains preferably are human lambda constant domains. A suitable human lambda domain comprises SEQ ID NO: 48.

Human heavy chain IgG1 constant regions that may be used with the 320-179 variant antibodies may be selected from among human IgG1 (SEQ ID NO: 42), human IgG1 (ΔK) (SEQ ID NO: 43), human IgG1 252Y/254T/256E (SEQ ID NO: 44), human IgG1 252Y/254T/256E (ΔK) (SEQ ID NO: 64), human IgG1 L234A/L235A/G237A (SEQ ID NO: 63), human IgG1 L234A/L235A/G237A (ΔK) (SEQ ID NO: 62), human IgG1 L235A/G237A (SEQ ID NO: 65), and human IgG1 L235A/G237A (ΔK) (SEQ ID NO: 66). Human heavy chain IgG2 constant regions that may be used with the 320-179 variant antibodies may be selected from among human IgG2 with or without ΔK (SEQ ID NO: 67 and SEQ ID NO: 70) and human IgG2 A330S/P331S with or without (ΔK) (SEQ ID NO: 71 and SEQ ID NO: 68). Human heavy chain IgG4 constant regions that may be used with the 320-179 variant antibodies may be selected from among human IgG4 S228P (SEQ ID NO: 45), human IgG4 S228P (ΔK) (SEQ ID NO: 46), human IgG4 228P/252Y/254T/256E (SEQ ID NO: 47), and human IgG4 228P/252Y/254T/256E (ΔK) (SEQ ID NO: 69).

The 320-179-variant antibodies may be labelled, bound, or conjugated to any chemical or biomolecule moieties. Labelled antibodies may find use in therapeutic, diagnostic, or basic research applications. Such labels/conjugates can be detectable, such as fluorochromes, electrochemiluminescent probes, quantum dots, radiolabels, enzymes, fluorescent proteins, luminescent proteins, and biotin. The labels/conjugates may be chemotherapeutic agents, toxins, isotopes, and other agents used for treating conditions such as the killing of cancer cells. Chemotherapeutic agents may be any which are suitable for the purpose for which the antibody is being used.

The antibodies may be derivatized by known protecting/blocking groups to prevent proteolytic cleavage or enhance activity or stability.

Polynucleotide sequences that encode antibodies and their subdomains (e.g., FRs and CDRs) are featured in the disclosure. Polynucleotides include, but are not limited to, RNA, DNA, cDNA, hybrids of RNA and DNA, and single, double, or triple stranded strands of RNA, DNA, or hybrids thereof. Polynucleotides may comprise a nucleic acid sequence encoding the heavy chain variable region and/or the light chain variable region of a 320-179 variant antibody as described or exemplified herein. Complements of the polynucleotide sequences are also within the scope of the disclosure.

A polynucleotide may comprise a nucleic acid sequence encoding an antibody heavy chain variable region comprising the amino acid sequence of SEQ ID NO: 3. A polynucleotide encoding the amino acid sequence of SEQ ID NO: 3 may comprise the nucleic acid sequence of SEQ ID NO: 51.

A polynucleotide may comprise a nucleic acid sequence encoding an antibody heavy chain variable region comprising the amino acid sequence of SEQ ID NO: 1. A polynucleotide encoding the amino acid sequence of SEQ ID NO: 1 may comprise the nucleic acid sequence of SEQ ID NO: 49.

A polynucleotide may comprise a nucleic acid sequence encoding an antibody light chain variable region comprising the amino acid sequence of SEQ ID NO: 2. A polynucleotide encoding the amino acid sequence of SEQ ID NO: 2 may comprise the nucleic acid sequence of SEQ ID NO: 50.

A polynucleotide may comprise a nucleic acid sequence encoding an antibody light chain variable region comprising the amino acid sequence of SEQ ID NO: 4. A polynucleotide encoding the amino acid sequence of SEQ ID NO: 4 may comprise the nucleic acid sequence of SEQ ID NO: 52.

A polynucleotide may comprise a nucleic acid sequence encoding an antibody light chain variable region comprising the amino acid sequence of SEQ ID NO: 5. A polynucleotide encoding the amino acid sequence of SEQ ID NO: 5 may comprise the nucleic acid sequence of SEQ ID NO: 53.

A polynucleotide may comprise a nucleic acid sequence encoding an antibody light chain variable region comprising the amino acid sequence of SEQ ID NO: 6. A polynucleotide encoding the amino acid sequence of SEQ ID NO: 6 may comprise the nucleic acid sequence of SEQ ID NO: 54.

A polynucleotide may comprise a nucleic acid sequence encoding an antibody light chain variable region comprising the amino acid sequence of SEQ ID NO: 7. A polynucleotide encoding the amino acid sequence of SEQ ID NO: 7 may comprise the nucleic acid sequence of SEQ ID NO: 55.

A polynucleotide may comprise a nucleic acid sequence encoding an antibody light chain variable region comprising the amino acid sequence of SEQ ID NO: 8. A polynucleotide encoding the amino acid sequence of SEQ ID NO: 8 may comprise the nucleic acid sequence of SEQ ID NO: 56.

A polynucleotide may comprise a nucleic acid sequence encoding an antibody light chain variable region comprising the amino acid sequence of SEQ ID NO: 10. A polynucleotide encoding the amino acid sequence of SEQ ID NO: 10 may comprise the nucleic acid sequence of SEQ ID NO: 57.

In some aspects, a polynucleotide comprises a first nucleic acid sequence encoding an antibody heavy chain variable region and a second nucleic acid sequence encoding an antibody light chain variable region. A first nucleic acid sequence may encode an antibody heavy chain variable region comprising the amino acid sequence of SEQ ID NO: 3 and a light chain variable region comprising the amino acid sequence of SEQ ID NO: 2. A polynucleotide encoding the amino acid sequence of SEQ ID NO: 3 may comprise the nucleic acid sequence of SEQ ID NO: 51 and a polynucleotide encoding the amino acid sequence of SEQ ID NO: 2 may comprise the nucleic acid sequence of SEQ ID NO: 50.

A first nucleic acid sequence may encode an antibody heavy chain variable region comprising the amino acid sequence of SEQ ID NO: 3 and a light chain variable region comprising the amino acid sequence of SEQ ID NO: 4. A polynucleotide encoding the amino acid sequence of SEQ ID NO: 3 may comprise the nucleic acid sequence of SEQ ID NO: 51 and a polynucleotide encoding the amino acid sequence of SEQ ID NO: 4 may comprise the nucleic acid sequence of SEQ ID NO: 52.

A first nucleic acid sequence may encode an antibody heavy chain variable region comprising the amino acid sequence of SEQ ID NO: 3 and a light chain variable region comprising the amino acid sequence of SEQ ID NO: 6. A polynucleotide encoding the amino acid sequence of SEQ ID NO: 3 may comprise the nucleic acid sequence of SEQ ID NO: 51 and a polynucleotide encoding the amino acid sequence of SEQ ID NO: 6 may comprise the nucleic acid sequence of SEQ ID NO: 54.

A first nucleic acid sequence may encode an antibody heavy chain variable region comprising the amino acid sequence of SEQ ID NO: 3 and a light chain variable region comprising the amino acid sequence of SEQ ID NO: 7. A polynucleotide encoding the amino acid sequence of SEQ ID NO: 3 may comprise the nucleic acid sequence of SEQ ID NO: 51 and a polynucleotide encoding the amino acid sequence of SEQ ID NO: 7 may comprise the nucleic acid sequence of SEQ ID NO: 55.

A first nucleic acid sequence may encode an antibody heavy chain variable region comprising the amino acid sequence of SEQ ID NO: 3 and a light chain variable region comprising the amino acid sequence of SEQ ID NO: 8. A polynucleotide encoding the amino acid sequence of SEQ ID NO: 3 may comprise the nucleic acid sequence of SEQ ID NO: 51 and a polynucleotide encoding the amino acid sequence of SEQ ID NO: 8 may comprise the nucleic acid sequence of SEQ ID NO: 56.

A first nucleic acid sequence may encode an antibody heavy chain variable region comprising the amino acid sequence of SEQ ID NO: 3 and a light chain variable region comprising the amino acid sequence of SEQ ID NO: 10. A polynucleotide encoding the amino acid sequence of SEQ ID NO: 3 may comprise the nucleic acid sequence of SEQ ID NO: 51 and a polynucleotide encoding the amino acid sequence of SEQ ID NO: 10 may comprise the nucleic acid sequence of SEQ ID NO: 57.

A first nucleic acid sequence may encode an antibody heavy chain variable region comprising the amino acid sequence of SEQ ID NO: 1 and a light chain variable region comprising the amino acid sequence of SEQ ID NO: 4. A polynucleotide encoding the amino acid sequence of SEQ ID NO: 1 may comprise the nucleic acid sequence of SEQ ID NO: 49 and a polynucleotide encoding the amino acid sequence of SEQ ID NO: 4 may comprise the nucleic acid sequence of SEQ ID NO: 52.

A first nucleic acid sequence may encode an antibody heavy chain variable region comprising the amino acid sequence of SEQ ID NO: 1 and a light chain variable region comprising the amino acid sequence of SEQ ID NO: 5. A polynucleotide encoding the amino acid sequence of SEQ ID NO: 1 may comprise the nucleic acid sequence of SEQ ID NO: 49 and a polynucleotide encoding the amino acid sequence of SEQ ID NO: 5 may comprise the nucleic acid sequence of SEQ ID NO: 53.

A first nucleic acid sequence may encode an antibody heavy chain variable region comprising the amino acid sequence of SEQ ID NO: 1 and a light chain variable region comprising the amino acid sequence of SEQ ID NO: 6. A polynucleotide encoding the amino acid sequence of SEQ ID NO: 1 may comprise the nucleic acid sequence of SEQ ID NO: 49 and a polynucleotide encoding the amino acid sequence of SEQ ID NO: 6 may comprise the nucleic acid sequence of SEQ ID NO: 54.

A first nucleic acid sequence may encode an antibody heavy chain variable region comprising the amino acid sequence of SEQ ID NO: 1 and a light chain variable region comprising the amino acid sequence of SEQ ID NO: 7. A polynucleotide encoding the amino acid sequence of SEQ ID NO: 1 may comprise the nucleic acid sequence of SEQ ID NO: 49 and a polynucleotide encoding the amino acid sequence of SEQ ID NO: 7 may comprise the nucleic acid sequence of SEQ ID NO: 55.

A first nucleic acid sequence may encode an antibody heavy chain variable region comprising the amino acid sequence of SEQ ID NO: 1 and a light chain variable region comprising the amino acid sequence of SEQ ID NO: 8. A polynucleotide encoding the amino acid sequence of SEQ ID NO: 1 may comprise the nucleic acid sequence of SEQ ID NO: 49 and a polynucleotide encoding the amino acid sequence of SEQ ID NO: 8 may comprise the nucleic acid sequence of SEQ ID NO: 56.

In some aspects, a polynucleotide comprises a first nucleic acid sequence encoding an antibody heavy chain variable region and a second nucleic acid sequence encoding a heavy chain constant region. In preferred aspects, a polynucleotide comprises a first nucleic acid sequence encoding an antibody heavy chain variable region comprising the amino acid sequence of SEQ ID NO: 3 and a second nucleic acid sequence encoding an IgG1(ΔK) heavy chain constant region of SEQ ID NO: 43, for example, a polynucleotide comprising the nucleic acid sequence of SEQ ID NO: 58.

In some aspects, a polynucleotide comprises a first nucleic acid sequence encoding an antibody light chain variable region and a second nucleic acid sequence encoding a light chain constant region. In preferred aspects, a polynucleotide comprises a first nucleic acid sequence encoding an antibody light chain variable region comprising the amino acid sequence of SEQ ID NO: 4 and a second nucleic acid sequence encoding a lambda light chain constant region of SEQ ID NO: 48, for example, a polynucleotide comprising the nucleic acid sequence of SEQ ID NO: 59.

Any of the polynucleotides described or exemplified herein may be comprised within a vector. Thus, vectors comprising polynucleotides are provided as part of the disclosure. The vectors may be expression vectors. Recombinant expression vectors containing a sequence encoding a polypeptide of interest are thus provided. The expression vector may contain one or more additional sequences, such as but not limited to regulatory sequences, a selection marker, a purification tag, or a polyadenylation signal. Such regulatory elements may include a transcriptional promoter, enhancers, mRNA ribosomal binding sites, or sequences that control the termination of transcription and translation.

Expression vectors, especially mammalian expression vectors, may include one or more nontranscribed elements, such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a specific host may also be incorporated.

The vectors may be used to transform any of a wide array of host cells well known to those of skill in the art, and preferably host cells capable of expressing antibodies. Vectors include without limitation, plasmids, phagemids, cosmids, bacmids, bacterial artificial chromosomes (BACs), yeast artificial chromosomes (YACs), and baculovirus, as well as other bacterial, eukaryotic, yeast, and viral vectors. Suitable host cells include without limitation CHO cells, NSO cells, HEK293 cells, or any eukaryotic stable cell line known or produced, and also include bacteria, yeast, and insect cells.

The antibodies may also be produced by hybridoma cells; methods to produce hybridomas being well known and established in the art.

The disclosure also provides compositions comprising the 320-179 variant antibodies. The compositions may comprise any of the antibodies described and/or exemplified herein and an acceptable carrier such as a pharmaceutically acceptable carrier. Suitable carriers include any media that does not interfere with the biological activity of the antibody and preferably is not toxic to a host to which it is administered. The compositions may be formulated for administration to a subject in any suitable dosage form.

The 320-179 variant antibodies may be used to treat a respiratory tract disease, a gastrointestinal disease, arthritis, or a skin disease in a subject. Thus, the disclosure features treatment methods. In general, the methods comprise administering a 320-179 variant antibody, or composition thereof, to a subject in need of treatment for a respiratory tract disease, gastrointestinal disease, arthritis, or a skin disease, such that the respiratory tract disease, gastrointestinal disease, arthritis, or skin disease is treated. The 320-179 variant antibody may comprise any antibody described or exemplified herein. Administering may comprise subcutaneously administering the antibody. Administering may comprise intravenously administering the antibody. The subject is preferably a human being. The subject may be a non-human primate such as a cynomolgus monkey, or may be a mammal such as a mouse, rat, guinea pig, cat, pig, rabbit, or dog.

In aspects where a respiratory tract disease is to be treated, the methods comprise administering a 320-179 variant antibody, or composition thereof, to a subject in need of treatment for a respiratory tract disease. The respiratory tract disease may comprise one or more of asthma, chronic obstructive pulmonary disease (COPD), pulmonary fibrosis, pulmonary sarcoidosis, allergic rhinitis, or cystic fibrosis. Thus, for example, in some aspects, the methods comprise administering a 320-179 variant antibody, or composition thereof, to a subject in need of treatment for asthma, such that the asthma is treated in the subject. In some aspects, the methods comprise administering a 320-179 variant antibody, or composition thereof, to a subject in need of treatment for COPD, such that the COPD is treated in the subject. In some aspects, the methods comprise administering a 320-179 variant antibody, or composition thereof, to a subject in need of treatment for pulmonary fibrosis, such that the pulmonary fibrosis is treated in the subject. In some aspects, the methods comprise administering a 320-179 variant antibody, or composition thereof, to a subject in need of treatment for pulmonary sarcoidosis, such that the pulmonary sarcoidosis is treated in the subject. In some aspects, the methods comprise administering a 320-179 variant antibody, or composition thereof, to a subject in need of treatment for allergic rhinitis, such that the allergic rhinitis is treated in the subject. In some aspects, the methods comprise administering a 320-179 variant antibody, or composition thereof, to a subject in need of treatment for cystic fibrosis, such that the cystic fibrosis is treated in the subject.

In aspects where a gastrointestinal disease is to be treated, the methods comprise administering a 320-179 variant antibody, or composition thereof, to a subject in need of treatment for a gastrointestinal disease. The gastrointestinal disease may comprise one or more of inflammatory bowel disease (IBD), Crohn's disease, colitis, ulcerative colitis, irritable bowel syndrome (IBS), eosinophilic esophagitis, or a gastrointestinal disease or condition associated with cystic fibrosis. Thus, for example, in some aspects, the methods comprise administering a 320-179 variant antibody, or composition thereof, to a subject in need of treatment for IBD, such that the IBD is treated in the subject. In some aspects, the methods comprise administering a 320-179 variant antibody, or composition thereof, to a subject in need of treatment for Crohn's disease, such that the Crohn's disease is treated in the subject. In some aspects, the methods comprise administering a 320-179 variant antibody, or composition thereof, to a subject in need of treatment for colitis, such that the colitis is treated in the subject. In some aspects, the methods comprise administering a 320-179 variant antibody, or composition thereof, to a subject in need of treatment for ulcerative colitis, such that the ulcerative colitis is treated in the subject. In some aspects, the methods comprise administering a 320-179 variant antibody, or composition thereof, to a subject in need of treatment for IBS, such that the IBS is treated in the subject. In some aspects, the methods comprise administering a 320-179 variant antibody, or composition thereof, to a subject in need of treatment for eosinophilic esophagitis, such that the eosinophilic esophagitis is treated in the subject. In some aspects, the methods comprise administering a 320-179 variant antibody, or composition thereof, to a subject in need of treatment for a gastrointestinal disease or condition associated with cystic fibrosis, such that the gastrointestinal disease or condition associated with cystic fibrosis is treated in the subject.

In aspects where arthritis is to be treated, the methods comprise administering a 320-179 variant antibody, or composition thereof, to a subject in need of treatment for arthritis. The arthritis may comprise rheumatoid arthritis. Thus, for example, in some aspects, the methods comprise administering a 320-179 variant antibody, or composition thereof, to a subject in need of treatment for rheumatoid arthritis, such that the rheumatoid arthritis is treated in the subject.

In aspects where a skin disease is to be treated, the methods comprise administering a 320-179 variant antibody, or composition thereof, to a subject in need of treatment for a skin disease. The skin disease may comprise one or more of atopic dermatitis, eczema, or scleroderma. Thus, for example, in some aspects, the methods comprise administering a 320-179 variant antibody, or composition thereof, to a subject in need of treatment for atopic dermatitis, such that the atopic dermatitis is treated in the subject. In some aspects, the methods comprise administering a 320-179 variant antibody, or composition thereof, to a subject in need of treatment for eczema, such that the eczema is treated in the subject. In some aspects, the methods comprise administering a 320-179 variant antibody, or composition thereof, to a subject in need of treatment for scleroderma, such that the scleroderma is treated in the subject.

The 320-179 variant antibodies described or exemplified herein may be used in the preparation of a medicament for use in the treatment of a respiratory tract disease. The 320-179 variant antibodies described or exemplified herein may be used in the preparation of a medicament for use in the treatment of a gastrointestinal disease. The 320-179 variant antibodies described or exemplified herein may be used in the preparation of a medicament for use in the treatment of arthritis. The 320-179 variant antibodies described or exemplified herein may be used in the preparation of a medicament for use in the treatment of a skin disease. The 320-179 variant antibodies described or exemplified herein may be used in the preparation of a medicament for use in the treatment of any one of asthma, COPD, pulmonary fibrosis, pulmonary sarcoidosis, allergic rhinitis, cystic fibrosis, inflammatory bowel disease, Crohn's disease, colitis, ulcerative colitis, irritable bowel syndrome, eosinophilic esophagitis, a gastrointestinal disease or condition associated with cystic fibrosis, arthritis, rheumatoid arthritis, atopic dermatitis, eczema, or scleroderma.

The 320-179 variant antibodies described or exemplified herein may be for use in the treatment of a respiratory tract disease. The 320-179 variant antibodies described or exemplified herein may be for use in the treatment of a gastrointestinal disease. The 320-179 variant antibodies described or exemplified herein may be for use in the treatment of asthma. The 320-179 variant antibodies described or exemplified herein may be for use in the treatment of a skin disease. The 320-179 variant antibodies described or exemplified herein may be for use in the treatment of COPD. The 320-179 variant antibodies described or exemplified herein may be for use in the treatment of pulmonary fibrosis. The 320-179 variant antibodies described or exemplified herein may be for use in the treatment of pulmonary sarcoidosis. The 320-179 variant antibodies described or exemplified herein may be for use in the treatment of allergic rhinitis. The 320-179 variant antibodies described or exemplified herein may be for use in the treatment of cystic fibrosis. The 320-179 variant antibodies described or exemplified herein may be for use in the treatment of inflammatory bowel disease. The 320-179 variant antibodies described or exemplified herein may be for use in the treatment of Crohn's disease. The 320-179 variant antibodies described or exemplified herein may be for use in the treatment of colitis. The 320-179 variant antibodies described or exemplified herein may be for use in the treatment of ulcerative colitis. The 320-179 variant antibodies described or exemplified herein may be for use in the treatment of eosinophilic esophagitis. The 320-179 variant antibodies described or exemplified herein may be for use in the treatment of a gastrointestinal disease or condition associated with cystic fibrosis. The 320-179 variant antibodies described or exemplified herein may be for use in the treatment of irritable bowel syndrome. The 320-179 variant antibodies described or exemplified herein may be for use in the treatment of rheumatoid arthritis. The 320-179 variant antibodies described or exemplified herein may be for use in the treatment of atopic dermatitis. The 320-179 variant antibodies described or exemplified herein may be for use in the treatment of eczema. The 320-179 variant antibodies described or exemplified herein may be for use in the treatment of scleroderma.

Also provided is an in vitro method for detecting TL1A in a tissue sample isolated from a subject, comprising contacting the antibody according to any one of claims 1-19 with a tissue sample isolated from a subject to form an antibody-TL1A complex, and detecting the complex in the tissue sample.

A 320-179 variant antibody may be used to detect TL1A-positive cells, for example, in a tissue sample obtained from a subject. The antibodies may be used to detect TL1A-positive peripheral blood mononuclear cells (PBMCs), for example, PBMCs obtained from a subject. The antibodies may be used to detect TL1A in the blood serum. Such methods may be carried out in vivo, ex vivo, in vitro, or in situ. In general, the methods comprise contacting any of the 320-179 variant antibodies described or exemplified herein with a tissue or cells, e.g., PBMCs, isolated from a subject to form an antibody-TL1A complex, and detecting the complex in the tissue or on the cells. The antibody may be labelled with a detectable label. The antibody may be detected with a secondary antibody that is labelled with a detectable label. The tissue may comprise or may be a biological fluid such as blood or blood serum. The tissue may comprise or may be respiratory tract tissue, such as lung tissue, sputum, bronchoalveolar lavage fluid, gastrointestinal tissue, or gastrointestinal lavage fluid. The tissue may comprise or may be skin or dermal tissue. The tissue may comprise or may be tissue of any joint in the body. The method may further comprise isolating the tissue from the subject. Such methods may be quantitative, for example, by quantifying the level of TL1A in the tissue, by quantifying the level of TL1A-positive cells, or by quantifying the level of TL1A on cells, or by quantifying the level of TL1A in the serum.

The disclosure also features kits comprising any of the 320-179 variant antibodies described and exemplified herein. The kits may be used to supply antibodies and other agents for use in diagnostic, basic research, or therapeutic methods, among others. In some aspects, the kits comprise any one or more of the 320-179 variant antibodies described or exemplified herein and instructions for using the one or more antibodies in a method for treating a respiratory tract disease, in a method for treating a gastrointestinal disease, or in a method for treating arthritis.

The following examples are provided to describe the disclosure in greater detail. They are intended to illustrate, not to limit, the disclosure.

EXAMPLE 1

Materials and Methods

Amino acid positions in these examples are numbered according to the Kabat numbering system. CDRs are defined according to the AbM method of CDR definition system throughout this document.

1.1. Generation of variant bundles. The heavy- and light chain variable region amino acid sequences of antibody 320-179 (SEQ ID NOs: 1 and 2 respectively) were used as templates for the design of point variants. 320-179 has been previously described in U.S. Publ. No. 2014/0255302 (VH is SEQ ID NO: 186 and VL is SEQ ID NO: 199 in that publication) as 320-179 (also described as C320-179). This antibody had favorable biophysical properties, was a potent inhibitor of TL1A and had a low predicted immunogenicity profile.

Antibody variants of 320-179 were made by substituting one of a group of nine representative amino acids—A, S, Q, D, H, K, L, W, Y—one at a time at one of each CDR amino acid position (as defined by AbM nomenclature) in the light chain CDR1 (CDR-L1), the light chain CDR3 (CDR-L3), the heavy chain CDR1 (CDR-H1) and the heavy chain CDR2 (CDR-H2). Antibody variants, incorporating A, S, Q, D, H, K, L, W, Y, were also made at position 59 and 60 in the variable heavy chain and at position 79 in the variable light chain. A complete list of all single substituted antibody variants generated is shown in FIG. 1 (variable heavy chain) and 2 (variable light chain), respectively.

1.2. Construction of Vectors Expressing Antibodies. Variable region variants were generated by back-translation of amino acid sequences into DNA sequences which were subsequently synthesized de novo by assembly of synthetic oligonucleotides. $V_H$ variants were subcloned into a mammalian expression vector containing a human constant region to produce full-length antibody heavy chains (human IgG1 heavy chain $C_H1$, hinge, $C_H2$ and $C_H3$ domains) (e.g., UniProt No. P01857). Similarly, $V_L$ variants were subcloned into a mammalian expression vector containing a human lambda light chain constant region to produce full-length antibody lambda chains (SwissProt No. POCG05.1). In some instances, the full-length heavy chain and, separately, light chain, was back-translated into DNA sequences and subsequently synthesized de novo by assembly of synthetic oligonucleotides.

1.3. Expression of antibody variants. Antibodies were produced by co-transfecting antibody heavy- and light chains into EXP1293® cells (Life Technologies, Carlsbad, Calif.). The day before transfection, the number of cells needed for the experiment was determined. For each 20 mL transfection, $3.6 \times 10^7$ cells were required in 20 mL of EXP1293® Expression Medium. On the day prior to transfection, cells were seeded at a density of $0.9 \times 10^6$ viable cells/mL and incubated overnight at 37° C. in a humidified atmosphere of 8% $CO_2$ in air on an orbital shaker rotating at 200 rpm. On the day of transfection, the cell number and viability were determined using an automated cell counter. Only cultures with >98% viable cells were used. For each 20 mL transfection, lipid-DNA complexes were prepared by diluting 10 μg of heavy chain DNA and 10 μg of light chain DNA in OPTI-MEM® (Life Technologies, Carlsbad, Calif.) I Reduced Serum Medium (Cat. no. 31985-062) to a total volume of 1.0 mL. 54 μl of EXPIFECTAMINE® 293 Reagent (Life Technologies, Carlsbad, Calif.) was diluted in OPTI-MEM® I medium to a total volume of 1.0 mL. Both vials were mixed gently and incubated for 5 minutes at room temperature. Following incubation, the diluted DNA was mixed with the diluted EXPIFECTAMINE® 293 Reagent and the DNA-EXPIFECTAMINE® 293 Reagent mixture and incubated a further 20 minutes at room temperature to allow the formation of DNA-EXPIFECTAMINE® 293 Reagent complexes. Following incubation, 2 mL of DNA-EXPIFECTAMINE® 293 Reagent complex was added to each 50 mL bioreactor tube (TPP Techno Plastic Products AG). To the negative control tube, 2 mL of OPTI-MEM® (Life Technologies, Carlsbad, Calif.) I medium was added instead of DNA-EXPIFECTAMINE® 293 Reagent complex. The cells were incubated in a 37° C. incubator with a humidified atmosphere of 8% $CO_2$ in air on an orbital shaker rotating at 200 rpm. Approximately 16-18 hours post-transfection, 100 μl of EXPIFECTAMINE® 293 Transfection Enhancer 1 and 1.0 mL of EXPIFECTAMINE® 293 Transfection Enhancer 2 were added to each bioreactor. Antibodies were harvested at approximately 72 hours post-transfection.

1.4. Purification of antibody variants. Each antibody variant was expressed in EXPI293® cells in 20 mL of cell culture. Cultures were spun down in 50 mL falcon tubes at 3000×g for 20 minutes, and supernatants were filtered using a 0.22 μm filter (Corning). Supernatants were purified using a Gilson ASPEC GX274 robot. Briefly, SPE cartridges (Agilent, 12131014) packed with 1.2 mL MABSELECT SURE® protein A (GE Healthcare Bio-Sciences AB Uppsala, Sweden) resin were pre-equilibrated with 3 column volumes of 1×PBS. 18 mL of supernatant was run over the columns followed by a 4 ml 1×PBS wash. Each column was pre-eluted with 0.9 mL of 0.1 M citric acid, pH 2.9. Purified antibodies were eluted with 2 mL 0.1 M citric acid, pH 2.9. Antibodies were desalted into Sdrensens PBS (59.5 mM $KH_2PO_4$, 7.3 mM $Na_2HPO_4.2H_2O$, 145.4 mM NaCl (pH~5.8)) using PD-10 columns (GE Healthcare).

1.5. Antibody expression and antigen binding as determined by SPR. Using a CM5 sensor chip (GE Healthcare) Protein A (Pierce) was coupled to the chip surface using an amine coupling kit (GE Healthcare). Protein A was coupled on flow cell 1 and 2 (or alternatively 3 and 4) using a BIACORE® T200. Supernatants from EXPI-293® cells containing antibody or alternatively purified antibodies (as described in 1.4) were passed over the surface of flow cell 2, while buffer (HBS-EP) was passed over flow cell 1. The amount of supernatant or purified protein (as well as the concentration) injected during the capture stage varied between runs and is specified in the header of the Tables 3-11. At the end of injection of the supernatant or purified antibody the change in response units was measured. This value was reported as Capture Level in Tables 3-11. To determine if the antibody bound TL1A, the TL1A was then passed over flow cells 1 and 2 and the response units measured prior to the end of the injection of TL1A (the association phase). This value is labeled as TL1A Binding Level (Early) in Tables 3-11. The response units were measured prior to the end of the dissociation phase. This value is labeled as TL1A Binding Level (Late) in Tables 3-11 and is a measure of the amount of antibody that has been lost from the surface of the chip as a result of dissociation of the TL1A-antibody complex. The sensorgrams were double referenced (flow cell 2 is subtracted from flow cell 1 and a buffer blank). As there were a large number of antibody variants to screen, these were screened across different runs (Tables 3-11). In each case (except Run 3) the parent antibody, 320-179 was included in the run, for comparison purposes. A summary of the conditions used in each run is below:

TABLE 1

| Run # | Supernatant | Protein | Approximate capture level (RU) | Conc. TL1A sample (ug/mL) | TL1A Binding Level (Early) timepoint | TL1A Binding Level (Late) timepoint | Notes |
|---|---|---|---|---|---|---|---|
| 1 | | x | 400 | 10 | 59 | 590 | Antibody diluted to 2 ug/mL, variable capture time |
| 2 | x | | 1000 | 10 | 44 | 220 | Supernatant diluted into running buffer, variable capture times |
| 2 | | x | 400 | 10 | 44 | 590 | Antibody diluted 2 ug/mL, variable capture time |
| 3 | x | | variable | 10 | 59 | 590 | Supernatant diluted into running buffer, 60 s capture |
| 4 | | x | 500 | 5 | 44 | 220 | Antibody diluted to 2 ug/mL into running buffer |
| 5 | x | | 100 | 5 | 44 | 220 | Supernatant diluted into running buffer, |
| 6 | | x | variable | 5 | 44 | 170 | Antibody diluted to 2 ug/mL into running buffer and captured for 45 s |
| 7* | | x | 400 | 5 | 44 | 220 | Antibody diluted to approx. 2 ug/mL |
| 8 | | x | 400 | 5 | 44 | 590 | Antibody diluted to 2 ug/mL, variable capture time |
| 9 | | x | 400 | 5 | 44 | 590 | Antibody diluted to 2 ug/mL, variable capture time |

*This run was performed on a Biacore ® A100

The binding of anti-TL1A to different species TL1A was also determined using SPR. The anti-TL1A antibody was captured on the surface of a Protein A. TL1A from either human, rat, mouse, rabbit, guinea pig, pig, dog, cat or cynomolgus monkey were flowed over the surface and the response units measured.

1.6. Production of TL1A. Human TL1A was produced in the mammalian EXPI293® expression system, using a DNA expression construct coding for the extracellular domain (ECD) of human TL1A with an N-terminally located HIS and FLAG tag. Other species forms of TL1A were generated based on sequence listing on publically listed databases. These are summarized below:

TABLE 2

| Species TL1A | Public Database Reference | SEQ ID NO: |
|---|---|---|
| Human | UniProt: O95150 | 31 |
| Cynomolgus Monkey | SEQ ID NO: 125 from US Publ. No. 2014/0255302 | 34 |
| Mouse | UniProt: Q5UBV8 | 35 |
| Rat | UniProt: Q8K3Y7 | 36 |
| Guinea Pig | UniProt: H0VFN8 | 37 |
| Cat | NCBI: XP_003995828.1 | 38 |
| Pig | UniProt: I3LL00 | 39 |
| Rabbit | UniProt: G1T1T1 | 40 |
| Dog | UniProt: J9P221 | 41 |

Culture supernatant containing the secreted TL1A protein was harvested by centrifugation at 2000×g for 10 mins to remove the cells. The TL1A protein was purified from the supernatant using a HISTRAP® HP column (GE Healthcare). The eluted protein was buffer-exchanged into PBS using a HILOAD® 16/60 Superdex 200 prep grade column (GE Healthcare) and ~70 kDa fraction was separated by gel filtration on a HILOAD® 26/60 SUPERDEX® 200 prep grade column (GE Healthcare).

1.7. TF-1 Cell Line Potency Assay. To determine which anti-TL1A antibodies functionally neutralize the biological activity of TL1A, antibodies were tested for their ability to neutralize TL1A-induced apoptosis in a TF-1 cell line. The TF-1 human erythroleukemic cell line (ATCC: CRL-2003) was maintained in culture under standard conditions. TF-1 cells ($7.5×10^4$/well) were incubated in black-sided 96-well plates (Greiner) with human TL1A 100 ng/ml and cycloheximide 10 µg/ml to induce apoptosis. Test antibodies at a concentration of 10 µg/mL (66.7 nM) or less were added to the plates and incubated for 4 to 5 hours. Induction of apoptosis was then assessed using the Homogeneous Caspases Kit (Roche) according to manufacturer's instructions.

Data were normalized by expression as a percentage of maximum apoptosis (apoptosis levels achieved by human TL1A plus cycloheximide in the absence of anti-TL1A antibody).

1.8. Receptor Selectivity of Lead Antibodies. TL1A binds both to its cognate signaling receptor, DR3, and to a decoy receptor, DcR3, which also serves as a decoy receptor for TNF family members Fas-L and LIGHT. Antibodies were assessed for their ability to inhibit binding of TL1A to its receptors in a competition ELISA. DR3/Fc Chimera (R&D Systems) or DcR3/Fc Chimera (R&D Systems) was coated onto a 96-well plate (Maxisorp, Nunc) at a concentration of 2 µg/ml. Serially diluted test antibodies were pre-incubated with single-site biotinylated human TL1A 1 µg/ml for 30 minutes then added to the DR3/Fc or DcR3/Fc coated wells. Bound TL1A was detected using streptavidin-horseradish peroxidase 1:2000 (BD Pharmingen). Data were normalized by expression as a percentage of maximum binding of TL1A to receptor in the absence of anti-TL1A antibody.

1.9. Kinetic Exclusion Assay. This assay measures the free concentration of one of the binding partners without perturbing the equilibrium. Solutions can be prepared off-line, using unmodified proteins in solution, and affinity measurements can be read days after mixing to ensure that equilibrium has been reached. In a kinetic exclusion assay, one interactant (termed the constant binding partner, or CBP) is held at a constant concentration, while the other (termed the titrant) is serially diluted. Kinetic exclusion assays may be used to determine the dissociation constant ($K_D$) and affinity of an antibody-antigen interaction. In a typical kinetic exclusion assay, the titrant is immobilized to beads (e.g., Sepharose or PMMA beads) and is used to capture the CBP free in solution. A secondary labeled probe is then used to quantify the amount of captured CBP. The kinetic exclusion assay is reviewed in Darling, RK et al. (2004) ASSAY and Drug Development Technol. 2(6):647-57.

The components were combined and allowed to reach equilibrium. The kinetic exclusion assay was then used to measure the free fraction of the CBP. Equilibrium curves with multiple CBP concentrations were analyzed using the n-curve analysis tool within the KinExA® Pro software (Version 4.1.11, Sapidyne) to obtain robust $K_D$ determinations. The interaction of 320-587 for human TL1A was examined using two orientations: (1) CBP is 320-587, titrant is TL1A, and (2) CBP is TL1A, titrant is 320-587.

EXAMPLE 2

Experimental Results 2.1. Selecting TL1A-binding variants with an equivalent or improved off-rate relative to C320-179. Variants of antibody 320-179 were constructed and expressed as described above. EXPI293® (Life Technologies Corp.) supernatants of each variant were assessed by BIACORE® (GE Healthcare) and the data obtained compared with that of the parental antibody 320-179. In some experiment the antibodies were purified using Protein A chromatography (See 1.4) and purified antibodies were used in BIACORE® (GE Healthcare) experiments. Tables 3-11 show the expression level of each variant, along with its binding to TL1A at an early and late time point. In later runs (Table 10 and 11) antibody variants containing more than one amino acid substitution were tested.

TABLE 3

SPR experiment - Run 1 - Anti-TL1A antibodies binding to TL1A.

| Antibody | VH Substitution relative to 320-179 | VL Substitution relative to 320-179 | Capture Level | TL1A Binding Level (Early) | TL1A Binding Level (Late) |
|---|---|---|---|---|---|
| | | | Purified Antibody | | |
| 320-179 | None | None | 410 | 140 | 117 |
| 320-184* | None | L79A | 414 | 141 | 118 |
| 320-185* | None | L79S | 401 | 137 | 114 |
| 320-186* | None | L79Q | 398 | 136 | 113 |
| 320-187* | None | L79D | 388 | 134 | 112 |
| 320-188* | None | L79H | 397 | 136 | 113 |
| 320-189* | None | L79K | 393 | 130 | 107 |
| 320-190* | None | L79W | 395 | 136 | 113 |
| 320-191* | None | L79Y | 408 | 140 | 117 |

*indicates antibodies that were selected for potency assay testing.

TABLE 4

| | | | | TL1A | TL1A | | TL1A | TL1A |
| | VH | VL | | Binding | Binding | | Binding | Binding |
| | Substitution | Substitution | | Level | Level | | Level | Level |
| | relative | relative | Capture | (Early) | (Late) | Capture | (Early) | (Late) |
| Antibody | to 320-179 | to 320-179 | Level | Supernatant | | Level | Purified Antibody | |
|---|---|---|---|---|---|---|---|---|
| 320-179 | None | None | 1133 | 287 | 261 | 410 | 140 | 117 |
| 320-192 | None | T24A | 960 | 238 | 218 | — | — | — |
| 320-193 | None | T24S | 990 | 249 | 227 | 409 | 103 | 91 |
| 320-194 | None | T24Q | 974 | 247 | 226 | 398 | 76 | 64 |
| 320-195 | None | T24D | 992 | 249 | 227 | — | — | — |
| 320-196 | None | T24H | 995 | 250 | 228 | — | — | — |
| 320-197 | None | T24K | 1017 | 255 | 232 | 401 | 105 | 94 |
| 320-198* | None | T24L | 1023 | 262 | 241 | — | — | — |
| 320-199 | None | T24W | 1050 | 251 | 233 | 404 | 97 | 85 |
| 320-200 | None | T24Y | 1027 | 251 | 231 | | | |
| 320-201* | None | S25A | 990 | 274 | 252 | 393 | 73 | 57 |
| 320-202* | None | S25Q | 1034 | 234 | 214 | — | — | — |
| 320-203 | None | S25D | 977 | 61 | 24 | 407 | 65 | 35 |
| 320-204 | None | S25H | 1003 | 193 | 155 | — | — | — |
| 320-205* | None | S25K | 1025 | 290 | 271 | 401 | 70 | 51 |
| 320-206 | None | S25L | 1000 | 257 | 235 | — | — | — |
| 320-207* | None | S25W | 1022 | 268 | 243 | — | — | — |
| 320-208 | None | S25Y | 1034 | 222 | 199 | — | — | — |
| 320-209* | None | S26A | 1007 | 222 | 200 | — | — | — |
| 320-210 | None | S26Q | 1033 | 225 | 202 | — | — | — |
| 320-211* | None | S26D | 1025 | 206 | 164 | 392 | 80 | 64 |
| 320-212 | None | S26H | 1013 | 226 | 205 | — | — | — |
| 320-213* | None | S26K | 1052 | 218 | 194 | 422 | 79 | 65 |
| 320-214 | None | S26L | 1038 | 221 | 196 | — | — | — |
| 320-215 | None | S26W | 1021 | 220 | 199 | — | — | — |
| 320-216 | None | S26Y | 1010 | 171 | 147 | — | — | — |
| 320-217 | None | S27A | 1076 | 258 | 235 | — | — | — |
| 320-218 | None | S27Q | 1081 | 239 | 218 | 412 | 92 | 80 |
| 320-219* | None | S27D | 1061 | 243 | 220 | — | — | — |
| 320-220 | None | S27H | 1049 | 253 | 230 | — | — | — |
| 320-221 | None | S27K | 1063 | 225 | 207 | 413 | 99 | 89 |
| 320-222 | None | S27L | 1037 | 156 | 96 | — | — | — |
| 320-223 | None | S27W | 1061 | 143 | 66 | — | — | — |
| 320-224 | None | S27Y | 1055 | 198 | 153 | — | — | — |
| 320-225 | None | S27aA | 1066 | 267 | 243 | — | — | — |
| 320-226* | None | S27aQ | 1035 | 250 | 228 | — | — | — |
| 320-227 | None | S27aD | 1022 | 242 | 218 | — | — | — |
| 320-228 | None | S27aH | 1072 | 259 | 235 | — | — | — |
| 320-229* | None | S27aK | 1057 | 268 | 251 | — | — | — |
| 320-230 | None | S27aL | 1087 | 245 | 223 | — | — | — |
| 320-231 | None | S27aW | 1078 | 271 | 243 | — | — | — |
| 320-232 | None | S27aY | 1051 | 261 | 235 | — | — | — |
| 320-233 | None | D27bA | 1118 | 255 | 235 | 409 | 48 | 16 |
| 320-234 | None | D27bS | 1089 | 262 | 239 | — | — | — |
| 320-235 | None | D27bQ | 1110 | 256 | 236 | — | — | — |
| 320-236 | None | D27bH | 1085 | 254 | 232 | 415 | 5 | 6 |
| 320-237 | None | D27bK | 1073 | 240 | 221 | 398 | 10 | 8 |
| 320-238 | None | D27bL | 1106 | 221 | 191 | — | — | — |
| 320-239 | None | D27bW | 1079 | 212 | 163 | — | — | — |
| 320-240 | None | D27bY | 1089 | 230 | 196 | — | — | — |
| 320-241* | None | I27cA | 1092 | 179 | 122 | — | — | — |
| 320-242 | None | I27cS | 1076 | 124 | 49 | — | — | — |
| 320-243 | None | I27cQ | 1065 | 71 | 26 | — | — | — |
| 320-244* | None | I27cD | 1083 | 21 | 20 | — | — | — |
| 320-245* | None | I27cH | 1084 | 59 | 26 | — | — | — |
| 320-246 | None | I27cK | 1089 | 32 | 23 | — | — | — |
| 320-247 | None | I27cL | 1078 | 205 | 162 | — | — | — |
| 320-248 | None | I27cW | 1110 | 96 | 30 | — | — | — |
| 320-249 | None | I27cY | 1096 | 77 | 28 | — | — | — |
| 320-250 | None | G28A | 1104 | 180 | 115 | — | — | — |
| 320-251 | None | G28S | 1085 | 134 | 50 | — | — | — |

*indicates antibodies that were selected for potency assay testing.

TABLE 5

SPR experiment - Run 3 - Anti-TL1A antibodies binding to TL1A.

| Antibody | VH Substitution relative to 320-179 | VL Substitution relative to 320-179 | Capture Level | TL1A Binding Level (Early) Supernatant | TL1A Binding Level (Late) |
|---|---|---|---|---|---|
| 320-252 | None | G28Q | 996 | 20 | 9 |
| 320-253 | None | G28D | 1073 | 6 | 6 |
| 320-254 | None | G28H | 1021 | 17 | 8 |
| 320-255 | None | G28K | 842 | 24 | 8 |
| 320-256 | None | G28L | 1055 | 30 | 10 |
| 320-257 | None | G28W | 981 | 83 | 18 |
| 320-258 | None | G28Y | 823 | 9 | 6 |
| 320-259 | None | A29S | 824 | 194 | 179 |
| 320-260 | None | A29Q | 836 | 182 | 165 |
| 320-261 | None | A29D | 956 | 86 | 29 |
| 320-262 | None | A29H | 891 | 209 | 190 |
| 320-263* | None | A29K | 848 | 121 | 123 |
| 320-264 | None | A29L | 831 | 199 | 184 |
| 320-265 | None | A29W | 1057 | 168 | 69 |
| 320-266 | None | A29Y | 934 | 218 | 192 |
| 320-267* | None | G30A | 1148 | 299 | 297 |
| 320-268 | None | G30S | 392 | 28 | 7 |
| 320-269 | None | G30Q | 764 | 126 | 93 |
| 320-270 | None | G30D | 511 | 9 | 5 |
| 320-271 | None | G30H | 1067 | 106 | 30 |
| 320-272 | None | G30K | 935 | 5 | 5 |
| 320-273 | None | G30L | 710 | 4 | 4 |
| 320-274 | None | G30W | 796 | 12 | 7 |
| 320-275 | None | G30Y | 751 | 44 | 10 |
| 320-276 | None | L31A | 1273 | 244 | 215 |
| 320-277* | None | L31S | 1741 | 387 | 361 |
| 320-278* | None | L31Q | 1696 | 389 | 374 |
| 320-279 | None | L31D | 561 | 144 | 128 |
| 320-280* | None | L31H | 881 | 228 | 211 |
| 320-281 | None | L31K | 321 | 22 | 6 |
| 320-282 | None | L31W | 811 | 75 | 16 |
| 320-283 | None | L31Y | 317 | 2 | 3 |
| 320-284 | None | G32A | 374 | 1 | 2 |
| 320-285 | None | G32S | 400 | 1 | 2 |
| 320-286 | None | G32Q | 576 | 1 | 4 |
| 320-287 | None | G32D | 339 | 0 | 2 |
| 320-288 | None | G32H | 422 | 1 | 3 |
| 320-289 | None | G32K | 463 | 1 | 3 |
| 320-290 | None | G32L | 361 | 1 | 2 |
| 320-291 | None | G32W | 414 | 2 | 3 |
| 320-292 | None | G32Y | 423 | 111 | 94 |
| 320-293 | None | V33A | 421 | 104 | 86 |
| 320-294 | None | V33S | 419 | 79 | 61 |
| 320-295 | None | V33Q | 414 | 109 | 94 |
| 320-296 | None | V33D | 428 | 118 | 104 |
| 320-297* | None | V33H | 420 | 95 | 77 |
| 320-298 | None | V33K | 416 | 114 | 100 |
| 320-299 | None | V33L | 420 | 51 | 13 |
| 320-300 | None | H34W | 417 | 111 | 95 |
| 320-301 | None | H34Y | 456 | 108 | 96 |
| 320-302* | None | H34A | 423 | 99 | 74 |
| 320-303 | None | H34S | 408 | 71 | 32 |
| 320-304 | None | H34Q | 401 | 103 | 82 |
| 320-305 | None | H34D | 424 | 34 | 10 |
| 320-306 | None | H34K | 452 | 147 | 133 |
| 320-307* | None | H34L | 873 | 216 | 200 |
| 320-308 | None | H34W | 458 | 106 | 73 |
| 320-309 | None | H34Y | 255 | 47 | 40 |
| 320-310 | None | Q89A | 348 | 70 | 62 |
| 320-311 | None | Q89S | 0 | 0 | 0 |

*indicates antibodies that were selected for potency assay testing.

TABLE 6

SPR experiment - Run 4 - Anti-TL1A antibodies binding to TL1A.

| Antibody | VH Substitution relative to 320-179 | VL Substitution relative to 320-179 | Capture Level | TL1A Binding Level (Early) Purified Antibody | TL1A Binding Level (Late) |
|---|---|---|---|---|---|
| 320-179 | None | None | 616 | 177 | 163 |
| 320-312 | None | Q89D | 529 | 10 | 10 |
| 320-313* | None | Q89H | 502 | 141 | 132 |
| 320-314* | None | Q89K | 598 | 165 | 158 |
| 320-315 | None | Q89L | 515 | 85 | 82 |
| 320-316 | None | Q89W | 535 | 65 | 62 |
| 320-317 | None | Q89Y | 570 | 86 | 83 |
| 320-318* | None | S90A | 578 | 160 | 149 |
| 320-319 | None | S90Q | 523 | 18 | 14 |
| 320-320 | None | S90D | 534 | 31 | 17 |
| 320-321 | None | S90H | 491 | 16 | 13 |
| 320-322 | None | S90K | 450 | 17 | 14 |
| 320-323 | None | S90W | 490 | 14 | 13 |
| 320-324 | None | S90Y | 528 | 13 | 12 |
| 320-325 | None | Y91A | 491 | 95 | 83 |
| 320-326* | None | Y91S | 550 | 126 | 120 |
| 320-327 | None | Y91Q | 493 | 130 | 119 |
| 320-328* | None | Y91H | 542 | 155 | 146 |
| 320-329 | None | Y91K | 600 | 9 | 11 |
| 320-330 | None | Y91L | 600 | 139 | 119 |
| 320-331* | None | Y91W | 615 | 173 | 176 |
| 320-332 | None | D92A | 531 | 66 | 44 |
| 320-333 | None | D92S | 559 | 95 | 67 |
| 320-334 | None | D92Q | 543 | 15 | 14 |
| 320-335 | None | D92H | 581 | 15 | 14 |
| 320-336 | None | D92K | 484 | 11 | 11 |
| 320-337 | None | D92L | 475 | 21 | 15 |
| 320-338 | None | D92W | 548 | 9 | 11 |
| 320-339 | None | D92Y | 509 | 10 | 11 |
| 320-340 | None | G93A | 548 | 145 | 132 |
| 320-341 | None | G93S | 560 | 149 | 135 |
| 320-342 | None | G93Q | 560 | 152 | 139 |
| 320-343 | None | G93D | 545 | 121 | 90 |
| 320-344 | None | G93H | 529 | 117 | 87 |
| 320-345* | None | G93K | 637 | 163 | 154 |
| 320-346 | None | G93L | 526 | 126 | 107 |
| 320-347 | None | G93W | 560 | 149 | 130 |
| 320-348 | None | G93Y | 541 | 144 | 127 |
| 320-349 | None | T94A | 556 | 112 | 88 |
| 320-350 | None | T94S | 502 | 130 | 118 |
| 320-351 | None | T94Q | 553 | 112 | 83 |
| 320-352 | None | T94D | 568 | 101 | 63 |
| 320-353 | None | T94H | 558 | 97 | 73 |
| 320-354 | None | T94K | 536 | 53 | 30 |
| 320-355 | None | T94L | 526 | 102 | 76 |
| 320-356 | None | T94W | 486 | 109 | 86 |
| 320-357 | None | T94Y | 563 | 119 | 91 |
| 320-358 | None | L95A | 501 | 82 | 50 |
| 320-359 | None | L95S | 503 | 57 | 27 |
| 320-360 | None | L95Q | 554 | 86 | 53 |
| 320-361* | None | L95D | 477 | 12 | 11 |
| 320-362 | None | L95H | 522 | 8 | 9 |
| 320-363 | None | L95Y | 566 | 17 | 16 |
| 320-364 | None | S95aA | 516 | 124 | 109 |
| 320-365 | None | S95aQ | 536 | 141 | 128 |
| 320-366 | None | S95aD | 487 | 62 | 31 |
| 320-367 | None | S95aH | 595 | 119 | 116 |
| 320-368 | None | S95aK | 602 | 50 | 26 |
| 320-369 | None | S95aL | 503 | 89 | 60 |
| 320-370 | None | S95aW | 570 | 66 | 39 |
| 320-371 | None | S95aY | 576 | 92 | 70 |

*indicates antibodies that were selected for potency assay testing.

TABLE 7

SPR experiment - Run 5 - Anti-TL1A antibodies binding to TL1A.

| Antibody | VH Substitution relative to 320-179 | VL Substitution relative to 320-179 | Capture Level | TL1A Binding Level (Early) Supernatant | TL1A Binding Level (Late) |
|---|---|---|---|---|---|
| 320-179 | None | None | 83 | 11 | 10 |
| 320-372 | None | A96S | 106 | 1 | 0 |
| 320-373 | None | A96Q | 99 | −1 | −1 |
| 320-374 | None | A96D | 98 | 1 | 0 |
| 320-375 | None | A96H | 108 | −2 | −1 |
| 320-376 | None | A96K | 98 | 3 | 1 |
| 320-377 | None | A96L | 101 | −1 | −1 |
| 320-378 | None | A96W | 105 | −1 | −1 |
| 320-379 | None | A96Y | 105 | 3 | 1 |
| 320-380 | None | L97A | 104 | 1 | 1 |
| 320-381 | None | L97S | 97 | 3 | 1 |
| 320-382 | None | L97Q | 106 | 0 | 0 |
| 320-383 | None | L97D | 102 | 3 | 1 |
| 320-384 | None | L97H | 98 | 3 | 2 |
| 320-385 | None | L97K | 108 | 1 | 1 |
| 320-386 | None | L97W | 104 | 1 | 0 |
| 320-387 | None | L97Y | 97 | 11 | 10 |
| 320-388 | G26A | None | 110 | 14 | 13 |
| 320-389 | G26S | None | 105 | 12 | 11 |
| 320-390 | G26Q | None | 100 | 12 | 11 |
| 320-391 | G26D | None | 106 | 14 | 13 |
| 320-392 | G26H | None | 109 | 12 | 11 |
| 320-393 | G26K | None | 100 | 12 | 11 |
| 320-394 | G26L | None | 106 | 13 | 12 |
| 320-395 | G26W | None | 104 | 13 | 12 |
| 320-396 | G26Y | None | 104 | 12 | 11 |
| 320-397 | Y27A | None | 109 | 12 | 12 |
| 320-398 | Y27S | None | 110 | 12 | 11 |
| 320-399 | Y27Q | None | 105 | 10 | 10 |
| 320-400 | Y27D | None | 106 | 11 | 11 |
| 320-401 | Y27H | None | 100 | 11 | 10 |
| 320-402 | Y27L | None | 98 | 11 | 10 |
| 320-403 | Y27W | None | 84 | 11 | 10 |
| 320-404 | T28A | None | 84 | 11 | 10 |
| 320-405 | T28S | None | 79 | 10 | 9 |
| 320-406 | T28Q | None | 82 | 8 | 7 |
| 320-407 | T28D | None | 88 | 12 | 11 |
| 320-408 | T28H | None | 81 | 13 | 12 |
| 320-409 | T28K | None | 83 | 10 | 10 |
| 320-410 | T28L | None | 86 | 11 | 10 |
| 320-411 | T28W | None | 82 | 10 | 9 |
| 320-412 | T28Y | None | 89 | 10 | 9 |
| 320-413 | F29A | None | 89 | 9 | 8 |
| 320-414 | F29S | None | 78 | 7 | 7 |
| 320-415 | F29Q | None | 85 | 5 | 4 |
| 320-416 | F29D | None | 81 | 9 | 8 |
| 320-417 | F29H | None | 85 | 9 | 8 |
| 320-418 | F29K | None | 85 | 10 | 9 |
| 320-419 | F29L | None | 83 | 11 | 9 |
| 320-420 | F29W | None | 85 | 11 | 10 |
| 320-421 | F28Y | None | 81 | 9 | 8 |
| 320-422 | T30A | None | 80 | 10 | 9 |
| 320-423 | T30S | None | 86 | 10 | 10 |
| 320-424 | T30Q | None | 86 | 11 | 10 |
| 320-425 | T30D | None | 89 | 14 | 12 |
| 320-426 | T30H | None | 84 | 10 | 9 |
| 320-427 | T30K | None | 88 | 11 | 10 |
| 320-428 | T30L | None | 88 | 11 | 10 |
| 320-429 | T30W | None | 90 | 12 | 11 |
| 320-430 | T30Y | None | 85 | 6 | 6 |
| 320-431 | S31A | None | 85 | 6 | 6 |

TABLE 8

SPR experiment - Run 6 - Anti-TL1A antibodies binding to TL1A.

| Antibody | VH Substitution relative to 320-179 | VL Substitution relative to 320-179 | Capture Level | TL1A Binding Level (Early) Purified Antibody | TL1A Binding Level (Late) |
|---|---|---|---|---|---|
| 320-179 | None | None | 449 | 111 | 102 |
| 320-432 | S31Q | None | 466 | 116 | 106 |
| 320-433 | S31D | None | 412 | 90 | 83 |
| 320-434 | S31K | None | 473 | 125 | 113 |
| 320-435 | S31L | None | 384 | 92 | 83 |
| 320-436 | S31W | None | 525 | 129 | 118 |
| 320-437 | S31Y | None | 501 | 119 | 109 |
| 320-438 | Y32A | None | 468 | 126 | 116 |
| 320-439 | Y32S | None | 464 | 119 | 108 |
| 320-440 | Y32Q | None | 408 | 108 | 97 |
| 320-441 | Y32D | None | 388 | 80 | 67 |
| 320-442 | Y32H | None | 490 | 124 | 113 |
| 320-443* | Y32K | None | 438 | 114 | 103 |
| 320-444 | Y32L | None | 458 | 107 | 95 |
| 320-445* | Y32W | None | 442 | 116 | 106 |
| 320-446 | D33A | None | 469 | 18 | 8 |
| 320-447 | D33S | None | 503 | 37 | 13 |
| 320-448 | D33Q | None | 482 | 7 | 6 |
| 320-449 | D33H | None | 483 | 76 | 59 |
| 320-450 | D33K | None | 536 | 1 | 3 |
| 320-451 | D33L | None | 497 | 19 | 8 |
| 320-452 | D33W | None | 445 | 84 | 78 |
| 320-453 | D33Y | None | 449 | 111 | 104 |
| 320-454 | I34A | None | 189 | 43 | 37 |
| 320-455 | I34S | None | 144 | 27 | 23 |
| 320-456 | I34Q | None | 214 | 52 | 46 |
| 320-457 | I34D | None | 55 | 6 | 4 |
| 320-458 | I34H | None | 239 | 59 | 53 |
| 320-459 | I34K | None | 93 | 20 | 17 |
| 320-460 | I34L | None | 441 | 114 | 105 |
| 320-461 | I34W | None | 465 | 87 | 82 |
| 320-462 | I34Y | None | 373 | 58 | 52 |
| 320-463* | N35A | None | 462 | 102 | 101 |
| 320-464* | N35S | None | 600 | 130 | 124 |
| 320-465 | N35Q | None | 476 | 92 | 78 |
| 320-466 | N35D | None | 360 | 93 | 86 |
| 320-467 | N35H | None | 350 | 44 | 24 |
| 320-468 | N35K | None | 200 | 2 | 2 |
| 320-469 | N35L | None | 315 | 69 | 61 |
| 320-470 | N35W | None | 329 | 2 | 3 |
| 320-471 | N35Y | None | 312 | 3 | 4 |
| 320-472 | None | S90L | 467 | 23 | 10 |
| 320-473 | None | Y91D | 453 | 69 | 55 |
| 320-474 | None | L95K | 596 | 2 | 4 |
| 320-475 | None | L95W | 727 | 8 | 8 |
| 320-476 | Y27K | None | 560 | 128 | 118 |
| 320-477* | S31H | None | 576 | 148 | 136 |
| 320-478 | A60L | None | 379 | 85 | 77 |
| 320-479 | A60W | None | 277 | 61 | 54 |
| 320-480 | A60Y | None | 319 | 79 | 73 |
| 320-483 | W50A | None | 492 | 4 | 6 |
| 320-484 | W50S | None | 555 | 3 | 6 |
| 320-485 | W50Q | None | 460 | 3 | 5 |
| 320-486 | W50D | None | 178 | 1 | 2 |
| 320-487 | W50H | None | 237 | 2 | 3 |
| 320-488 | W50K | None | 293 | 1 | 2 |
| 320-489 | W50L | None | 337 | 4 | 5 |
| 320-490 | W50Y | None | 393 | 14 | 8 |
| 320-491 | L51S | None | 356 | 85 | 76 |

*indicates antibodies that were selected for potency assay testing.

TABLE 9

SPR experiment - Run 7 - Anti-TL1 antibodies binding to TL1A.

| Antibody | VH Substitution relative to 320-179 | VL Substitution relative to 320-179 | Capture Level | TL1A Binding Level (Early) Purified Antibody | TL1A Binding Level (Late) Purified Antibody |
|---|---|---|---|---|---|
| 320-179 | None | None | 301 | 61 | 56 |
| 320-492 | L51Q | None | 439 | 89 | 82 |
| 320-493 | L51D | None | 242 | 48 | 46 |
| 320-494 | L51H | None | 811 | 150 | 138 |
| 320-495 | L51K | None | 466 | 84 | 77 |
| 320-496 | L51W | None | 581 | 93 | 87 |
| 320-497 | N52A | None | 727 | 135 | 125 |
| 320-498 | N52S | None | 485 | 90 | 82 |
| 320-499 | N52Q | None | 551 | 122 | 113 |
| 320-500 | N52D | None | 472 | 69 | 53 |
| 320-501 | N52H | None | 533 | 118 | 108 |
| 320-502 | N52K | None | 659 | 88 | 59 |
| 320-503 | N52W | None | 484 | 41 | 6 |
| 320-504 | N52Y | None | 500 | 88 | 65 |
| 320-505 | P52aA | None | 570 | 118 | 110 |
| 320-506 | P52aS | None | 444 | 97 | 89 |
| 320-507 | P52aQ | None | 181 | 27 | 24 |
| 320-508 | P52aD | None | 203 | 19 | 12 |
| 320-509 | P52aH | None | 290 | 52 | 47 |
| 320-510 | P52aK | None | 289 | 44 | 33 |
| 320-511 | P52aL | None | 581 | 106 | 98 |
| 320-512 | P52aW | None | 746 | 126 | 118 |
| 320-513 | P52aY | None | 585 | 99 | 90 |
| 320-514 | N53A | None | 516 | 96 | 88 |
| 320-515 | N53S | None | 375 | 73 | 67 |
| 320-516 | N53Q | None | 461 | 92 | 86 |
| 320-517 | N53D | None | 493 | 55 | 50 |
| 320-518 | N53H | None | 882 | 169 | 153 |
| 320-519 | N53K | None | 993 | 217 | 196 |
| 320-520 | N53L | None | 1016 | 174 | 162 |
| 320-521 | N53W | None | 830 | 166 | 152 |
| 320-522 | N53Y | None | 693 | 141 | 129 |
| 320-523 | S54A | None | 476 | 88 | 82 |
| 320-524 | S54Q | None | 292 | 55 | 49 |
| 320-525 | S54D | None | 437 | 33 | 17 |
| 320-526 | S54H | None | 672 | 134 | 124 |
| 320-527 | S54K | None | 578 | 146 | 136 |
| 320-528 | S54L | None | 829 | 121 | 108 |
| 320-529 | S54W | None | 605 | 94 | 83 |
| 320-530 | S54Y | None | 425 | 77 | 67 |
| 320-531 | G55A | None | 331 | 66 | 61 |
| 320-532 | G55S | None | 648 | 10 | 7 |
| 320-533 | G55Q | None | 441 | 93 | 86 |
| 320-534 | G55D | None | 647 | 109 | 102 |
| 320-535 | G55H | None | 637 | 126 | 115 |
| 320-536 | G55K | None | 553 | 115 | 105 |
| 320-537 | G55L | None | 717 | 133 | 123 |
| 320-538 | G55W | None | 318 | 54 | 49 |
| 320-539 | N56A | None | 859 | 172 | 159 |
| 320-540 | N56S | None | 500 | 100 | 92 |
| 320-541 | N56Q | None | 504 | 94 | 84 |
| 320-542 | N56D | None | 839 | 97 | 86 |
| 320-543 | N56H | None | 597 | 138 | 126 |
| 320-544 | N56K | None | 690 | 120 | 112 |
| 320-545 | N56L | None | 518 | 109 | 100 |
| 320-546 | N56W | None | 341 | 67 | 61 |
| 320-547* | N56Y | None | 318 | 77 | 75 |
| 320-548 | T57A | None | 335 | 74 | 68 |
| 320-549 | T57S | None | 269 | 50 | 45 |
| 320-550 | T57Q | None | 635 | 112 | 103 |
| 320-551 | T57D | None | 280 | 44 | 36 |
| 320-552 | T57H | None | 595 | 104 | 97 |
| 320-553 | T57K | None | 494 | 84 | 78 |
| 320-554 | T57L | None | 506 | 66 | 51 |
| 320-555 | T57W | None | 674 | 62 | 30 |
| 320-556 | T57Y | None | 634 | 100 | 90 |
| 320-557 | G58A | None | 378 | 26 | 6 |
| 320-558 | G58S | None | 463 | 3 | 2 |
| 320-559 | G58Q | None | 535 | 9 | 5 |
| 320-560 | G58D | None | 907 | 36 | 9 |
| 320-561 | G58H | None | 539 | 14 | 6 |
| 320-562 | G58K | None | 326 | 2 | 1 |
| 320-563 | G58L | None | 258 | 2 | 2 |
| 320-564 | G58W | None | 345 | 72 | 67 |
| 320-565 | G58Y | None | 545 | 43 | 12 |
| 320-566 | Y59A | None | 720 | 120 | 110 |
| 320-567 | Y59S | None | 590 | 96 | 86 |
| 320-568 | Y59Q | None | 688 | 115 | 107 |
| 320-569 | Y59D | None | 408 | 79 | 73 |
| 320-570 | Y59H | None | 435 | 79 | 72 |
| 320-571 | Y59K | None | 394 | 78 | 72 |
| 320-572 | A60S | None | 459 | 98 | 90 |
| 320-573 | A60Q | None | 338 | 67 | 62 |
| 320-574 | A60D | None | 693 | 140 | 130 |
| 320-575 | A60H | None | 581 | 121 | 110 |
| 320-576 | A60K | None | 479 | 90 | 83 |
| 320-577 | L51A | None | 479 | 98 | 90 |
| 320-578 | L51Y | None | 415 | 83 | 77 |
| 320-579 | N52L | None | 214 | 46 | 41 |
| 320-580 | G55Y | None | 261 | 51 | 47 |
| 320-581 | Y59L | None | 337 | 70 | 65 |
| 320-582 | Y59W | None | 453 | 67 | 52 |

*indicates antibodies that were selected for potency assay testing.

TABLE 10

SPR experiment - Run 8 - Anti-TL1A antibodies binding to TL1A.

| Antibody | VH Substitution relative to 320-179 | VL Substitution relative to 320-179 | Capture Level | TL1A Binding Level (Early) Purified Antibody | TL1A Binding Level (Late) Purified Antibody |
|---|---|---|---|---|---|
| 320-179 | None | None | 402 | 98 | 86 |
| 320-583* | None | G30A, Y91W | 404 | 108 | 103 |
| 320-584* | None | L31S, Y91W | 399 | 103 | 98 |
| 320-585* | None | L31Q, Y91W | 406 | 116 | 109 |
| 320-586* | None | H34L, Y91W | 405 | 108 | 103 |
| 320-587* | N56Y | Y91W | 402 | 123 | 122 |
| 320-588* | N56Y | G30A | 409 | 128 | 123 |
| 320-589* | N56Y | L31S | 399 | 120 | 109 |
| 320-590* | N56Y | L31Q | 405 | 130 | 121 |
| 320-591* | N56Y | H34L | 399 | 132 | 124 |
| 320-592* | N56Y | G30A, Y91W | 408 | 128 | 129 |
| 320-593* | N56Y | L31S, Y91W | 405 | 126 | 124 |
| 320-594* | N56Y | L31Q, Y91W | 407 | 134 | 132 |
| 320-595* | N56Y | H34L, Y91W | 403 | 129 | 128 |

*indicates antibodies that were selected for potency assay testing.

TABLE 11

SPR experiment - Run 9 - Anti-TL1A antibodies binding to TL1A.

| Antibody | VH Substitution relative to 320-179 | VL Substitution relative to 320-179 | Capture Level | TL1A Binding Level (Early) Purified Antibody | TL1A Binding Level (Late) Purified Antibody |
|---|---|---|---|---|---|
| 320-179 | None | None | 402 | 108 | 98 |
| 320-596 | None | Y91F | 405 | 95 | 85 |
| 320-597 | None | L31Q, Y91F | 401 | 115 | 105 |
| 320-598 | None | H34L, Y91F | 403 | 112 | 101 |
| 320-599 | None | L31S, Y91F | 411 | 113 | 103 |
| 320-600 | None | G30A, Y91F | 399 | 111 | 104 |
| 320-601* | N56Y | Y91F | 409 | 121 | 120 |
| 320-602 | N56Y | L31Q, Y91F | 399 | 131 | 125 |
| 320-603 | N56Y | H34L, Y91F | 394 | 126 | 118 |

TABLE 11-continued

SPR experiment - Run 9 - Anti-TL1A antibodies binding to TL1A.

| Antibody | VH Substitution relative to 320-179 | VL Substitution relative to 320-179 | Capture Level | TL1A Binding Level (Early) Purified Antibody | TL1A Binding Level (Late) |
|---|---|---|---|---|---|
| 320-605 | N56Y | G30A, Y91F | 399 | 125 | 120 |
| 320-611* | N56Y | Y91W, G93K | 397 | 125 | 127 |
| 320-612 | None | Y91W, G93Y | 400 | 126 | 120 |
| 320-613* | N56Y | Y91W, G93Y | 408 | 135 | 131 |
| 320-614 | N56Y | G93K | 401 | 122 | 111 |
| 320-615 | N56Y | G93Y | 393 | 113 | 108 |
| 320-616 | N56Y | G93A | 396 | 120 | 112 |

*indicates antibodies that were selected for potency assay testing.

Antibodies that had capture levels similar or better than 320-179 as well as a TL1A Binding Level (Early) and TL1A Binding Level (Late) values that were in a similar range were taken forward into potency assays. These variants are indicated by * in Tables 3-11. A comparison of the off-rate as measured by SPR for several of the antibodies is shown in FIG. 5. Several of the antibodies dissociated at a slower rate than that of the parental antibody 320-179.

2.2 Anti-TL1A antibodies with improved potency in cell based assay. To assess if improved off-rate correlated with an enhanced potency purified antibody, variants were run in the TL1A induced caspase activity assay in TF-1 cells. Potent antibodies act by binding to TL1A and inhibiting TL1A activation of the DR3 receptor. This receptor triggers an apoptosis pathway in which caspases are activated and can be detected using commercial reagents. In each experiment the antibody variant was compared to 320-179 for fold improvement in potency. The results are shown in Table 12.

TABLE 12

TL1A induced caspase potency assay in TF-1 cells: Inhibition by anti-TL1A antibodies.

| Antibody | VH Substitution relative to 320-179 | VL Substitution relative to 320-179 | Antibody IC$_{50}$ (µg/mL) | 320-179 IC$_{50}$ (µg/mL) | Fold improvement |
|---|---|---|---|---|---|
| 320-184 | None | L79A | 0.010 | 0.030 | 3 |
| 320-185 | None | L79S | 0.020 | 0.030 | 2 |
| 320-186 | None | L79Q | 0.030 | 0.030 | 1 |
| 320-187 | None | L79D | 0.020 | 0.040 | 2 |
| 320-188 | None | L79H | 0.010 | 0.040 | 4 |
| 320-189 | None | L79K | 0.110 | 0.040 | 0 |
| 320-190 | None | L79W | 0.020 | 0.040 | 2 |
| 320-191 | None | L79Y | 0.020 | 0.040 | 2 |
| 320-198 | None | T24L | 0.010 | 0.010 | 1 |
| 320-201 | None | S25A | 0.005 | 0.010 | 2 |
| 320-202 | None | S25Q | 0.010 | 0.010 | 1 |
| 320-205 | None | S25K | 0.020 | 0.030 | 2 |
| 320-207 | None | S25W | 0.007 | 0.020 | 3 |
| 320-209 | None | S26A | 0.040 | 0.020 | 1 |
| 320-211 | None | S26D | 0.010 | 0.030 | 3 |
| 320-213 | None | S26K | 0.070 | 0.030 | 0 |
| 320-219 | None | S27D | 0.020 | 0.030 | 2 |
| 320-226 | None | S27aQ | 0.030 | 0.020 | 1 |
| 320-229 | None | S27aK | 0.040 | 0.060 | 2 |
| 320-241 | None | I27cA | 0.020 | 0.010 | 1 |
| 320-244 | None | I27cD | 5.030 | 0.010 | 0 |
| 320-245 | None | I27cH | 0.540 | 0.010 | 0 |
| 320-263 | None | A29K | 0.003 | 0.010 | 3 |
| 320-267 | None | G30A | 0.010 | 0.040 | 4 |
| 320-277 | None | L31S | 0.003 | 0.010 | 3 |
| 320-278 | None | L31Q | 0.010 | 0.020 | 2 |
| 320-280 | None | L31H | 0.006 | 0.020 | 3 |
| 320-297 | None | V33H | 0.005 | 0.020 | 4 |

TABLE 12-continued

TL1A induced caspase potency assay in TF-1 cells: Inhibition by anti-TL1A antibodies.

| Antibody | VH Substitution relative to 320-179 | VL Substitution relative to 320-179 | Antibody IC$_{50}$ (µg/mL) | 320-179 IC$_{50}$ (µg/mL) | Fold improvement |
|---|---|---|---|---|---|
| 320-302 | None | H34A | 0.010 | 0.020 | 2 |
| 320-307 | None | H34L | 0.010 | 0.040 | 4 |
| 320-313 | None | Q89H | 0.020 | 0.030 | 2 |
| 320-314 | None | Q89K | 0.020 | 0.030 | 2 |
| 320-318 | None | S90A | 0.020 | 0.050 | 3 |
| 320-326 | None | Y91S | 0.030 | 0.050 | 2 |
| 320-328 | None | Y91H | 0.020 | 0.020 | 1 |
| 320-331 | None | Y91W | 0.002 | 0.020 | 10 |
| 320-345 | None | G93K | 0.020 | 0.010 | 1 |
| 320-361 | None | L95D | 0.010 | 0.010 | 1 |
| 320-443 | Y32K | None | 0.060 | 0.060 | 1 |
| 320-445 | Y32W | None | 0.030 | 0.060 | 2 |
| 320-463 | N35A | None | 0.020 | 0.050 | 3 |
| 320-464 | N35S | None | 0.030 | 0.050 | 2 |
| 320-477 | S31H | None | 0.030 | 0.040 | 1 |
| 320-547 | N56Y | None | 0.004 | 0.040 | 10 |
| 320-583 | None | G30A, Y91W | 0.003 | 0.080 | 27 |
| 320-584 | None | L31S, Y91W | 0.008 | 0.080 | 10 |
| 320-585 | None | L31Q, Y91W | 0.003 | 0.040 | 13 |
| 320-586 | None | H34L, Y91W | 0.002 | 0.050 | 25 |
| 320-587 | N56Y | Y91W | 0.001 | 0.040 | 40 |
| 320-588 | N56Y | G30A | 0.004 | 0.020 | 5 |
| 320-589 | N56Y | L31S | 0.020 | 0.020 | 1 |
| 320-590 | N56Y | L31Q | 0.006 | 0.020 | 3 |
| 320-591 | N56Y | H34L | 0.002 | 0.020 | 10 |
| 320-592 | N56Y | G30A, Y91W | 0.003 | 0.020 | 7 |
| 320-593 | N56Y | L31S, Y91W | 0.004 | 0.060 | 15 |
| 320-594 | N56Y | L31Q, Y91W | 0.005 | 0.060 | 12 |
| 320-595 | N56Y | H34L, Y91W | 0.003 | 0.060 | 20 |
| 320-601 | N56Y | Y91F | 0.002 | 0.020 | 10 |
| 320-611 | N56Y | Y91W, G93K | 0.005 | 0.040 | 8 |
| 320-613 | N56Y | Y91W, G93Y | 0.010 | 0.040 | 4 |

Figure 7:
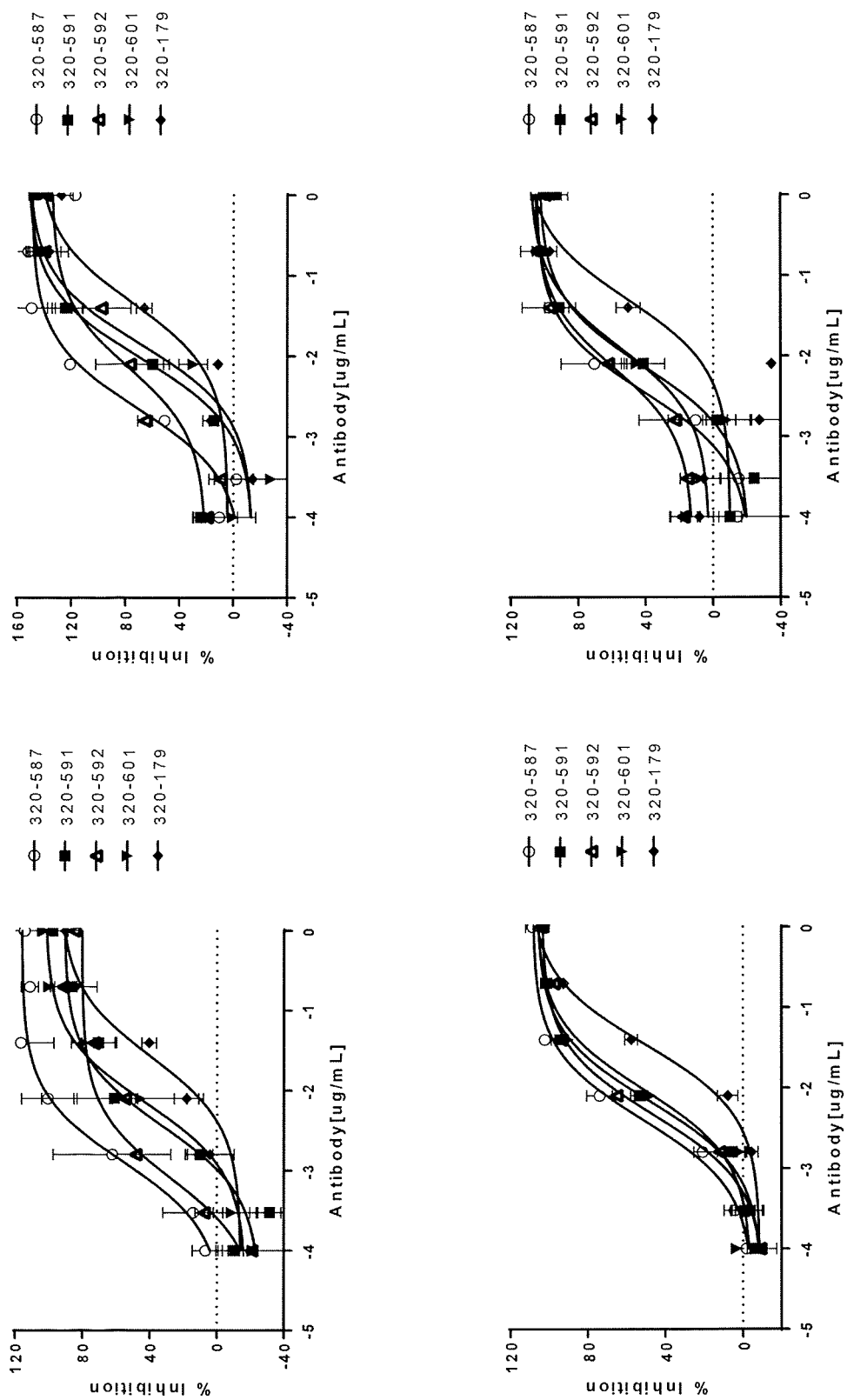
FIG. 7 shows the results of TF-1 cell caspase potency assays using various TL1A antibodies compared to the parent antibody, 320-179.

** Several of the antibodies with fold improvements greater than 10 fold improvement in potency were run in up to n = 7 assays. Results were consistent with the data shown in this table. FIG. 7 shows n = 4 replicates of several of the antibodies with improved potency compared to 320-179.

As demonstrated in Table 12 and in FIG. 6, several of the single substitution antibodies tested had superior potency compared to 320-179. Of all the single substitution antibody variants tested two had greater than 10 fold improvement in potency when compared to 320-179. These variants were 320-331 (which contained a Y91W substitution in the variable light chain) and 320-547 (which contained a N56Y substitution in the variable heavy chain) (FIG. 6). This result is unexpected, as typically CDR3 of the antibody VH is dominantly involved in antibody binding, while in contrast, the N56Y substitution that was identified has substantial influence on binding lies in CDR2 of the antibody VH. When variants were made incorporating either Y91W from the VL or separately N56Y in the VH with other substitutions that improved the potency, highly potent antibodies were obtained. When the Y91W VL substitution was combined with the N56Y VH substitution into one antibody, 320-587, the fold improvement in potency compared to 320-179 was 40. FIG. 7 shows four different repeat experiments demonstrating the potency increase of four antibodies 320-587, 320-591, 320-592, and 320-601 compared to 320-

179. The sequences of these antibodies with improved potency compared to 320-179 are shown in FIG. 3 (variable heavy chain) and FIG. 4 (variable light chain).

A comparison of the potency of 320-587 compared to other previously described anti-TL1A antibodies was performed. These previously described antibodies include antibody 1681N described in U.S. Pat. No. 8,642,741 (VH is SEQ ID NO: 18; VL is SEQ ID NO. 26), antibody VH5/VL1 from U.S. Publ. No. 2014/0308271 (VH is SEQ ID NO: 24; VL is SEQ ID NO: 17), humanized 1B4 as described in U.S. Pat. No. 8,263,743 (VH is SEQ ID NO: 74; VL is SEQ ID NO: 75) and 320-168 (also called C320-168) as described in U.S. Publ. No. 2014/0255302A1 (VH is SEQ ID NO: 181; VL is SEQ ID NO: 194). FIG. 8 shows that 320-587 has superior potency in the cell based assay compared to these previously described antibodies, making it the most potent anti-TL1A antibody described.

2.3. DR3 and DcR3 receptor competition assays. Antibodies that displayed increased potency compared to 320-179 were screened for their ability to inhibit TL1A binding to its cognate signalling receptor, DR3, or a decoy receptor, DcR3. All anti-TL1A antibodies tested showed inhibition of TL1A binding to DR3, when compared to an isotype control (FIG. 9). This confirms that the antibodies inhibit TL1A activity by blocking the TL1A-DR3 interaction.

In previous experiments described in U.S. Publ. No. 2014/0255302A1 (Example 4), antibody 320-179 (320-179) was tested in receptor competition assay and shown to selectively inhibit the binding of TL1A to DR3 but not to DcR3 (FIG. 10). In experiments presented herein in FIG. 10 it is again shown that 320-179 does not inhibit the TL1A-DcR3 interaction. This stands in contrast with the improved anti-TL1A antibodies tested. Antibodies with improved potency in the TF-1 cell assay (as described in Section 2.2), including antibody 320-587, consistently inhibited the TL1A-DcR3 interaction.

In summary, the parental antibody 320-179 was capable of inhibiting the TL1A-DR3 interaction but not the TL1A-DcR3 interaction. Several antibodies with improved potency such as 320-267 (VH is SEQ ID No: 1; VL is SEQ ID No: 11), 320-277 (VL is SEQ ID NO: 1, VL is SEQ ID NO 12), 320-278 (VH is SEQ ID NO 1; VL is SEQ ID NO 13) and 320-591 (VH is SEQ ID NO: 3, VL is SEQ ID NO 9) inhibited the TL1a-DR3 interaction but not the TL1A-DcR3 interaction. Several antibodies with improved potency such as 320-331, 320-547, 320-583, 320-584, 320-585, 320-586, 320-587 and variants of these antibodies, are capable of inhibiting both the TL1A-DR3 and the TL1A-DcR3 interaction.

Figure 11:
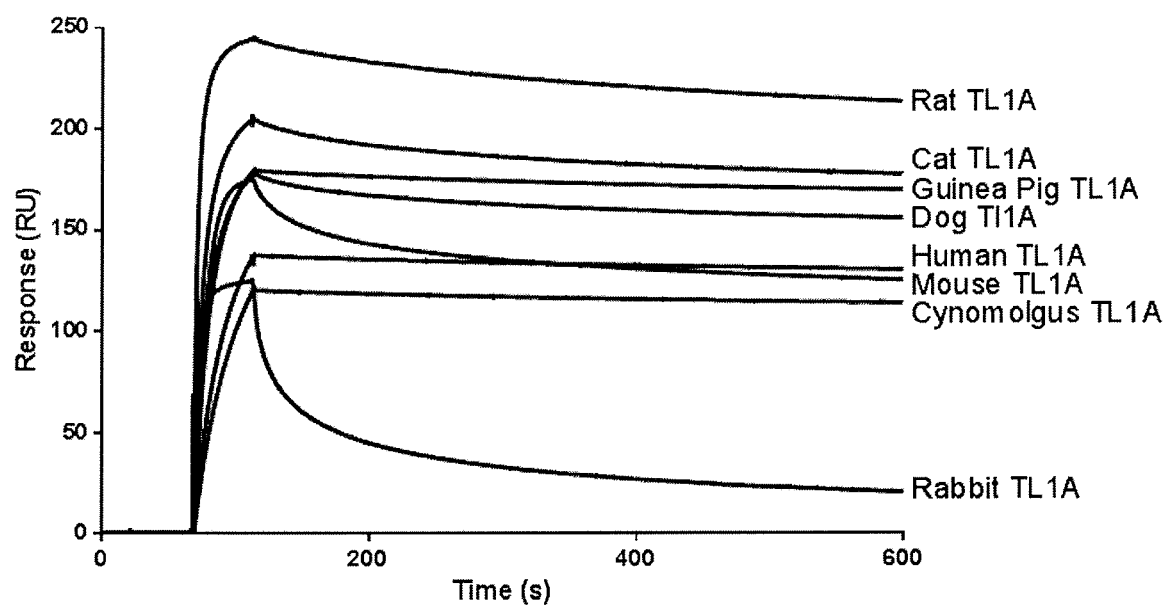
FIG. 11 shows that antibody 320-587 cross reacts with and binds to TL1A of different species; the antibody bound to TL1A from all species tested.

2.4. Species cross-reactivity of 320-587 was tested for its ability to bind to recombinantly produced TL1A from different species. The antibody bound to TL1A from all species tested (FIG. 11). The binding of 320-587 to human, rat, guinea pig, dog, cat, cynomolgus monkey TL1A had a slow dissociation rate, indicating a high affinity interaction. The antibody bound mouse and rabbit TL1A and had a fast dissociation rate.

2.5. Pre-clinical efficacy models for testing anti-TL1A antibodies in the following animal models of disease:

Asthma: allergen-induced asthma—rodent (mouse, rat or guinea pig) is sensitized by intradermal injection of ovalbumin (OVA), especially OVA derived from chicken eggs, plus alum and then challenged at least 2 weeks later by aerosolized of nebulized OVA, causing asthma-like symptoms including airways hyerreactivity, influx of eosinophils and increased production of cytokines (e.g., Hylkema et al., 2002, Clin. Exp. lmmunol. 129:390-96). Such a model could be modified by repeated challenge to present a more chronic disease profile with increased airways remodeling and fibrosis induction (e.g., Bos et al., 2007, Eur. Respir. J. 30:653-661). Alternative allergens, such as house dust mite, may also be used (e.g., Lambert et al., 1998, Am. J. Respir. Crit. Care Med. 157:1991-9). Alternatively, a nonhuman primate (e.g., cynomolgus macaque) may be sensitized and challenged with an environmental antigen such as *Ascaris suum*, leading to airways hyerreactivity, influx of eosinophils and increased production of cytokines (e.g., Wegner et al., 1991, J. Allergy Clin. Immunol.87:835-41).

COPD: Smoke inhalation-induced airways inflammation—rodent (mouse, rat or guinea pig) will be exposed to cigarette smoke 3-7 times a week for at least 4 weeks causing a pulmonary disease similar to COPD, characterized by lung accumulation of neutrophils, increased inflammatory cytokine production, lung fibrosis and pulmonary hypertension (e.g., Davis et al. (2012) PLoS One 7:e33304). A more severe form of disease may be induced by including repeat bacterial or viral infection into the lungs during smoke exposure (e.g., Li et al. (2012) Biol. Pharm. Bull. 35:1752-60). Rodents with smoke-induced COPD will be treated with anti-TL1A antibodies and screened for treatment efficacy.

Pulmonary fibrosis: Bleomycin-induced pulmonary fibrosis—rodent (mouse, rat or guinea pig) will be treated with bleomycin either by intratracheal/intranasal instillation or intravenous injection once or twice weekly for at least 3 weeks. This treatment induces significant and stable pulmonary fibrosis (e.g., Pinart et al. (2009) Resp. Physiol. Neurobiol. 166:41-46). Rodents with bleomycin-induced pulmonary fibrosis will be treated with anti-TL1A antibodies and screened for treatment efficacy.

Cystic Fibrosis: CFTR knockout ferret model—ferrets homozygous for gene knockout, or known disease-related mutations, of CFTR (causative gene in cystic fibrosis) spontaneously develop a cystic fibrosis-like disease characterized by mucus obstruction of airways, atelectasis, interstitial pneumonia and repeated lung infections with progressive lung bacterial colonization (e.g., Sun et al. (2014) Am. J. Respir. Cell Mol. Biol. 50:502-12). CFTR$^{-/-}$ ferrets will be treated with anti-TL1a antibodies and screened for treatment efficacy.

Irritable Bowel Syndrome: Stress-induced visceral hypersensitivity—Stress will be induced in rats by either neonatal-maternal separation (e.g., Coutinho et al. (2002) Am. J. Physiol. Gastrointest. Liver Physiol. 282:G307-16) or restraint of adults (e.g., Shen et al. (2010) J. Neurogastroenterol. Motil. 16:281-90). This is expected to produce altered colonic motility and visceral hypersensitivity similar to that observed in IBS patients. Stressed rats will be treated with anti-TL1A antibodies and screened for treatment efficacy.

Rheumatoid Arthritis: Collagen-induced arthritis—rodent (mouse, rat or guinea pig) will be immunized and boosted with collagen in adjuvant. Animals develop bilateral foot swelling and erythema, inflammatory infiltrate into joint area and joint damage (e.g., Bendele et al. (1999) Toxicol. Pathol. 27:134-42). Rodents with collagen-induced arthritis will be treated with anti-TL1A antibodies and screened for treatment efficacy.

Eosinophilic esophagitis: Intranasal *Aspergillus fumigatus*-induced eosinophilic esophagitis. Mice exposed to repeat intranasal instillation of *A. fumigates* develop marked esophageal eosinophilia, epithelial dysplasia and hyperplasia, and free eosinophil granules (e.g., Mishra et al. (2001) J. Clin. Invest. 107:83-90). Similarly, repeat aerosol exposure to ovalbumin over a two week period in sensitized guinea pigs causes esophageal eosinophilia with infiltration of both eosinophils and mast cells into the epithelial layer (e.g., Liu et al. (2015) Am. J. Physiol. Gastrointest. Liver Physiol. 308:G482-488). Mice or guinea pigs with eosinophilic esophagitis will be treated with anti-TL1A antibodies and screened for treatment efficacy.

Figure 13:
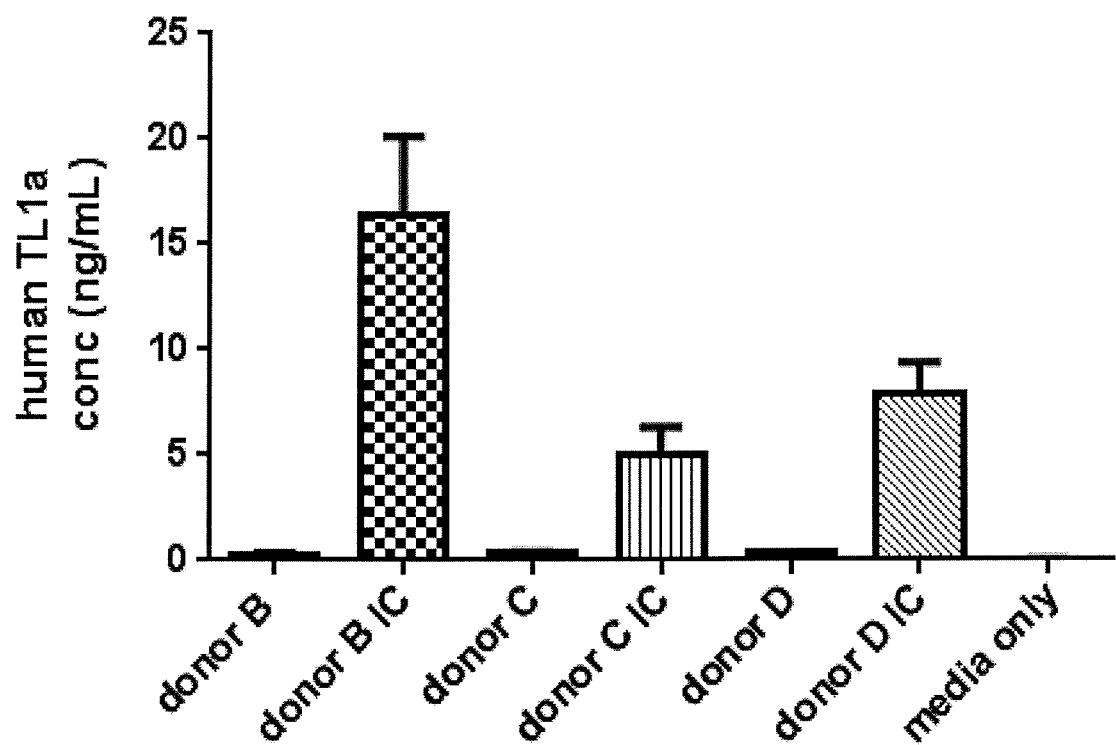
FIG. 13 shows that antibody 320-587 detects human TL1A secreted from human PBMCs stimulated with immune complexes, in an ELISA test.
Figure 14:
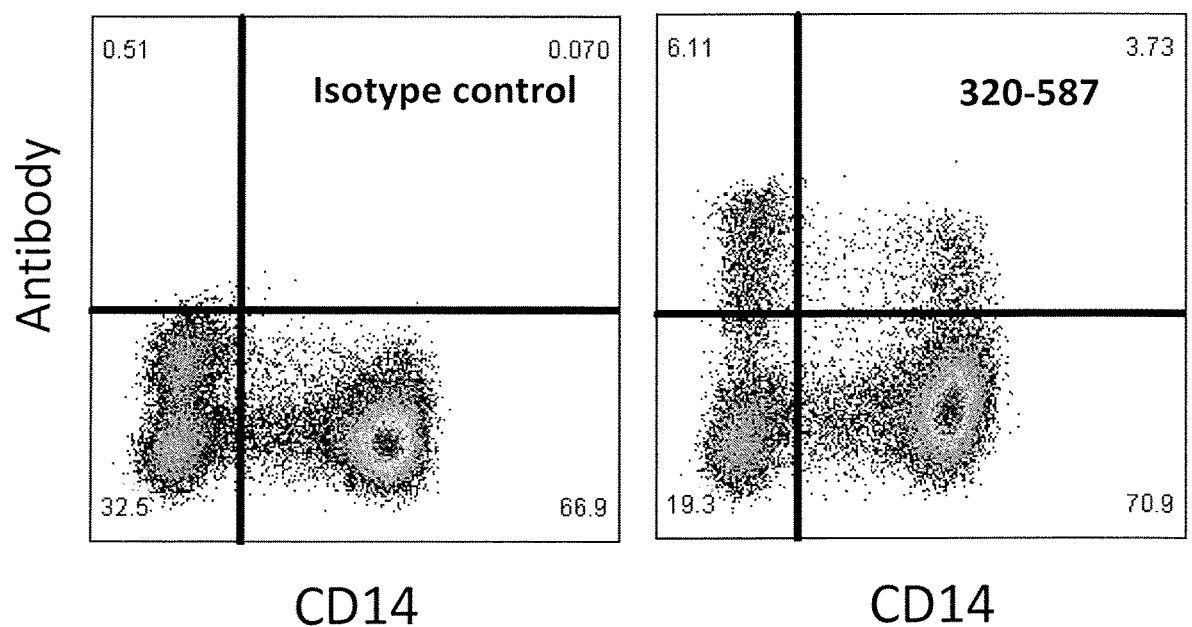
FIG. 14 shows that antibody 320-587 detects a population of human PBMCs that express membrane TL1A on their surface, in a flow cytometry test.

2.6. Use of TL1A antibodies in detecting samples containing TL1A antibodies of the disclosure can be used to detect TL1A in human samples. 320-587 was used to detect human TL1A secreted from human PBMCs stimulated with immune complexes (FIG. 13) in ELISA format. 320-587 was also used to detect a population of human PBMCs that express membrane TL1A on their surface in flow cytometry experiments (FIG. 14).

2.7. Affinity measurements of Anti-TL1A antibody binding to human TL1A by kinetic exclusion assay. Time to reach equilibrium with 320-587 as CBP: First, the $K_{on}$ rate for the 320-587/TL1A interaction was measured. Briefly, a solution was prepared by mixing 320-587 and TL1A, and aliquots were removed at various time points over 3 hours. Free 320-587 was captured by passing the solution over a column packed with Sepharose beads coated with 20 ug/mL TL1A.

Captured 320-587 was detected with an Alexa Fluor® 647-conjugated anti-human antibody (0.5 ug/mL). This assay was repeated two times yielding $K_{on}$ rates of $8.35 \times 10^5$ Ms$^{-1}$ and $7.45 \times 10^5$ Ms$^{-1}$, with an average $K^{on}$ rate of $7.90 \times 10^5$ Ms$^{-}$. The $K^{on}$ rate was then used to estimate the amount of time required to reach equilibrium at various concentrations of 320-587 using the theoretical binding curve tool provided on the Sapidyne website.

KD determination with 320-587 as CBP. The CBP, 320-587, was diluted in assay buffer (DPBS supplemented with 1 mg/ml BSA) to final concentrations of 15, 50 and 150 pM. The titrant, human TL1A was diluted in assay buffer to create a concentration series of 0.1, 0.3, 1, 3, 10, 30, 100, 300, 1000 and 3000 pM. Using the time to reach equilibrium determined above, curves that contained either 50 or 150 pM 320-587 were allowed to come to equilibrium in a 25° C. incubator for 2 days. Curves that contained 15 pM 320-587 were allowed to come to equilibrium in a 25° C. incubator for 3 days. Following the equilibration period, the free fraction of 320-587 in each reaction was quantitated as described in above. The $K_D$ values were determined using n-curve analysis of equilibrium curves generated with 15, 50 and 150 pM 320-587.

Time to reach equilibrium with TL1A as CBP: The time to reach equilibrium in this orientation was estimated using the $K_{on}$ for the 320-587/TL1A interaction, determined as described in 2.8 above. In this format, the free fraction of TL1A was captured by passing the solution over a column packed with PMMA beads coated with 30 μg/mL 320-587. Captured TL1A was detected with an anti 6x-his DyLight 650 antibody (0.75 μg/mL). This assay was repeated two times yielding $K_{on}$ rates of $6.11 \times 10^5$ Ms$^{-1}$ and $5.74 \times 10^5$ Ms$^{-1}$, with an average $K_{on}$ rate of $5.93 \times 10^5$ Ms$^{-1}$.

$K_D$ determination with TL1A as CBP: The CBP, human TL1A, was diluted in assay buffer to final concentrations of 30, 100 and 300 pM. The titrant, 320-587, was diluted in assay buffer to create a concentration series of 0.05, 0.15, 0.5, 1.5, 5, 15, 50, 150, 500, 1500 and 5000 pM.

Using the time to reach equilibrium determined above, all curves were allowed to come to equilibrium in a 25° C. incubator for 3 days. Following the equilibration period, the free fraction of TL1A in each reaction was quantitated as described above. The $K_D$ values were determined using n-curve analysis of equilibrium curves generated with 30, 100 and 300 pM TL1A.

Good agreement was observed between the two KinExA methods as well as a relatively low % error. The $K_D$ value for the interaction of TL1A with 320-587 determined using 320-587 as the CBP was 40.97±8.33 pM (Table 13), while the $K_D$ obtained using TL1A as the CBP was 41.52±13.5 pM (Table 14).

TABLE 13

Affinity: Sepharose beads coated with TL1A; 320-587 as the CBP.

| Assay No: | $K_D$ (pM) | % Error |
|---|---|---|
| 1 | 40.43 | 4.57 |
| 2 | 52.03 | 5.61 |
| 3 | 46.31 | 4.76 |
| 4 | 32.42 | 3.74 |
| 5 | 33.66 | 3.9 |
| Average | 40.97 | |
| SD | 8.33 | |
| % CV | 20 | |

TABLE 14

Affinity: PMMA beads coated with 320-587; TL1A as the CBP.

| Assay No: | $K_D$ (pM) | % Error |
|---|---|---|
| 1 | 33.39 | 5.33 |
| 2 | 57.1 | 5.51 |
| 3 | 34.07 | 3.9 |
| Average | 41.52 | |
| SD | 13.5 | |
| % CV | 33 | |

3.0. Preclinical efficacy models for testing anti-TL1a antibodies. 3.0.1. Asthma.

Figure 15:
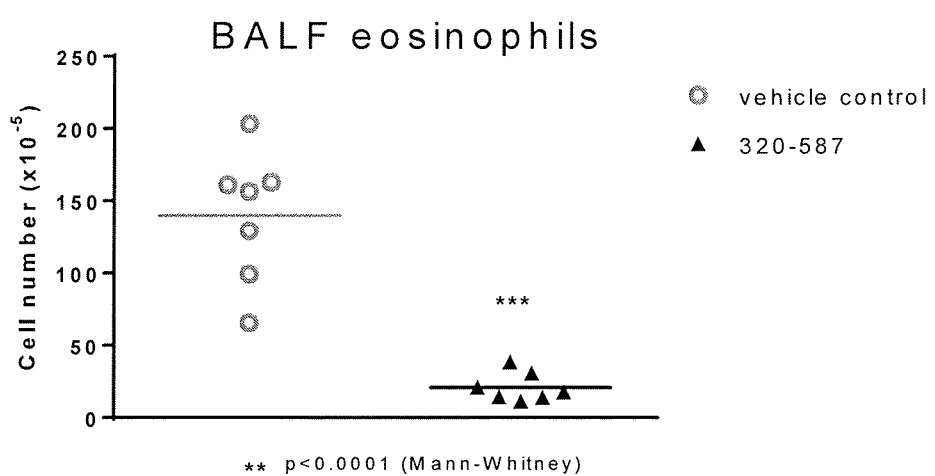
FIG. 15 shows that rats having acute OVA-induced asthma treated with antibody 320-587 had significantly reduced eosinophils in the bronchoalveolar lavage fluid (BALF).

Acute ovalbumin-induced asthma in rats. Brown-Norway rats were sensitized with OVA by i.p. injection on day 0 then challenged with OVA aerosol daily on days 35-42. Rats were treated with antibody 320-587 or vehicle by i.v. injection on days 14, 21, 28 and 35. Bronchoalveolar lavage fluid (BALF) was assessed for total and differential cells on day 43. Treatment was found to significantly reduce BALF eosinophils (FIG. 15).

Figure 17A:
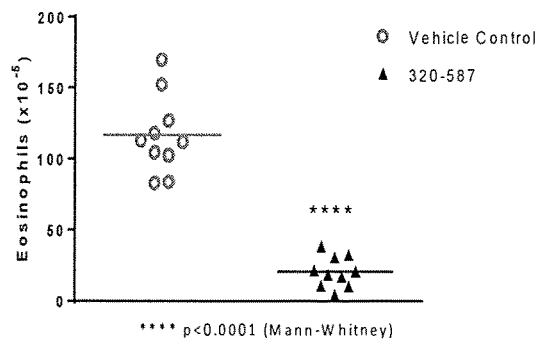
FIGS. 17A through 17E show treatment of rats having chronic OVA-induced asthma treated with antibody 320-587 had improvements in (FIG. 17A) BALF eosinophils, (FIG. 17B) BALF macrophages, (FIG. 17C) BALF IL-13, (FIG. 17D) goblet cell hyperplasia as assessed by PAS reactivity, and (FIG. 17E) mucosal thickening as assessed from H&E stained sections.
Figure 17B:
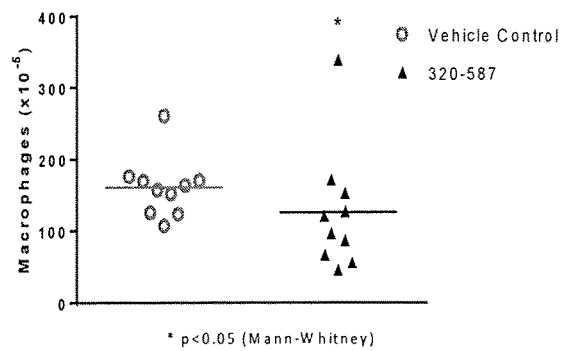
Figure 17C:
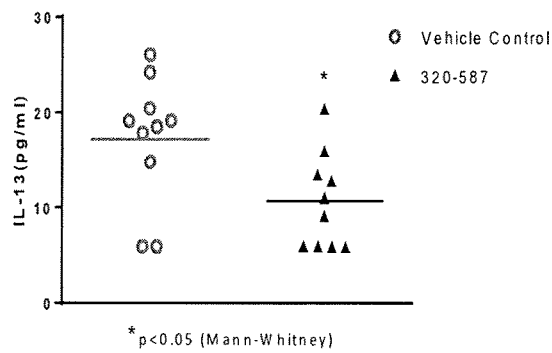
Figure 17D:
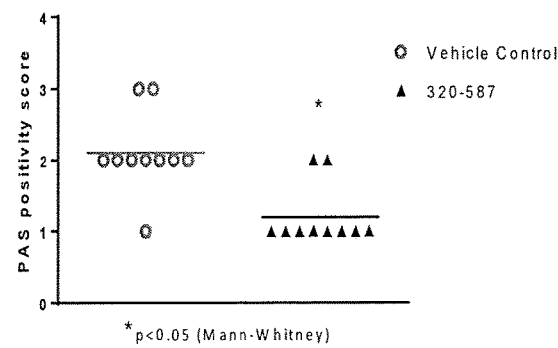
Figure 17E:
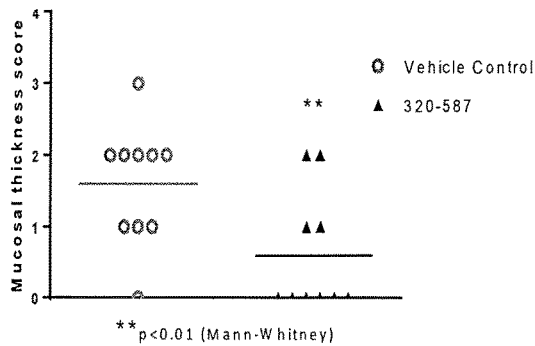

Chronic ovalbumin-induced asthma in rats. Rats were sensitized with OVA plus alum by i.p. injection on days 0 and 7, and then challenged with OVA aerosol twice weekly for 3 weeks starting on day 14 through day 31, and on 5 consecutive days from days 37 to 42. Animals were treated with antibody 320-587 or vehicle i.v. on days 24, 29, 34 and 39. BALF was assessed for total and differential cells, and a panel of cytokines on day 43. Lung sections were stained with hematoxylin and eosin (H&E), and periodic-acid Schiff (PAS), and assessed for a range of pathologies. Treatment with 320-587 significantly decreased BALF eosinophils and macrophages (FIGS. 17A and 17B), BALF IL-4 and IL-13 (FIG. 17C), goblet cell hyperplasia (FIG. 17D) and the thickness of the bronchial epithelial layer (FIG. 17E), compared to the vehicle.

Figure 16B:
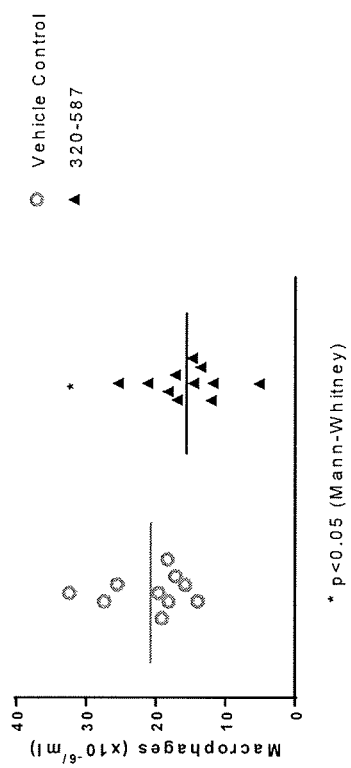
FIGS. 16A through 16D show treatment of guinea pigs having acute OVA-induced asthma treated with antibody 320-587 had improvements in (FIG. 16A) BALF eosinophils, (FIG. 16B) BALF macrophages, (FIG. 16C) Airways hyper responsiveness after early asthmatic reaction, and (FIG. 16D) Magnitude of early asthmatic reaction.
Figure 16A:
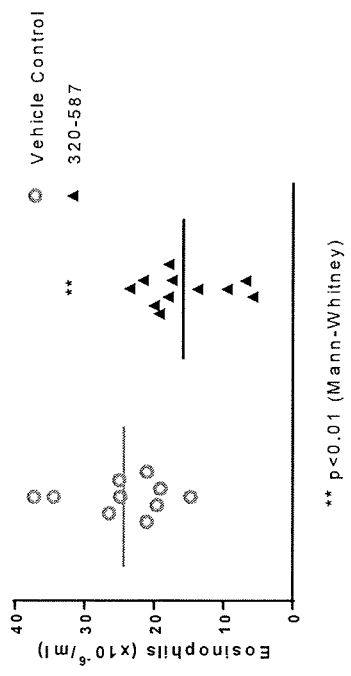
Figure 16D:
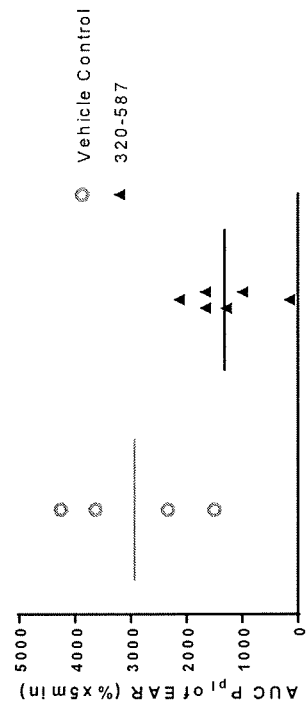
Figure 16C:
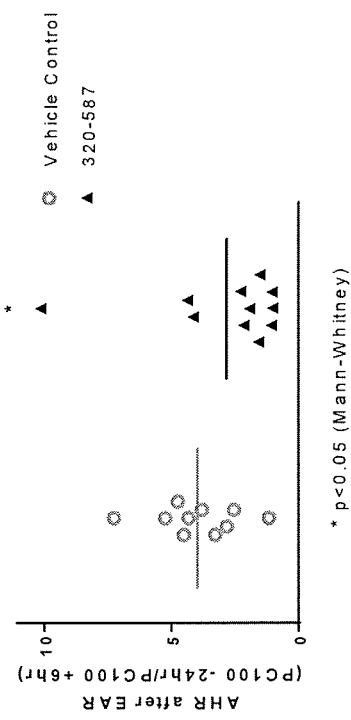

Acute ovalbumin-induced asthma in guinea pigs. Male Dunkin Hartley guinea pigs were sensitized to ovalbumin and thereafter underwent surgery to install a balloon catheter to measure lung function and early and late asthmatic reactions. On day 16, 20, 24 and 28, animals were treated i.p. with antibody 320-587 or vehicle. Challenge with ovalbumin (0.05-0.1%) aerosol was performed 30 minutes after the last treatment. Airway responsiveness (AHR) to histamine was measured 24 h before challenge, 6 h after challenge (directly after the early asthmatic reaction) and 24 h after challenge (directly after the late asthmatic reaction). The nature and size of the early and late asthmatic reactions was also be recorded by online registration of lung function over the entire 24 h period. Animals were sacrificed 25 h after challenge and bronchoalveolar lavage performed. BALF was assessed for total and differential cells. Treatment with 320-587 significantly decreased both eosinophils and macrophages in BALF (FIGS. 16A and 16B) as well as ameliorating AHR after the early asthmatic reaction (FIG. 16C) and the overall magnitude of the early asthmatic reaction (FIG. 16D), as compared to vehicle.

Figure 18:
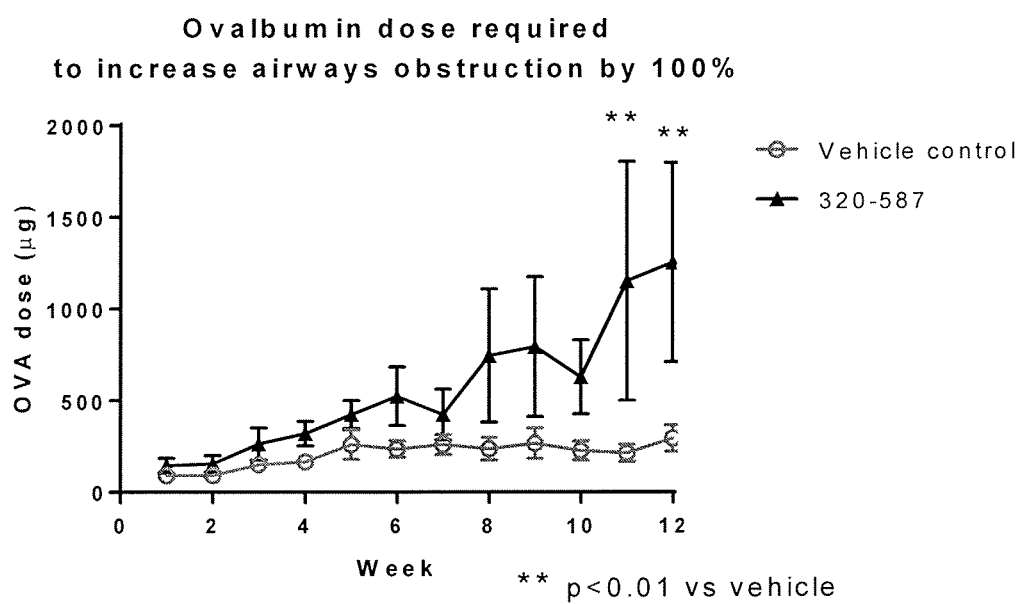
FIG. 18 shows the dose of ovalbumin required to double airways obstruction.

Chronic ovalbumin-induced asthma in guinea pigs. Male Dunkin Hartley guinea pigs were sensitized to ovalbumin, and 4 weeks thereafter challenged with ovalbumin weekly for 12 weeks. Ovalbumin challenge (0.05-0.5%) was performed by inhalation of aerosolized solution until airway obstruction was observed. Animals were treated with antibody 320-587 or vehicle i.p. every 5 days starting week 8 of ovalbumin challenges. Airways function, by means of airways responsiveness to histamine, was measured before the initial challenge, 24 hours before the final challenge, and 6 hours after the final challenge. Although no effect on AHR induced by histamine challenge was observed, antibody 320-587 significantly decreased the allergic response to OVA, as progressively increasing doses of OVA were required to induce airways obstruction (FIG. 18).

The differences in antibody therapeutic effect observed in the acute and chronic asthma models in guinea pigs is believed to be a function of the model itself. It is believed that in the chronic model, the degree of AHR decreases over time and, accordingly, becomes less responsive to treatment. In the art, the acute model is generally used to observe compound effects on airways responsiveness, and the chronic model is generally used to observe compound effects on airways remodelling. Remodelling assessments are ongoing. Nevertheless, it was surprising to observe the antibodies having an impact on the response to allergen—although the antibody didn't substantially impact absolute AHR (response to histamine) at this stage, it had significantly decreased the direct allergic response to antigen.

3.0.2. Inflammatory Bowel Disease

Figure 12:
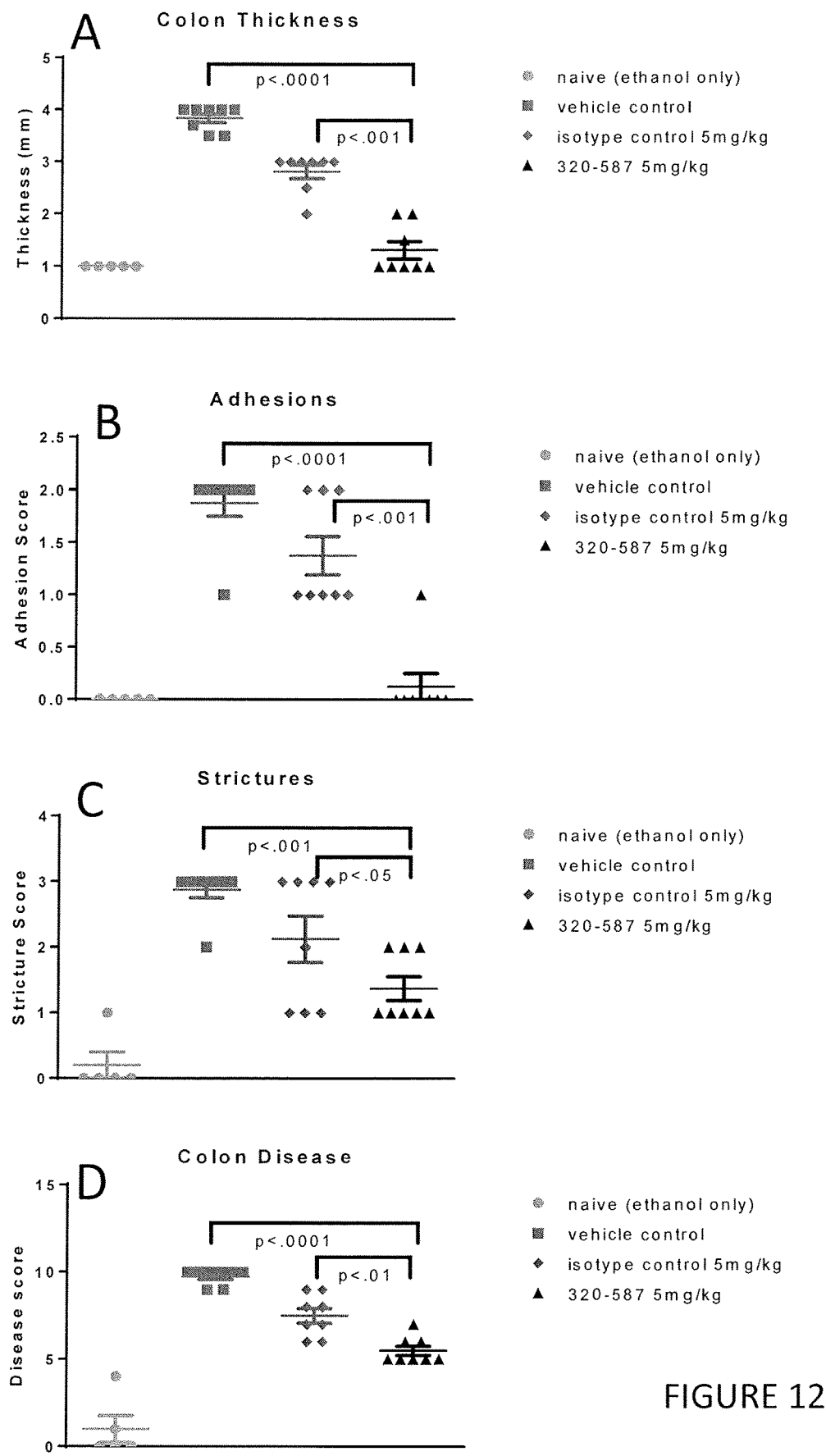
FIG. 12 shows the results of the administration of antibody 320-587 in a rat TNBS-induced colitis model, demonstrating that the antibody significantly ameliorates symptoms of colitis
Figure 19:
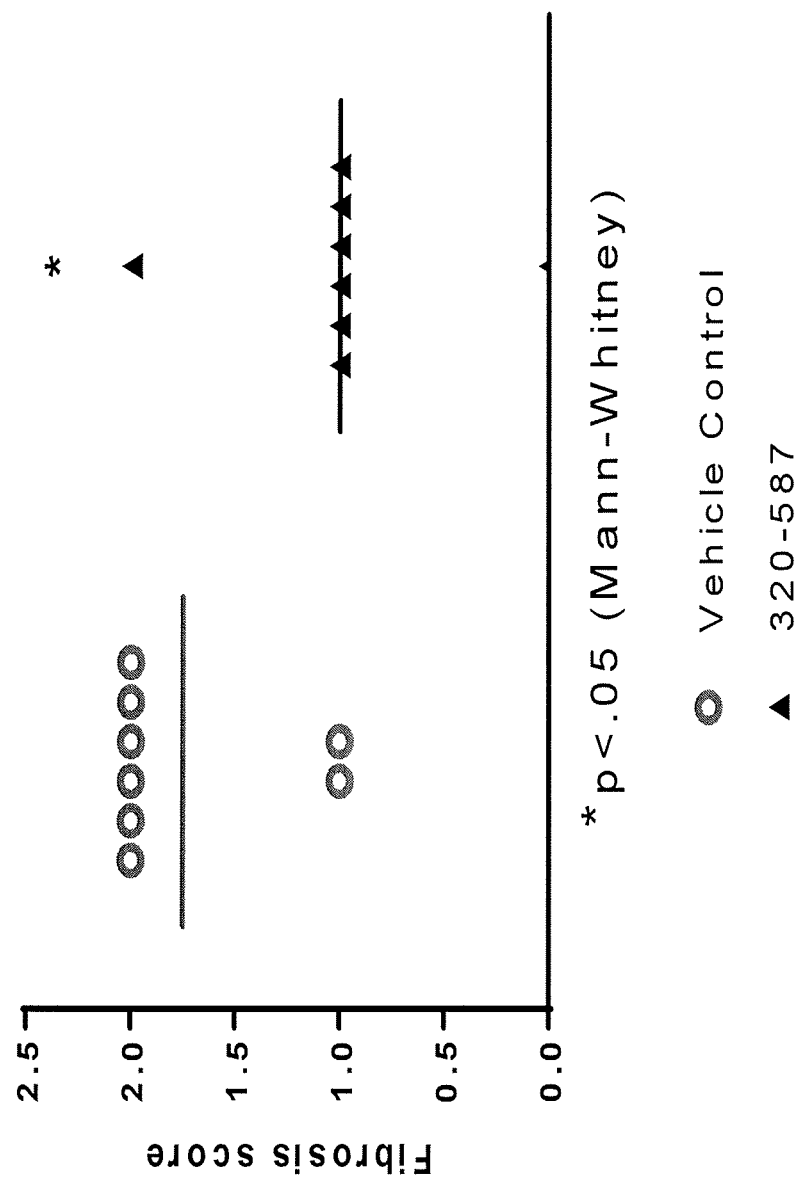
FIG. 19 shows treatment of rats having TNBS-induced colitis treated with antibody 320-587 had improvements in ulcer area fibrosis.

TNBS-induced colitis in rats: Rats were treated with a single dose of tri-nitrobenzenesulfonic acid in ethanol by intrarectal instillation dose. Control animals received equivalent volume of ethanol only. Over a space of 7 days, animals developed focal colitis characterized by ulceration of the colon with inflammatory infiltrate and varying degrees of fibrosis (e.g., Wirtz et al. (2007) Nat. Protoc. 2:541-546). 320-587 administration significantly reduced multiple disease indicators including colon thickness (FIG. 12A), number and severity of adhesions (FIG. 12B), and number and severity of strictures (FIG. 12C) leading to a significantly milder disease than animals treated with either vehicle or an isotype-matched irrelevant antibody (FIG. 12D). Decreased colon fibrosis (FIG. 19) was also observed in 320-587 treated animals.

Figure 20A:
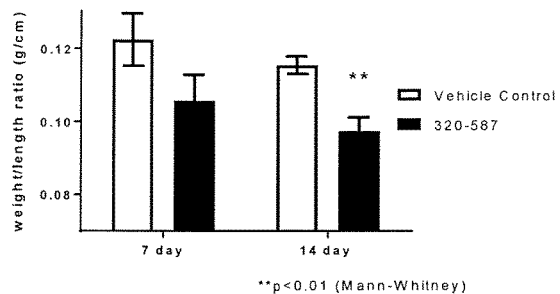
FIGS. 20A through 20E show a comparison of rats having TNBS-induced colitis with DNBS-induced colitis, treated with antibody 320-587 and the effects at 7 and 14 days, on (FIG. 20A) colon weight/length ratio, (FIG. 20B) colon fibrosis, (FIG. 20C) colon infiltrate, and (FIG. 20D) colon damage.
Figure 20B:
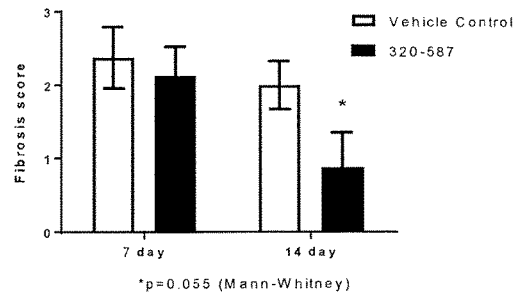
Figure 20C:
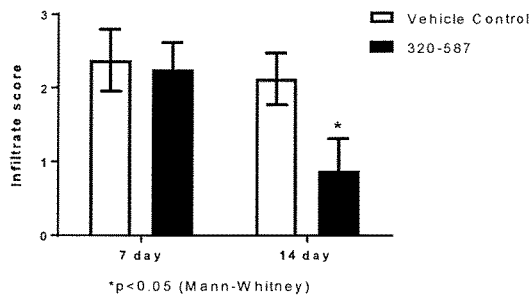
Figure 20D:
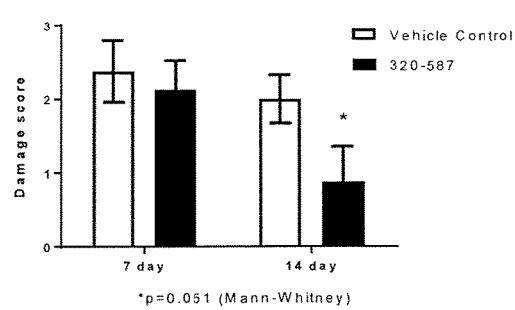
Figure 20E:
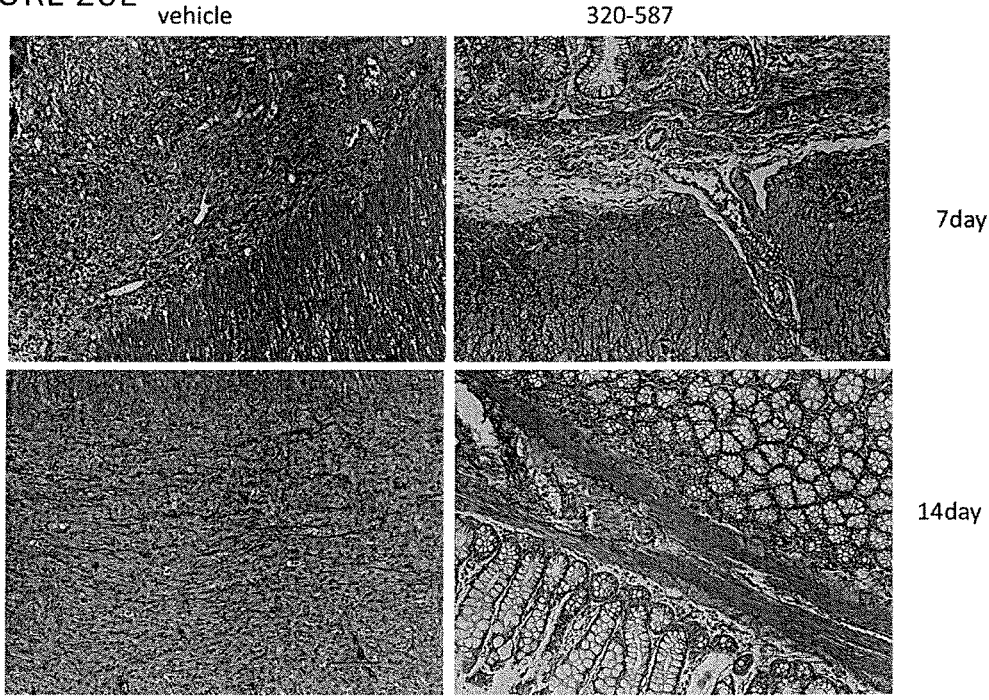

Comparison of disease after 7 and 14 days in DNBS-induced colitis in rats. Colitis was induced as described above using dinitrobenzenesulfonic acid (DNBS) instead of TNBS, and the rats used in the DNBS experiments were Wistar rats. Animals were treated with antibody 320-587 or vehicle i.v. on days 1 and 8. Groups were assessed for colitis 7 and 14 days post-DNBS and disease severity compared between the two timepoints. Treatment with antibody 320-587 had limited effect on day 7, but by day 14, animals treated with antibody 320-587 showed significant improvement in colon weight and length (FIG. 20A), fibrosis (FIG. 20B), inflammatory infiltrate (FIG. 20C) and colon damage (FIG. 20D). Representative sections of ulcer area colon (FIG. 20E) show the extent of damage repair and reduction in fibrosis at 14 days. At both 7 and 14 days, vehicle-treated animals showed extensive inflammatory infiltrate and fibrosis with significant loss of intestinal architecture. In contrast, 320-587-treated animals showed significant inflammatory infiltrate, fibrosis and loss of intestinal architecture at 7 days but these effects are largely reversed by 14 days.

The differences observed in the antibody therapeutic effects observed in the TNBS and DNBS models are believed to arise from the use of different strains of rats (Sprague-Dawley for TNBS versus Wistar for DNBS). Each rat strain has differences in their responses to immunological challenges such that the kinetics of their response in these models is believed to be different. As well, TNBS and DNBS are different structurally, and are believed to induce variations in the disease state.

Figure 21B:
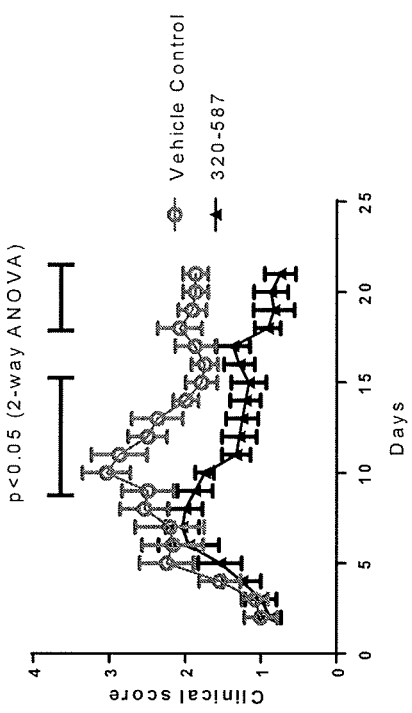
FIGS. 21A through 21C show treatment of rats having DSS-induced colitis treatment with antibody 320-587 had improvements in (FIG. 21A) weight change during DSS administration, (FIG. 21B) Clinical scoring during DSS administration, and (FIG. 21C) colon weight/length ratio.
Figure 21A:
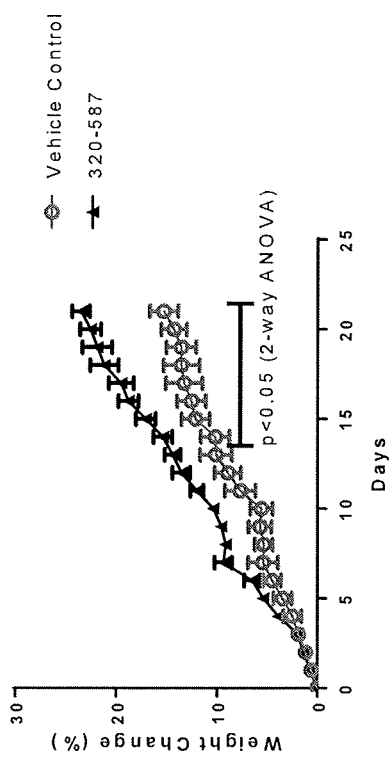
Figure 21C:
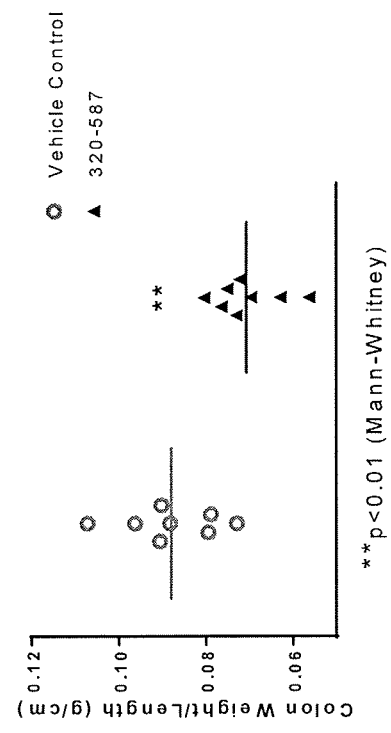

Chronic (21 day) DSS-induced colitis in rats. Rats were given dextran sulfate sodium (DSS) at a concentration of 5% w/v in drinking water for 7 days, then 2% w/v in drinking water for a further 14 days. Animals developed diarrhea, diffuse colonic inflammation, goblet cell hyperplasia, and crypt epithelial damage and ulceration (e.g. Randhawa et al. (2014) Korean J. Physiol. Pharmacol. 18:279-88). Rats were treated with antibody 320-587 or vehicle by intravenous injection on days 5, 12 and 19. Animals were weighed and assessed for clinical disease (diarrhea and occult blood) daily, and colon weight and length were assessed on day 21. Antibody 320-587 treatment significantly reversed DSS-induced slowdown of weight gain (FIG. 21A), ameliorated clinical signs of disease (FIG. 21B) and improved colon weight and length (FIG. 21C).

Figure 22:
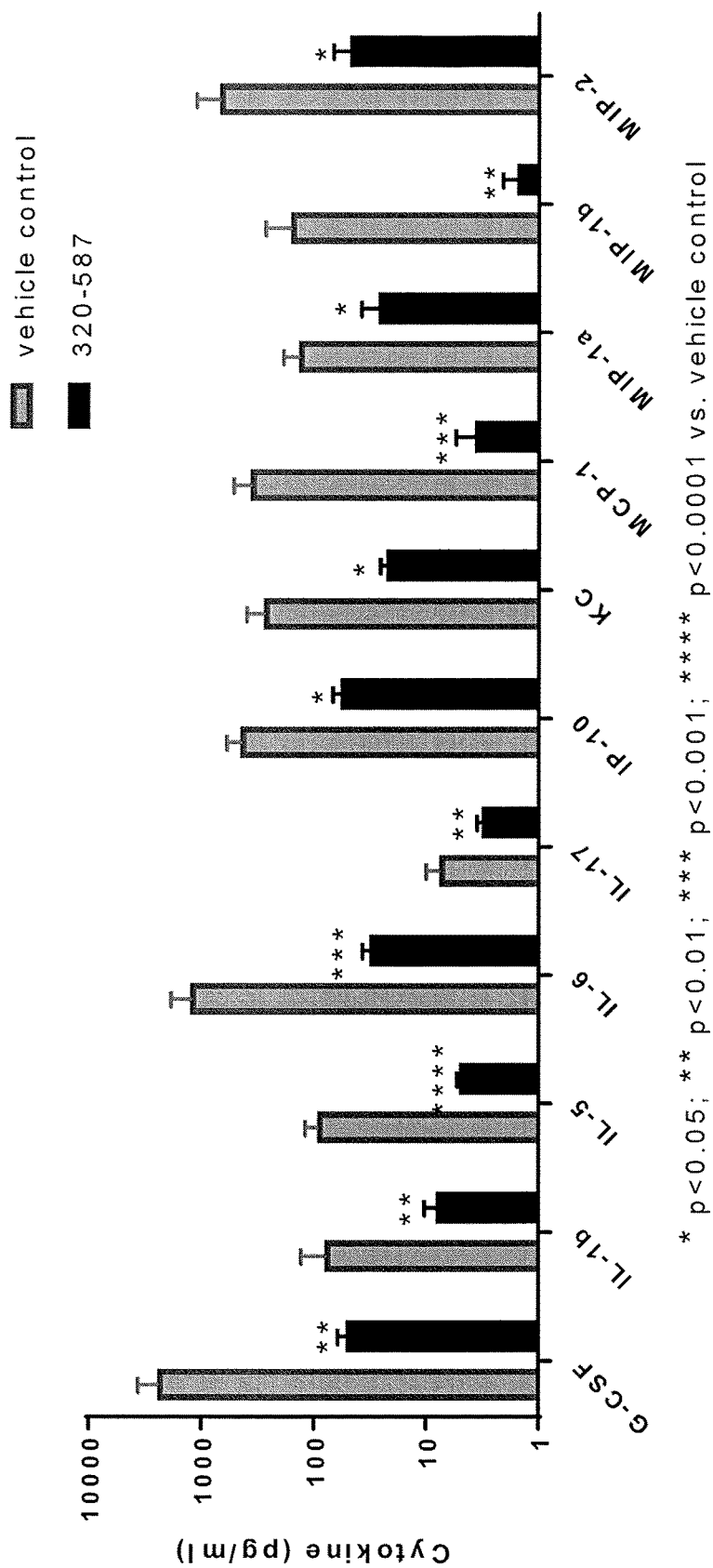
FIG. 22 shows changes in TL1A-induced intraperitoneal cytokines in response to 320-587 treatment.

Induction of intraperitoneal cytokines by recombinant human TL1A. Intraperitoneal injection of recombinant mouse TL1A can induce the production of inflammatory cytokines such as IL-5. In this study, mice received a single dose of either antibody 320-587 or vehicle then an hour later were treated with recombinant human TL1A (rhTL1A) 40 µg/mouse. Six hours after rhTL1A dosage, peritoneal lavage was performed and the peritoneal fluid assessed for cytokines and chemokines by multiplex assay. Treatment with antibody 320-587 significantly decreased peritoneal concentrations of cytokines G-CSF, IL-1b, IL-5, IL-6, IL-17, and chemokines IP-10, KC, MCP-1, MIP-1a, MIP-1b, MIP-2 (FIG. 22).

The disclosure is not limited to the embodiments described and exemplified above, but is capable of variation and modification within the scope of the appended claims.

We claim:

1. A method for treating a respiratory tract disease, comprising administering to a subject in need of treatment for a respiratory tract disease a recombinant antibody, comprising a heavy chain variable region CDR1 comprising the amino acid sequence of SEQ ID NO: 15, a heavy chain variable region CDR2 comprising the amino acid sequence of SEQ ID NO: 21, a heavy chain variable region CDR3 comprising the amino acid sequence of SEQ ID NO: 17, a light chain variable region CDR1 comprising the amino acid sequence of SEQ ID NO: 29, a light chain variable region CDR2 comprising the amino acid sequence of SEQ ID NO: 19, and a light chain variable region CDR3 comprising the amino acid sequence of SEQ ID NO: 30, provided that when the heavy chain variable region comprises the amino acid sequence of SEQ ID NO: 1, the light chain variable region does not comprise the amino acid sequence of SEQ ID NO: 2, wherein the antibody specifically binds to TNF-Like ligand 1A (TL1A) and wherein the antibody is capable of inhibiting the interaction of TL1A with the death receptor 3 (DR3).

2. The method according to claim 1, wherein the respiratory tract disease is asthma, chronic obstructive pulmonary disease (COPD), pulmonary sarcoidosis, allergic rhinitis, pulmonary fibrosis, or cystic fibrosis.

3. The method according to claim 1, wherein the light chain variable region CDR3 comprises the amino acid sequence of SEQ ID NO: 20.

4. The method according to claim 1, wherein the light chain variable region CDR3 comprises the amino acid sequence of SEQ ID NO: 22.

5. The method according to claim 4, wherein the respiratory tract disease is asthma, chronic obstructive pulmonary disease (COPD), pulmonary sarcoidosis, allergic rhinitis, pulmonary fibrosis, or cystic fibrosis.

6. The method according to claim 1, wherein the light chain variable region CDR1 comprises the amino acid sequence of SEQ ID NO: 24, and the light chain variable region CDR3 comprises the amino acid sequence of SEQ ID NO: 22.

7. The method according to claim 1, wherein the light chain variable region CDR1 comprises the amino acid sequence of SEQ ID NO: 25, and the light chain variable region CDR3 comprises the amino acid sequence of SEQ ID NO: 22.

8. The method according to claim 1, wherein the light chain variable region CDR1 comprises the amino acid sequence of SEQ ID NO: 26, and the light chain variable region CDR3 comprises the amino acid sequence of SEQ ID NO: 22.

9. The method according to claim 1, wherein the light chain variable region CDR3 comprises the amino acid sequence of SEQ ID NO: 27.

10. A method for treating a respiratory tract disease, comprising administering to a subject in need of treatment for a respiratory tract disease a recombinant antibody, comprising a heavy chain variable region CDR1 comprising the amino acid sequence of SEQ ID NO: 15, a heavy chain variable region CDR2 comprising the amino acid sequence of SEQ ID NO: 28, a heavy chain variable region CDR3 comprising the amino acid sequence of SEQ ID NO: 17, a light chain variable region CDR1 comprising the amino acid sequence of SEQ ID NO: 29, a light chain variable region CDR2 comprising the amino acid sequence of SEQ ID NO: 19, and a light chain variable region CDR3 comprising the amino acid sequence of SEQ ID NO: 22, provided that when the heavy chain variable region comprises the amino acid sequence of SEQ ID NO: 1, the light chain variable region does not comprise the amino acid sequence of SEQ ID NO: 2, wherein the antibody specifically binds to TNF-Like ligand 1A (TL1A) and wherein the antibody is capable of inhibiting the interaction of TL1A with the death receptor 3 (DR3).

11. The method according to claim 10, wherein the heavy chain variable region CDR2 comprises the amino acid sequence of SEQ ID NO: 16.

12. The method according to claim 10, wherein the heavy chain variable region CDR2 comprises the amino acid sequence of SEQ ID NO: 16, and the light chain variable region CDR1 comprises the amino acid sequence of SEQ ID NO: 23.

13. The method according to claim 10, wherein the heavy chain variable region CDR2 comprises the amino acid sequence of SEQ ID NO: 16, and the light chain variable region CDR1 comprises the amino acid sequence of SEQ ID NO: 24.

14. The method according to claim 10, wherein the heavy chain variable region CDR2 comprises the amino acid sequence of SEQ ID NO: 16, and the light chain variable region CDR1 comprises the amino acid sequence of SEQ ID NO: 25.

15. The method according to claim 10, wherein the heavy chain variable region CDR2 comprises the amino acid sequence of SEQ ID NO: 16, and the light chain variable region CDR1 comprises the amino acid sequence of SEQ ID NO: 26.

16. A method for treating a respiratory tract disease, comprising administering to a subject in need of treatment for a respiratory tract disease a recombinant antibody comprising a heavy chain variable region CDR1 comprising the amino acid sequence of SEQ ID NO: 15, a heavy chain variable region CDR2 comprising the amino acid sequence of SEQ ID NO: 21, a heavy chain variable region CDR3 comprising the amino acid sequence of SEQ ID NO: 17, a light chain variable region CDR1 comprising the amino acid sequence of SEQ ID NO: 18, a light chain variable region CDR2 comprising the amino acid sequence of SEQ ID NO: 19, and a light chain variable region CDR3 comprising the amino acid sequence of SEQ ID NO: 22, wherein the antibody specifically binds to TNF-Like ligand 1A (TL1A) and wherein the antibody is capable of inhibiting the interaction of TL1A with the death receptor 3 (DR3).

17. The method according to claim 16, wherein the respiratory tract disease is asthma, chronic obstructive pulmonary disease (COPD), pulmonary sarcoidosis, allergic rhinitis, pulmonary fibrosis, or cystic fibrosis.

18. The method according to claim 16, wherein the respiratory tract disease is asthma.

19. The method according to claim 16, wherein the antibody comprises a human IgG1 heavy chain constant region.

20. The method according to claim 16, wherein the antibody comprises a human light chain lambda constant region.

21. The method according to claim 16, wherein the antibody comprises a human IgG1 heavy chain constant region and a human light chain lambda constant region.

22. The method according to claim 21, wherein the respiratory tract disease is asthma, chronic obstructive pulmonary disease (COPD), pulmonary sarcoidosis, allergic rhinitis, pulmonary fibrosis, or cystic fibrosis.

23. The method according to claim 21, wherein the respiratory tract disease is asthma.

24. A method for treating a respiratory tract disease, comprising administering to a subject in need of treatment for a respiratory tract disease a recombinant antibody comprising a heavy chain variable region comprising the amino acid sequence of SEQ ID NO:3 and a light chain variable region comprising the amino acid sequence of SEQ ID NO:4.

25. The method according to claim 24, wherein the respiratory tract disease is asthma, chronic obstructive pulmonary disease (COPD), pulmonary sarcoidosis, allergic rhinitis, pulmonary fibrosis, or cystic fibrosis.

26. The method according to claim 24, wherein the respiratory tract disease is asthma.

27. The method according to claim 24, wherein the antibody comprises a light chain comprising the amino acid sequence of SEQ ID NO:61.

28. The method according to claim 24, wherein the antibody comprises a heavy chain comprising the amino acid sequence of SEQ ID NO: 60.

29. The method according to claim 24, wherein the antibody comprises a heavy chain comprising the amino acid sequence of SEQ ID NO: 60 and a light chain comprising the amino acid sequence of SEQ ID NO: 61.

30. The method according to claim 29, wherein the respiratory tract disease is asthma, chronic obstructive pulmonary disease (COPD), pulmonary sarcoidosis, allergic rhinitis, pulmonary fibrosis, or cystic fibrosis.

31. The method according to claim 29, wherein the respiratory tract disease is asthma.

* * * * *